United States Patent [19]

Rosenberg

[11] Patent Number: 4,895,574
[45] Date of Patent: Jan. 23, 1990

[54] PIEZOELECTRIC MOTIVATOR FOR PROSTHETIC DEVICES

[76] Inventor: Larry Rosenberg, 3440 Caroline Ave., Culver City, Calif. 90230

[21] Appl. No.: 617,715

[22] Filed: Jun. 6, 1984

[51] Int. Cl.$^4$ ............................................. A61F 1/24
[52] U.S. Cl. ..................................... 623/24; 623/27; 623/57
[58] Field of Search ..................... 128/774, 630, 1 R; 604/14; 434/272; 310/311, 328–333, 340, 342, 344, 345, 12–15; 623/14, 24, 27, 57

[56] References Cited

U.S. PATENT DOCUMENTS

| | | | |
|---|---|---|---|
| 3,882,551 | 5/1975 | Helmer et al. | 623/14 |
| 4,342,936 | 8/1982 | Marcus et al. | 310/330 |
| 4,510,412 | 4/1985 | Suda et al. | 310/331 X |
| 4,546,500 | 10/1985 | Bell | 623/14 X |

OTHER PUBLICATIONS

Bailey's, *Textbook of Microscopic Anatomy*, 18th Edition, Williams & Wilkins, Baltimore Md., ©1984, pp. 261–286.

Primary Examiner—Francis Jaworski
Attorney, Agent, or Firm—Leah Bas Meyer Malke; Ben Shlomo Itzhak; Larry Rowan

[57] ABSTRACT

The invention embodies the construction and implementation of synthetic muscle elements into numerous prosthetic devices. The aforesaid synthetic muscle elements consist of piezoelectric Gels; which function to motivate artificial limbs, rotate artificial joints, institute peristaltic motion in synthetic muscle systems and perform other activities consistant with the operation of organic muscle tissue. Sensory elements and ancillary systems embodied within said synthetic muscle means are responsive to evoked potentials generated by the neurons or other impulse conducting structures of the user. The aforesaid synthetic muscle has the additional capacity to sense, measure and act in a compensatory fashion to adjust their operation to biochemicals emitted by the user including, neural humoral secretions, endocrine levels, the formation of metabolites and the tension or partial pressures of gases such as $CO_2$, $O_2$, or other substances.

16 Claims, 51 Drawing Sheets

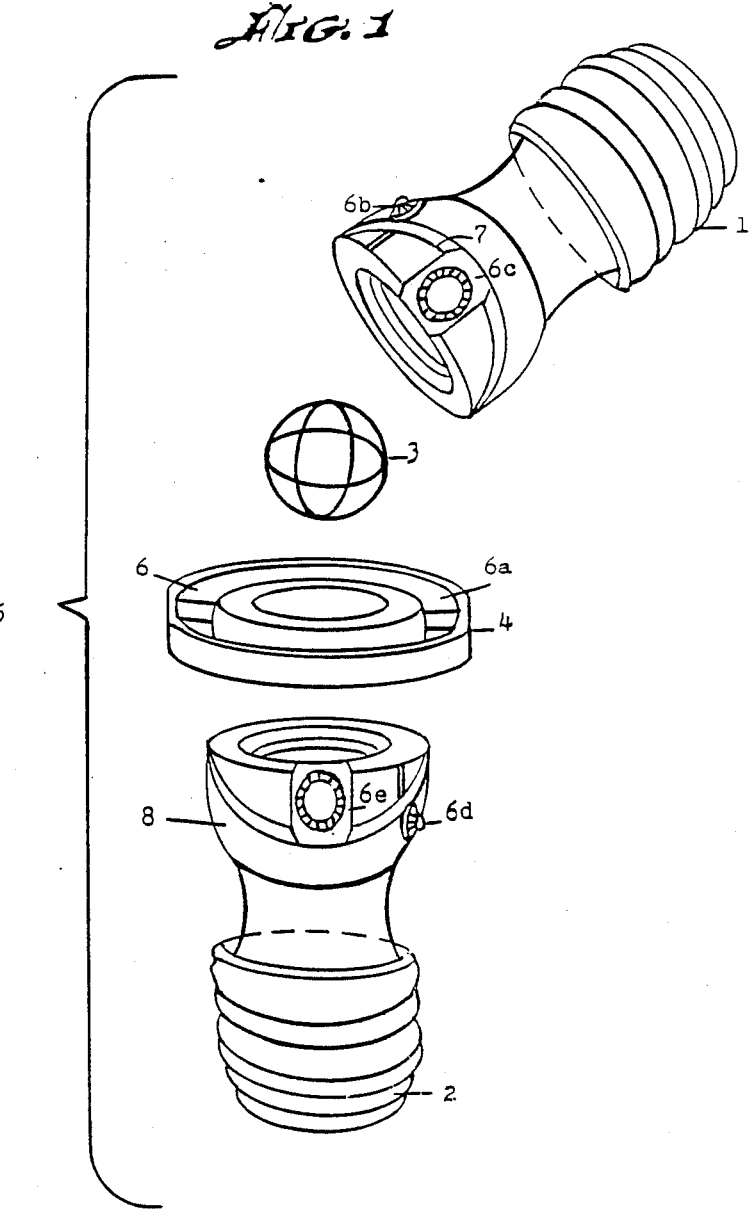

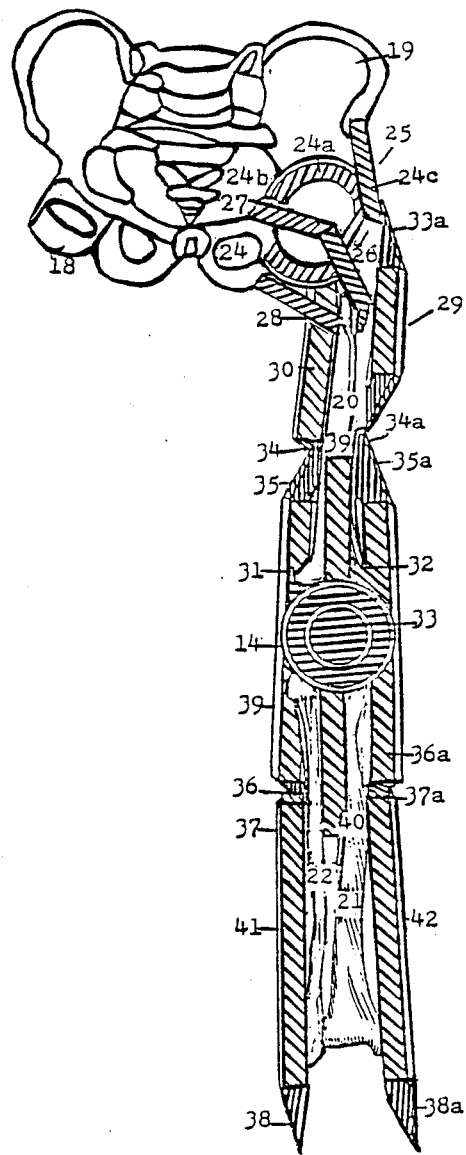

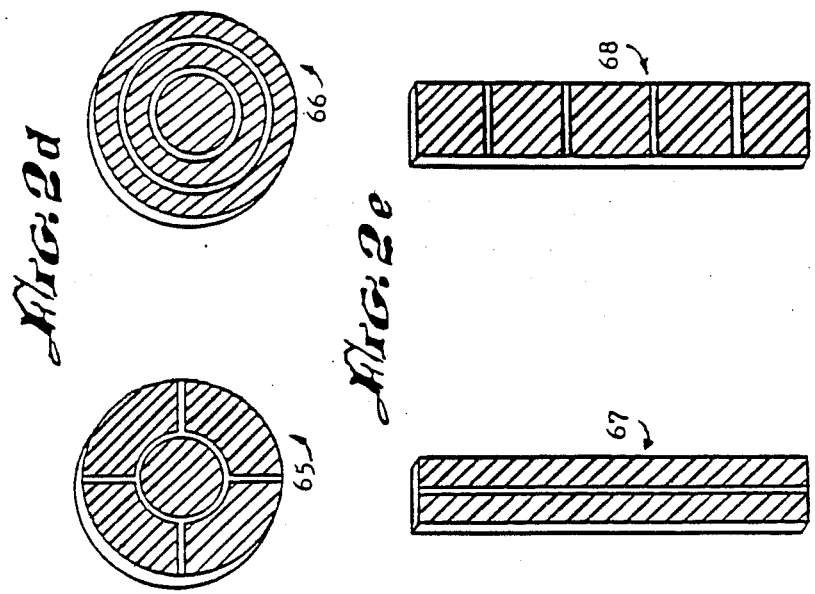

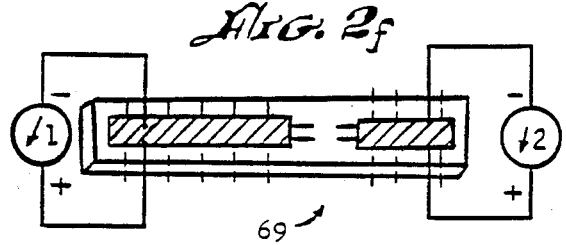
FIG. 2f
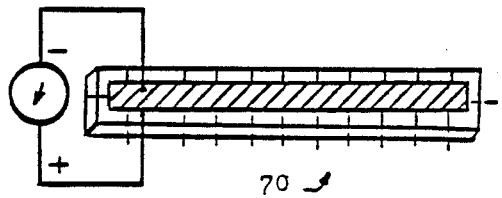
FIG. 2g
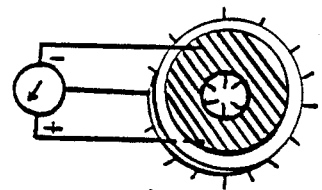
FIG. 2h
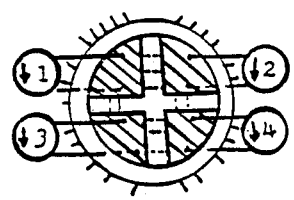

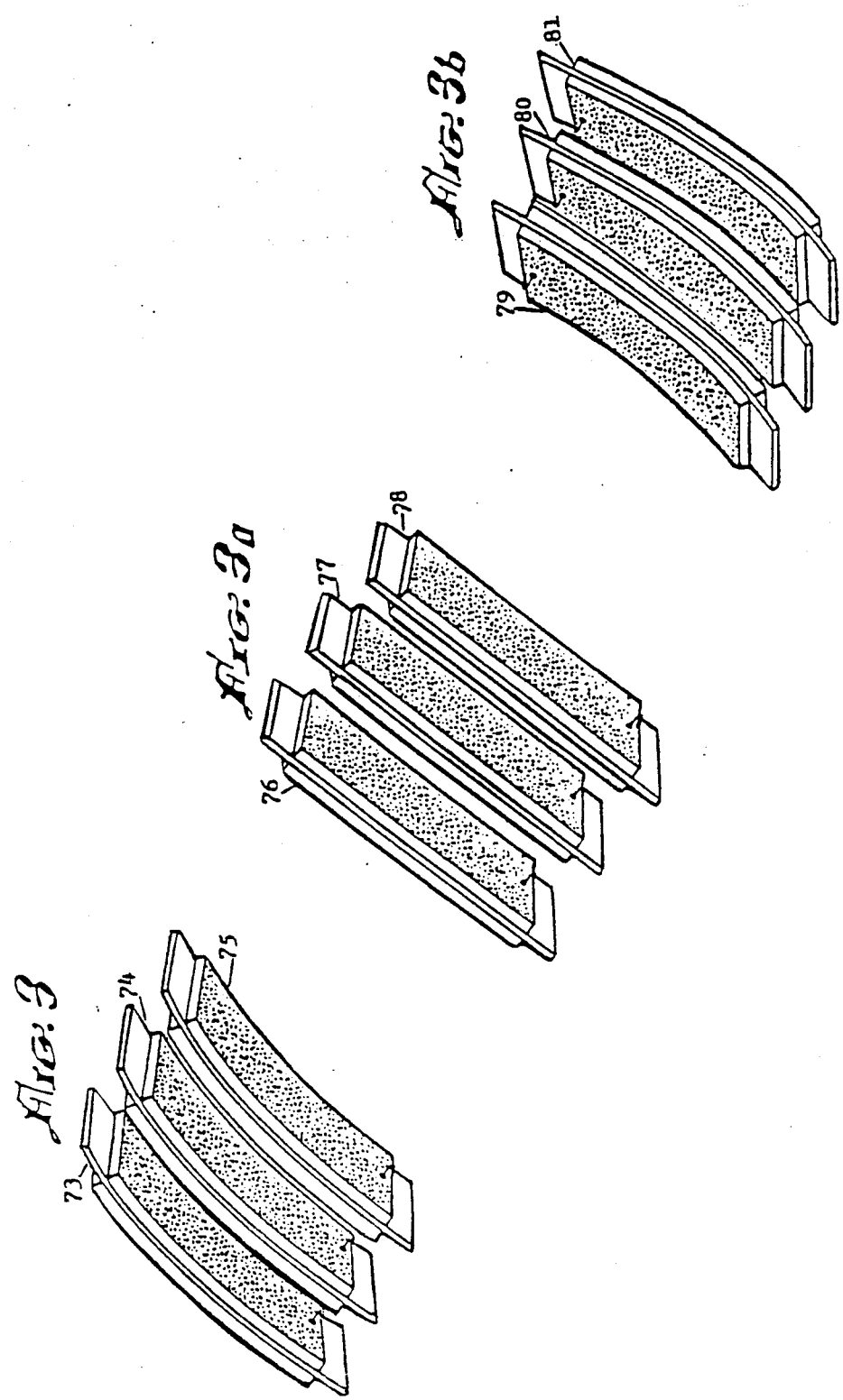

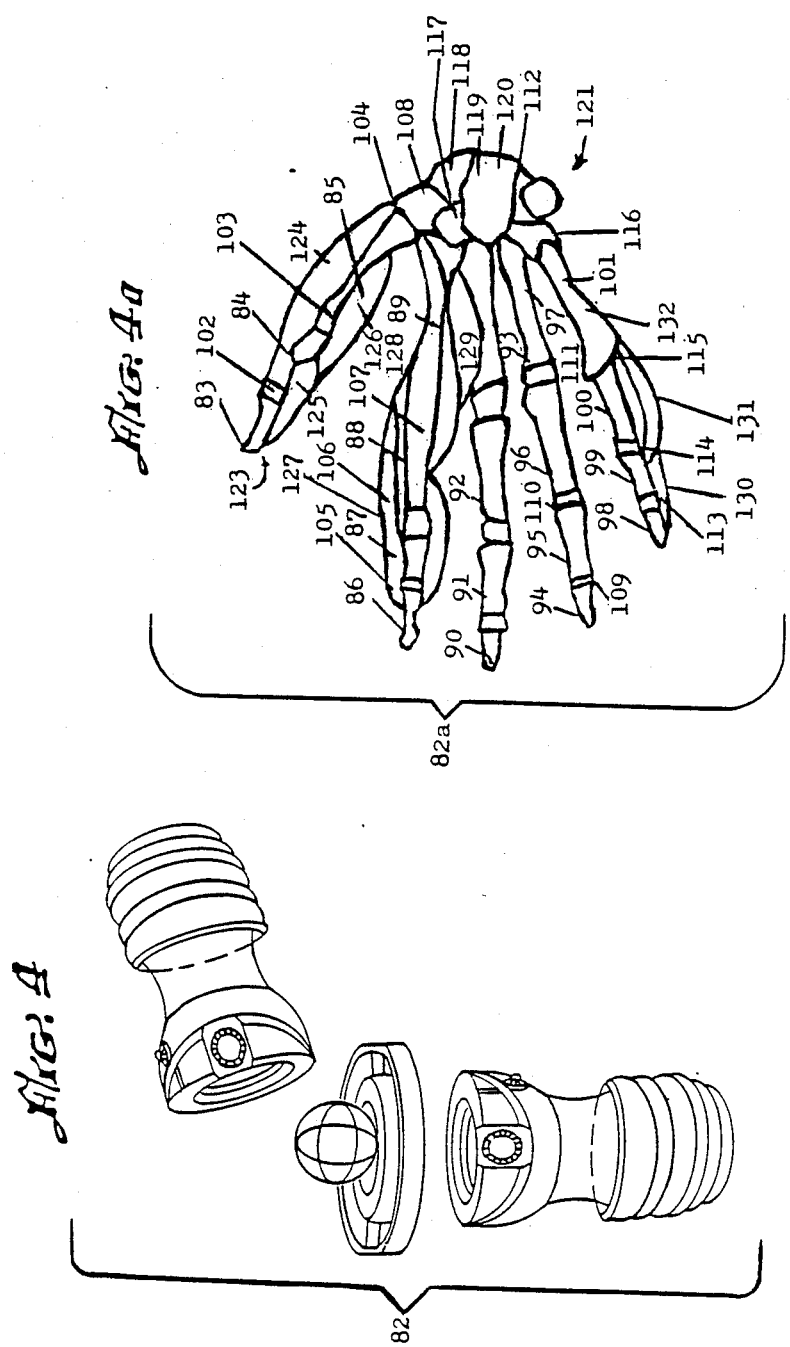

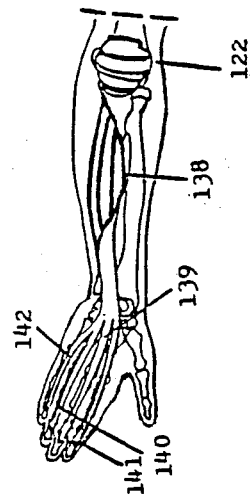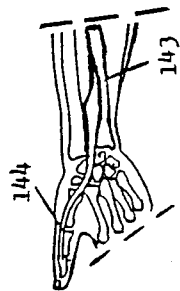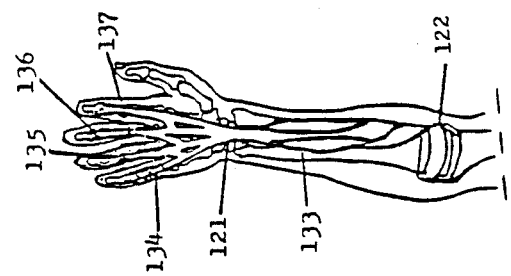

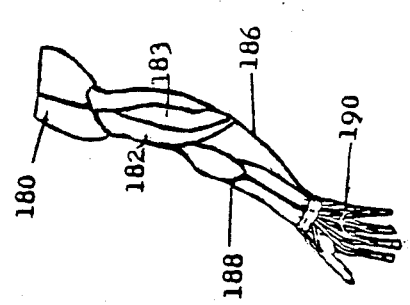
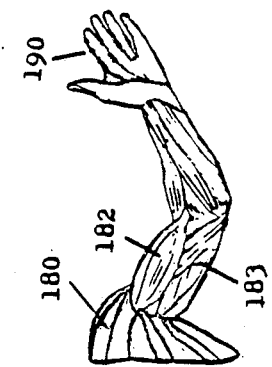
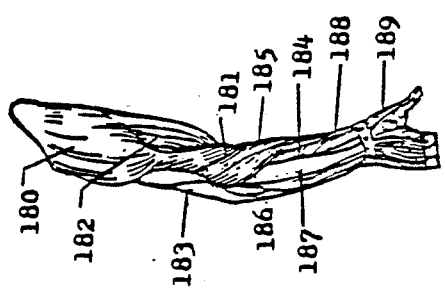

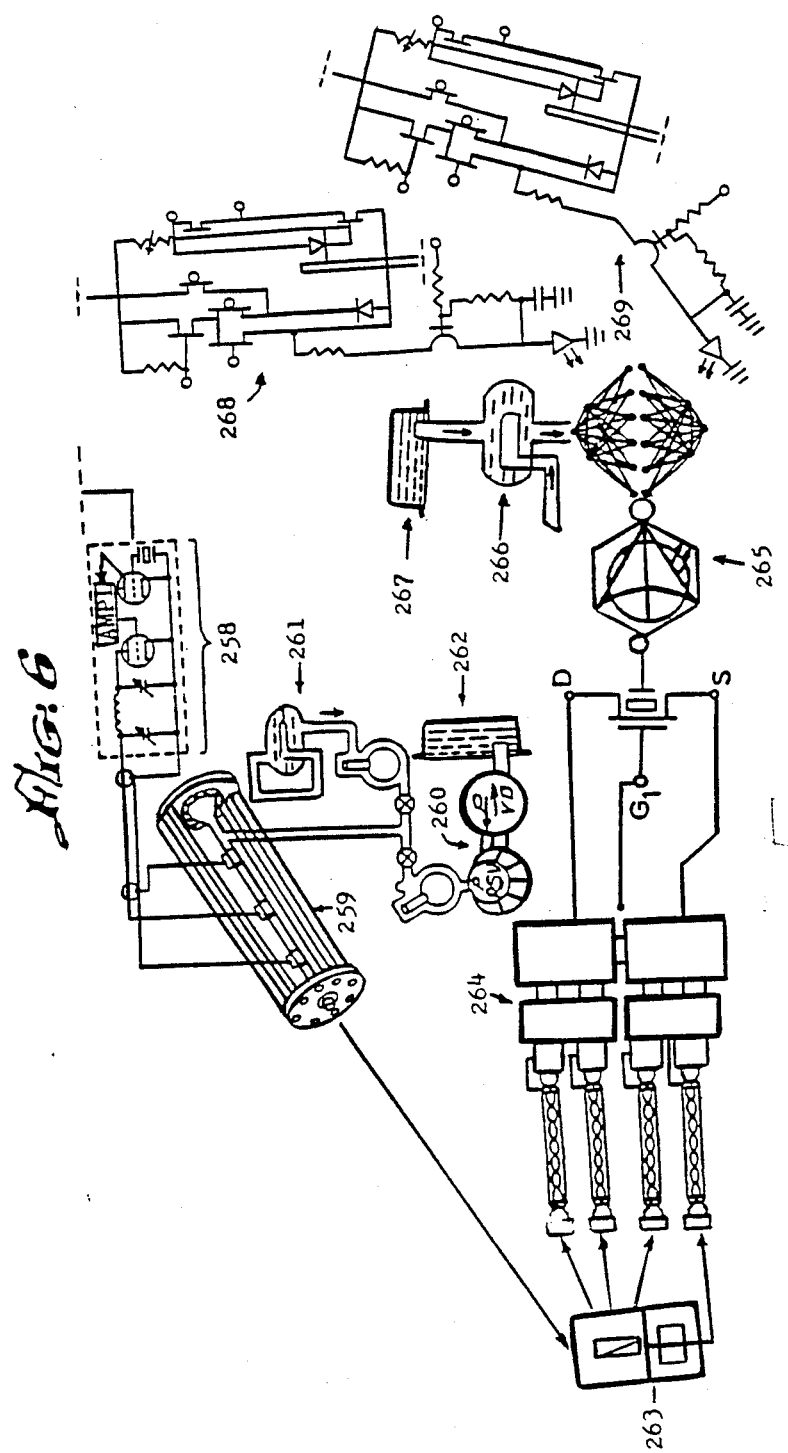

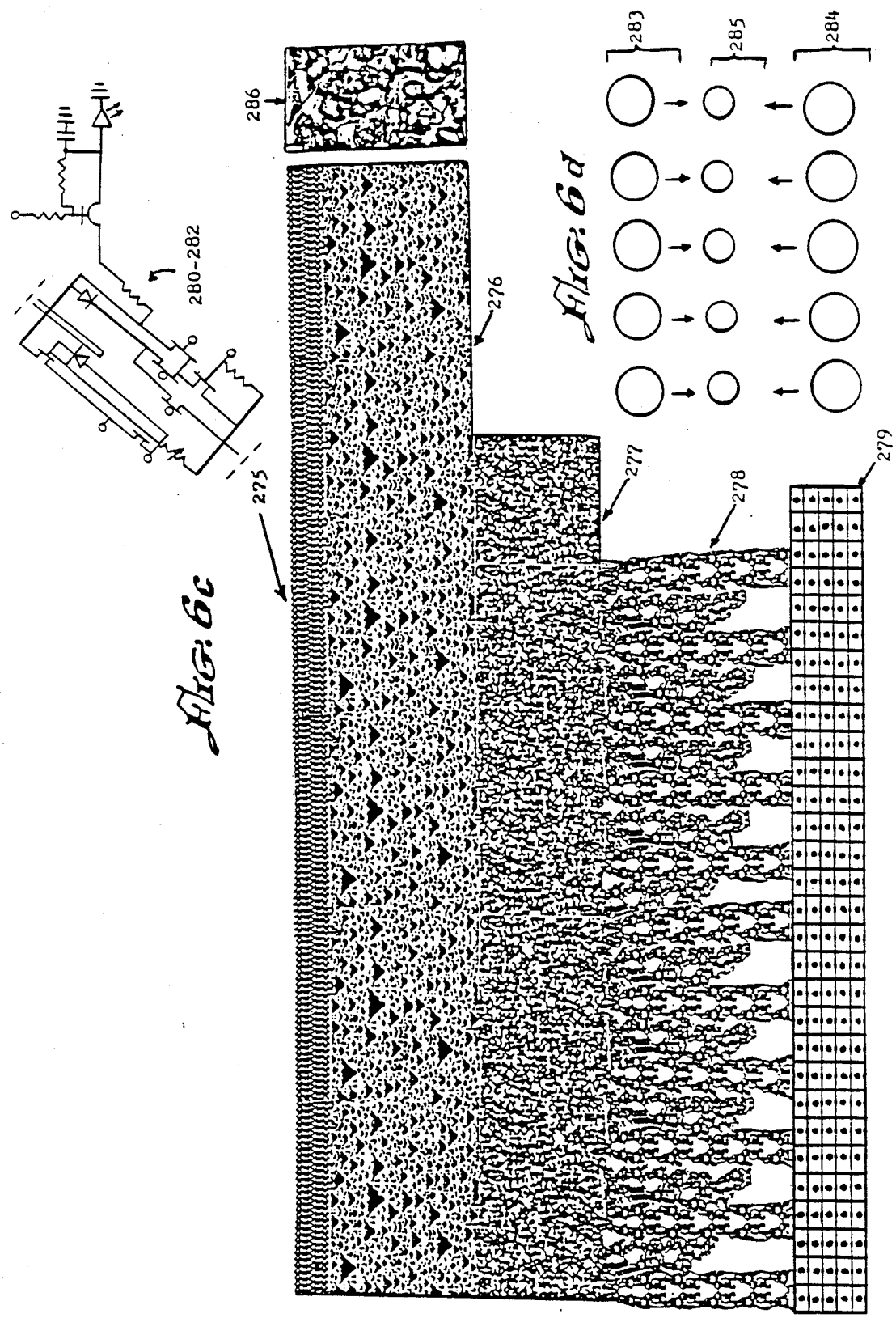

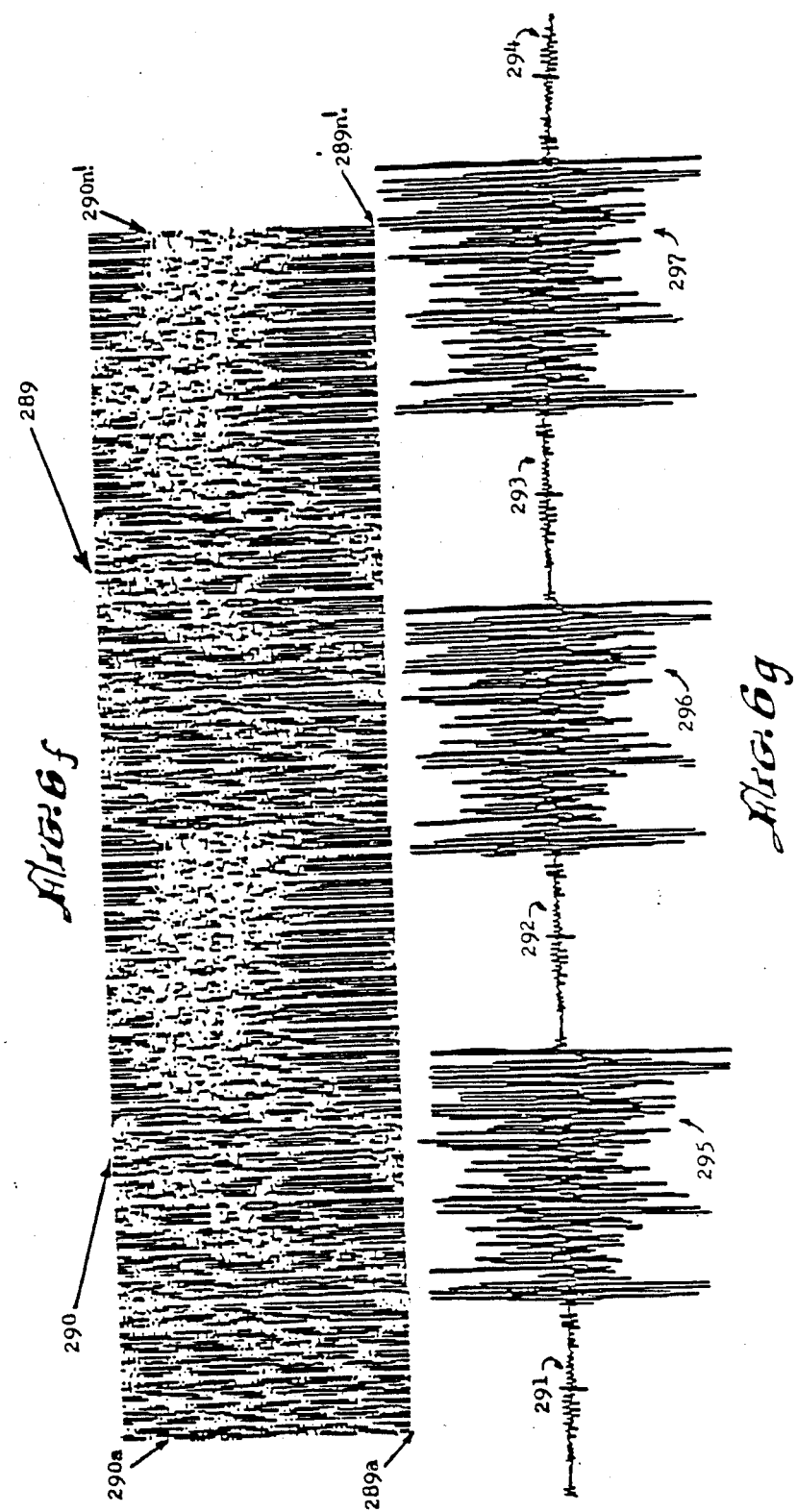

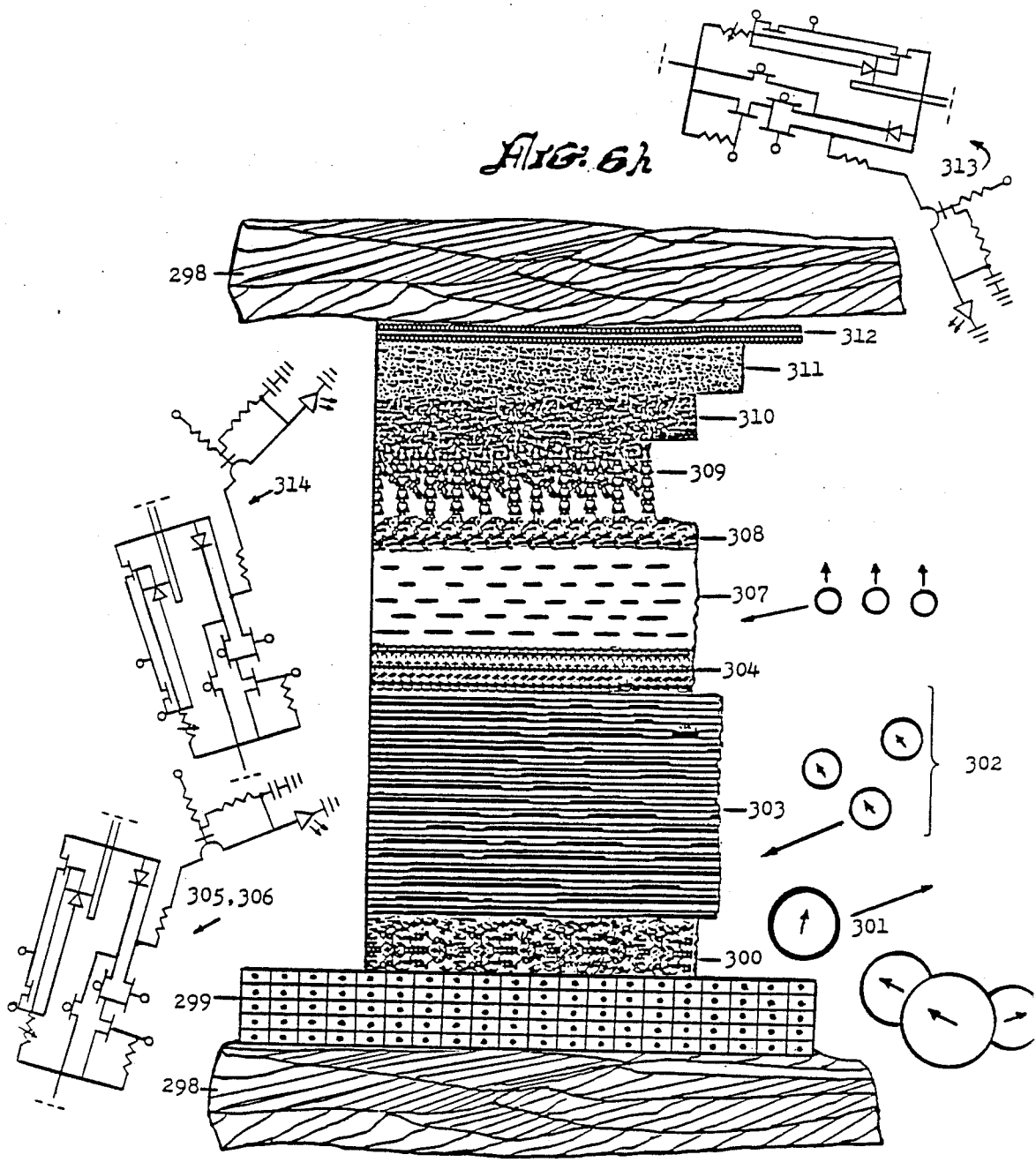

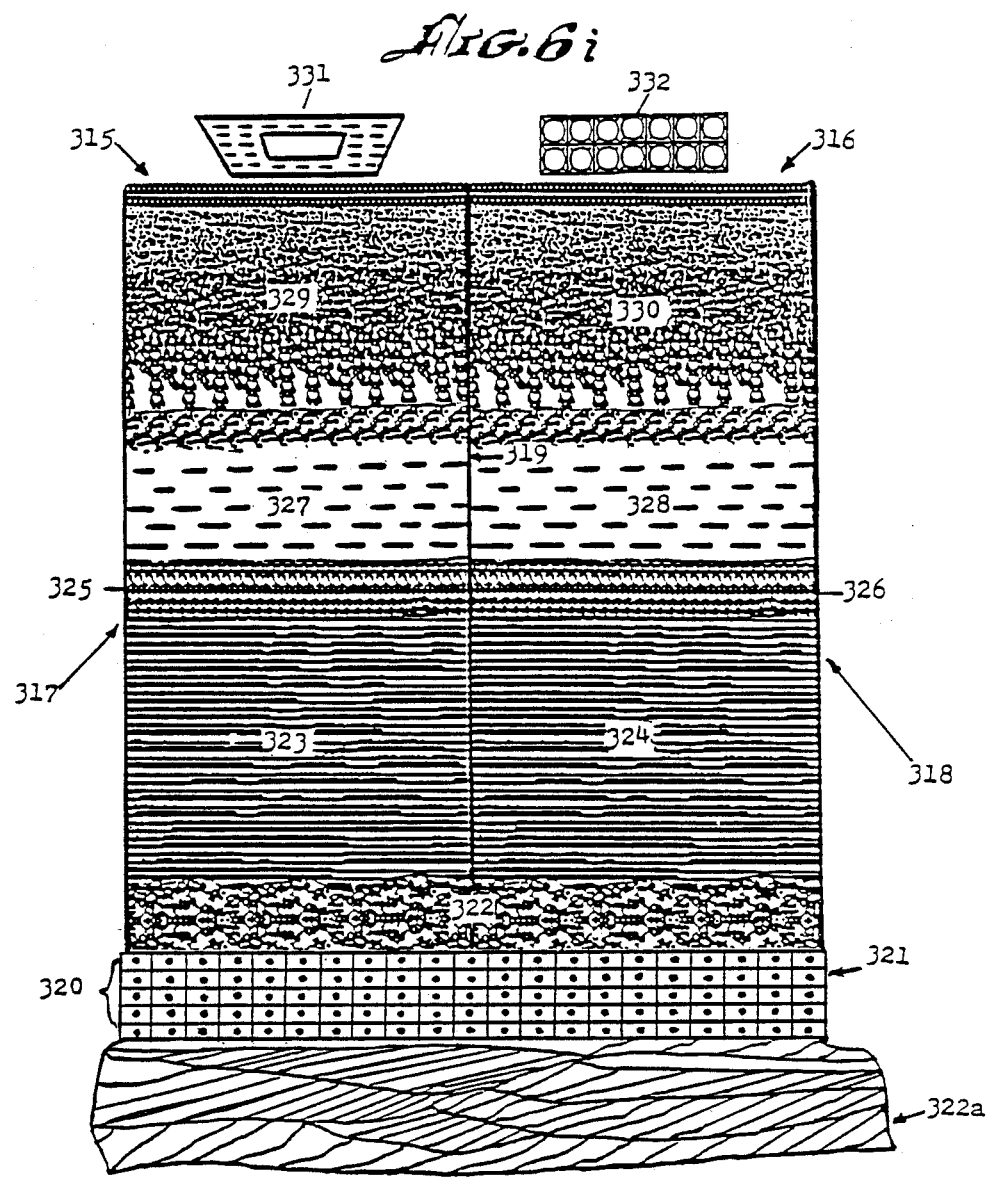

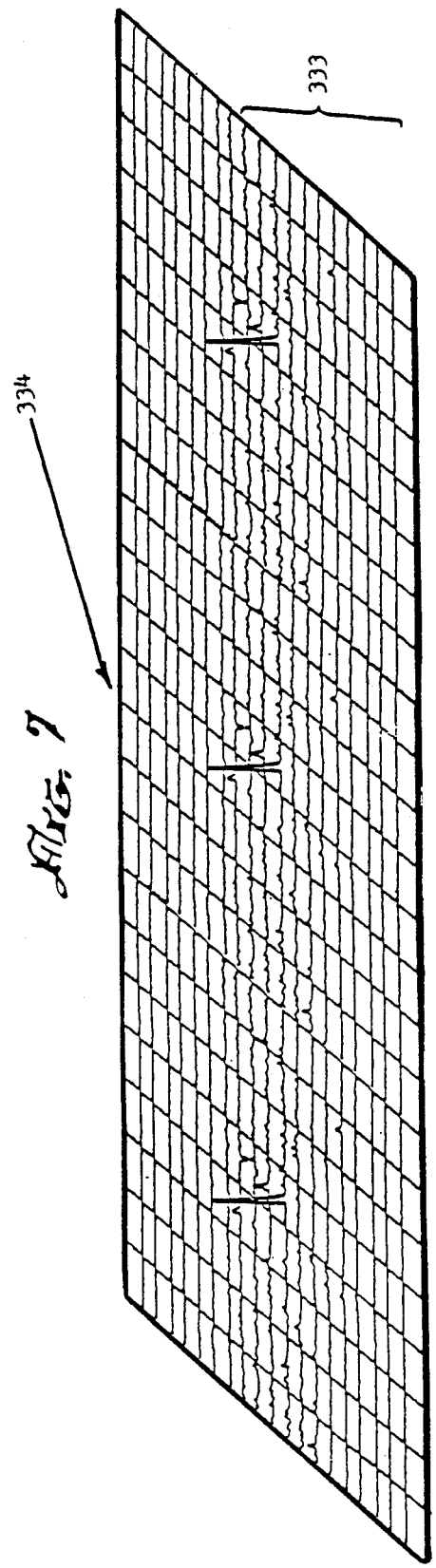

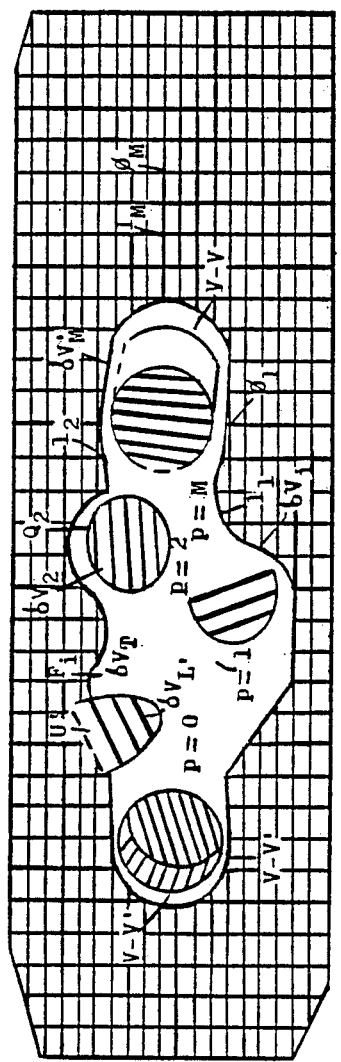

337

338

339

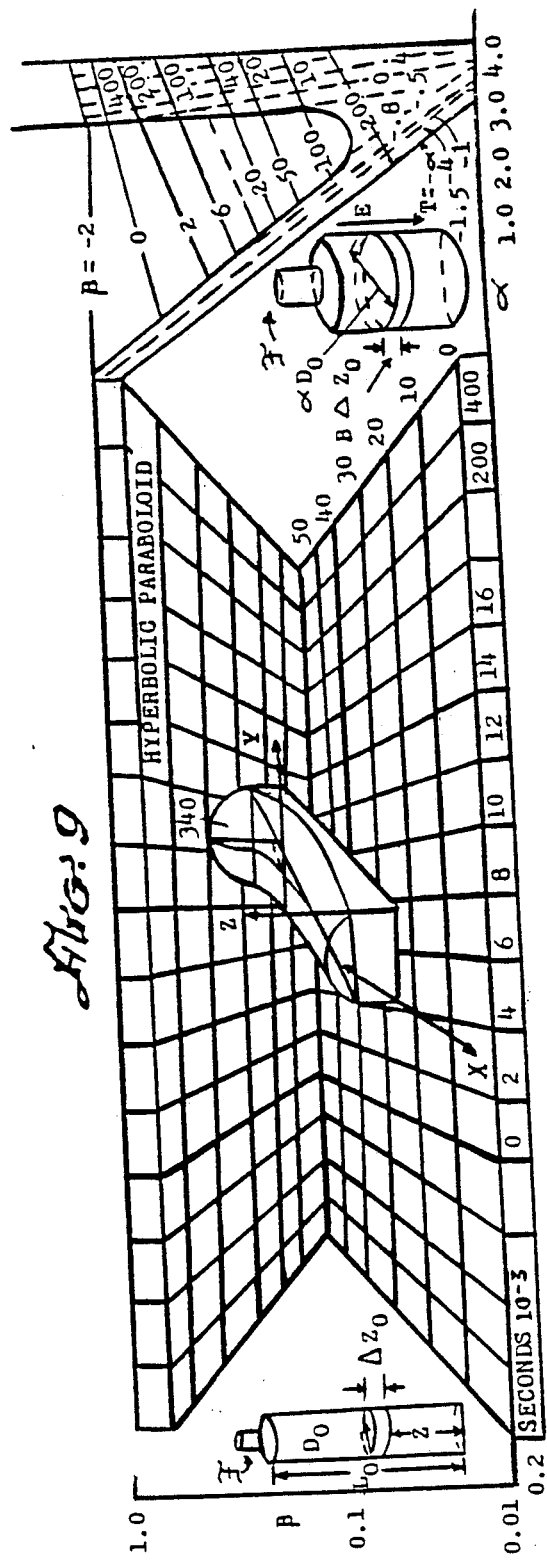

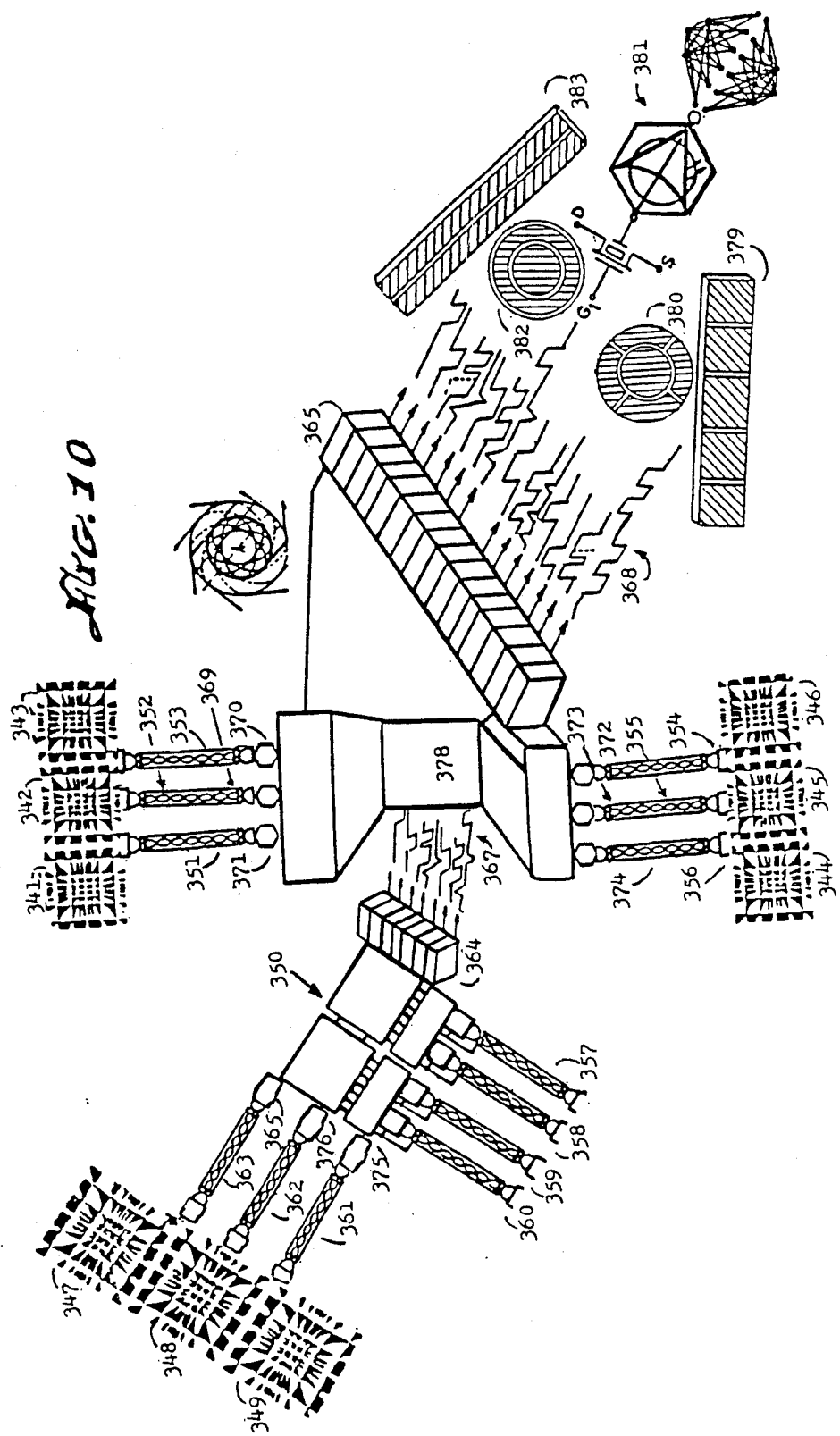

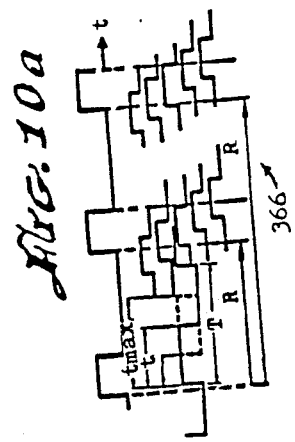

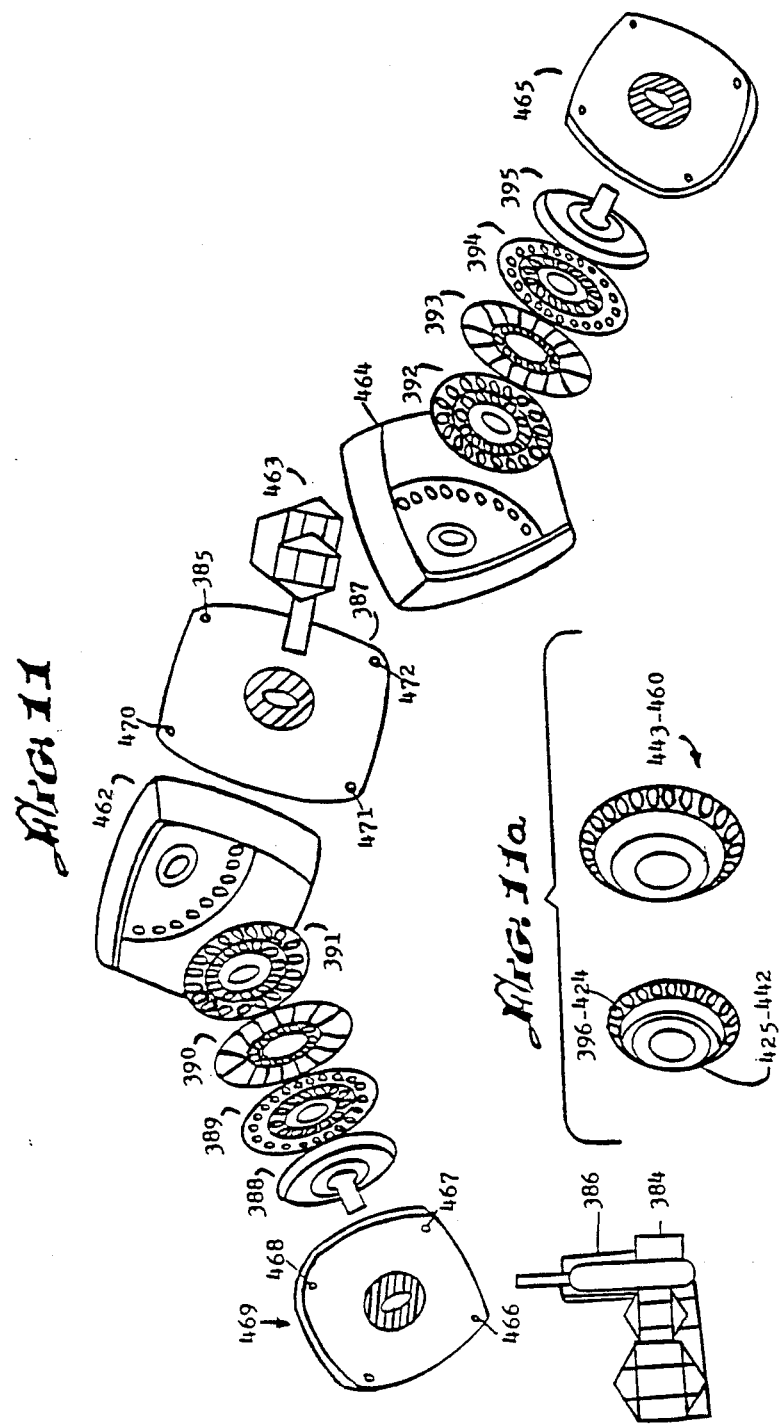

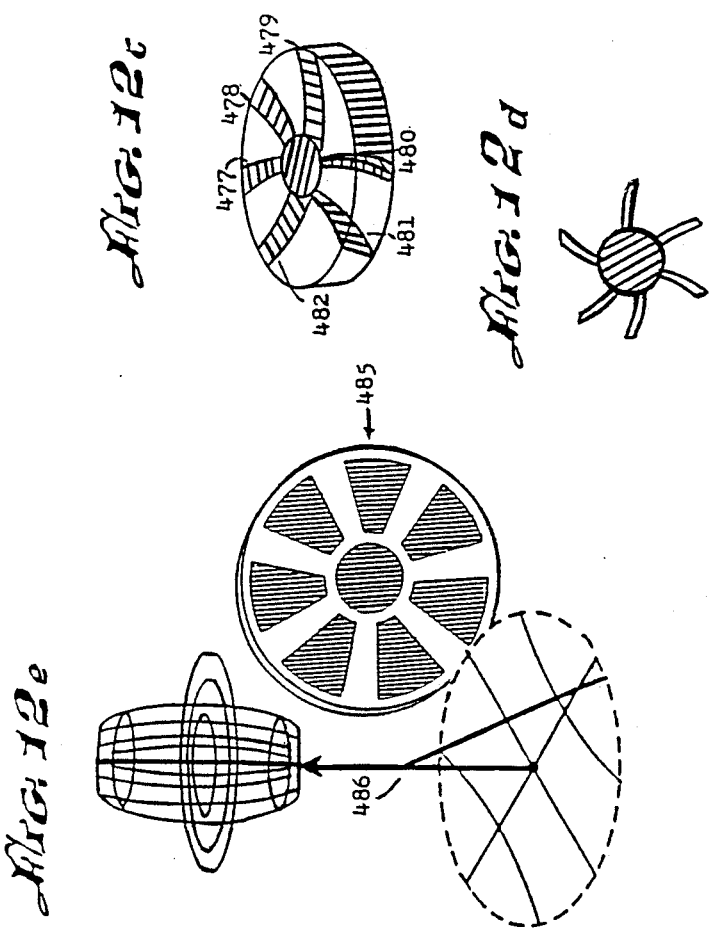

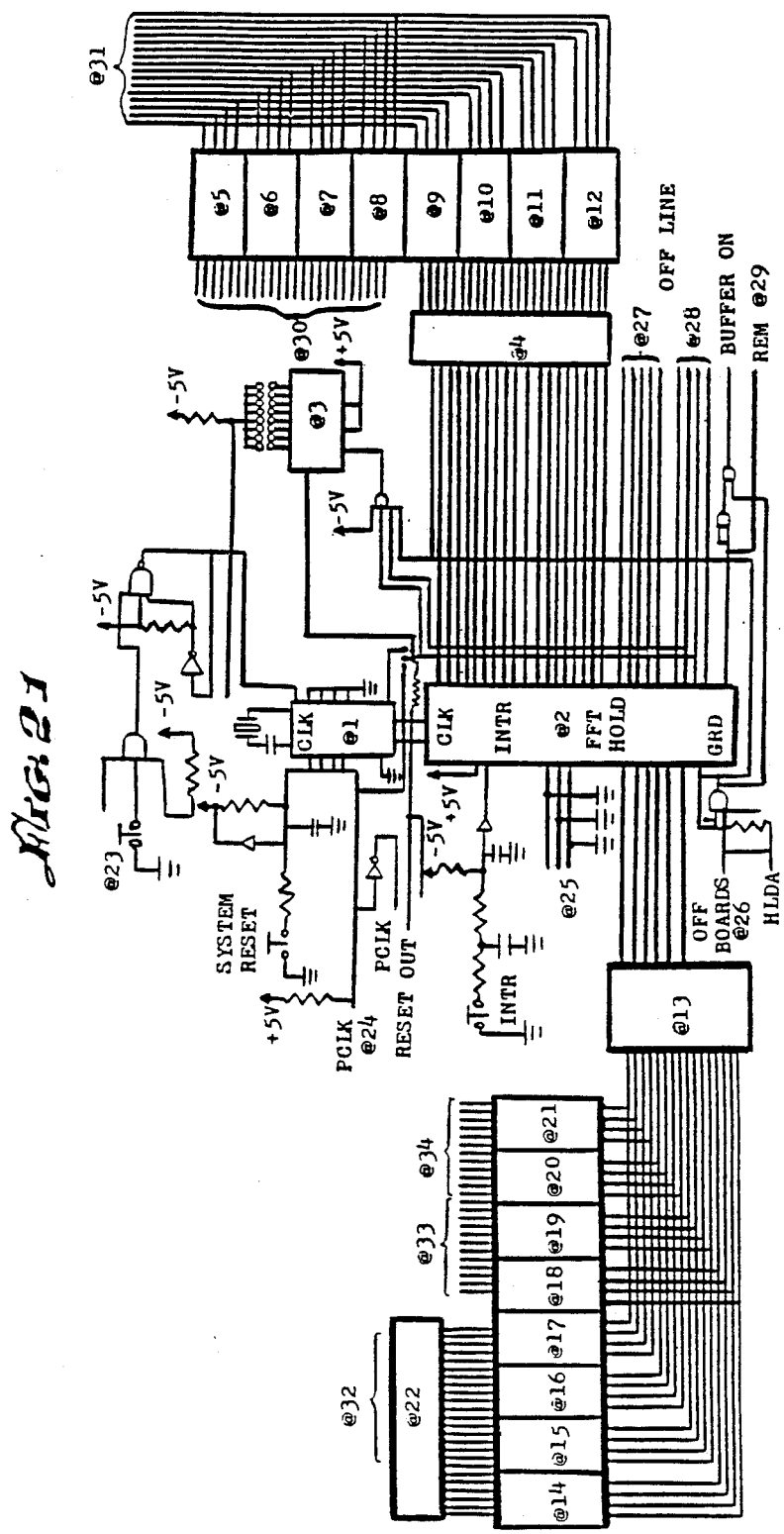

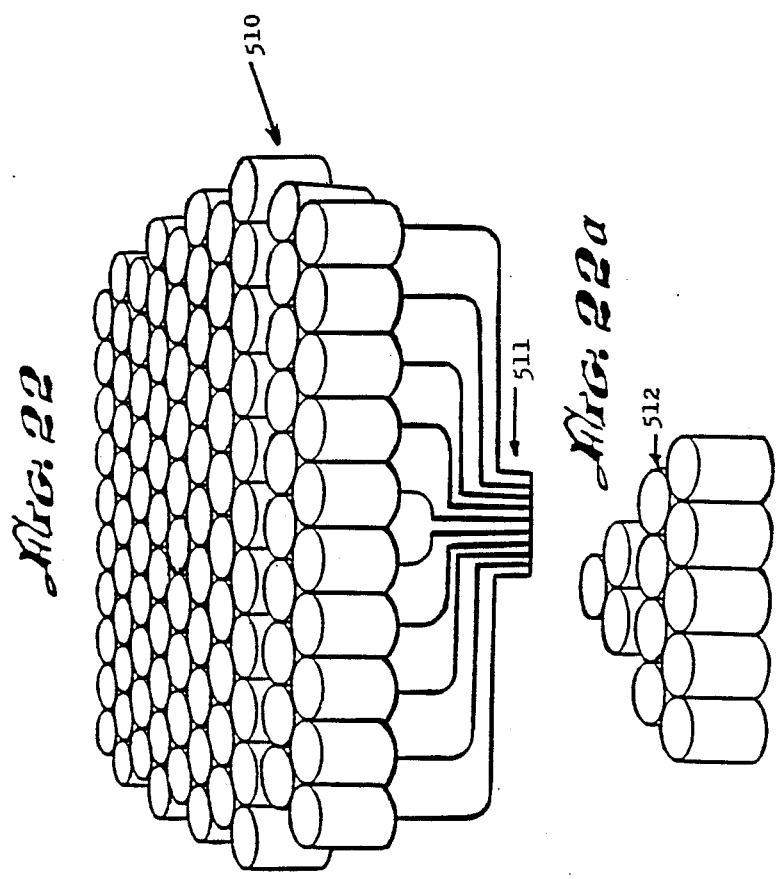

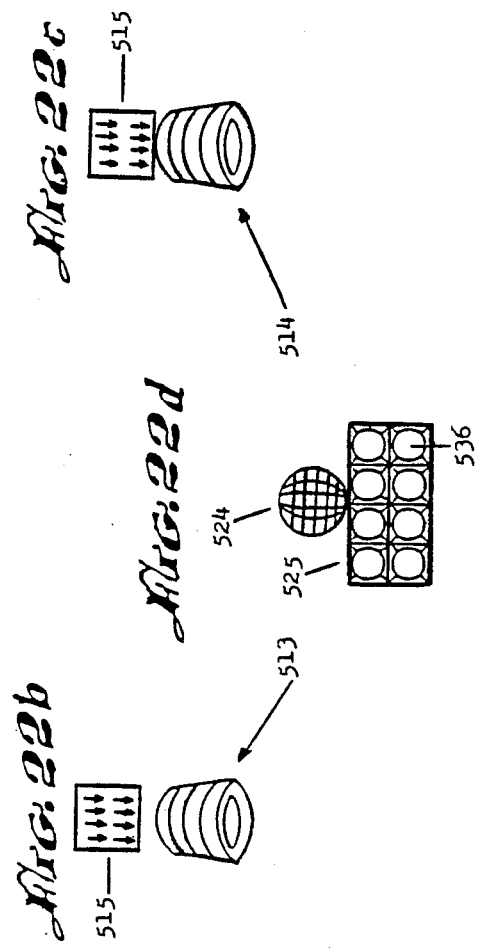

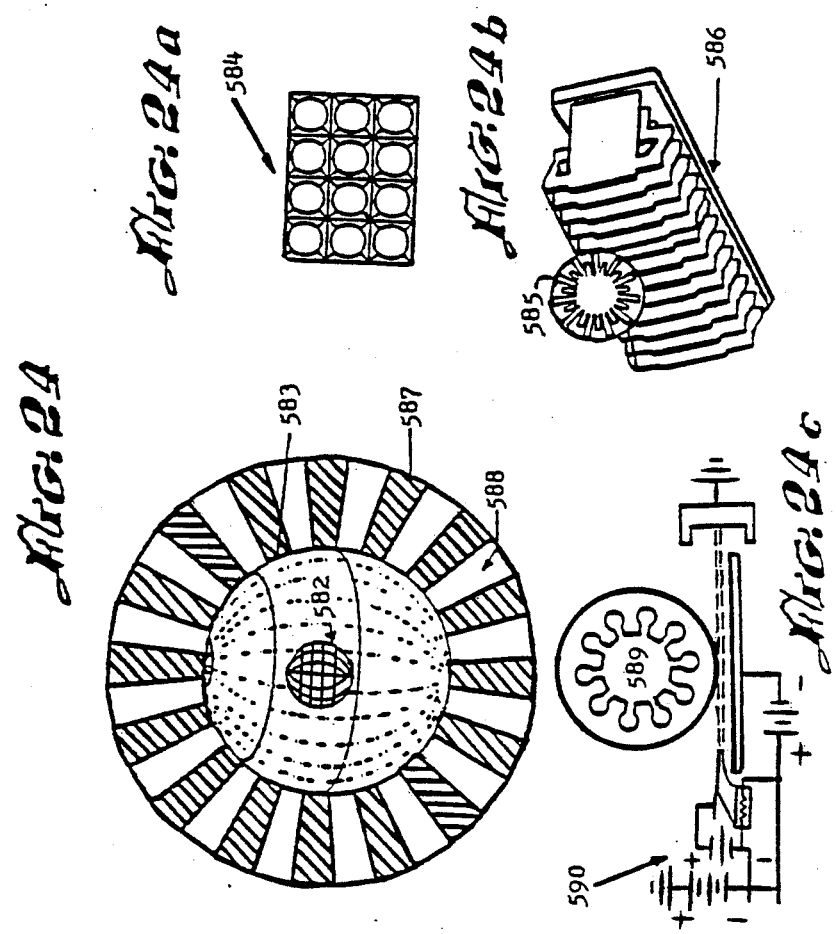

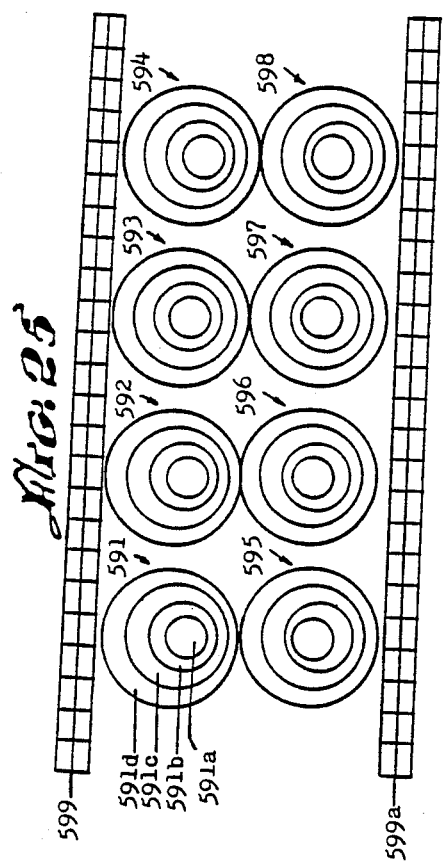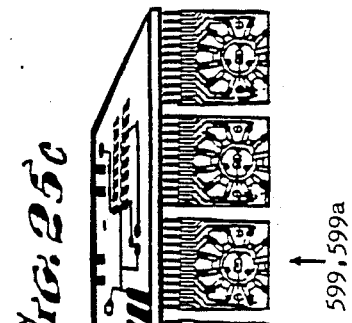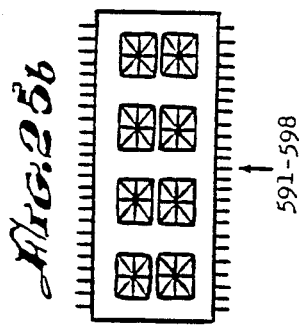

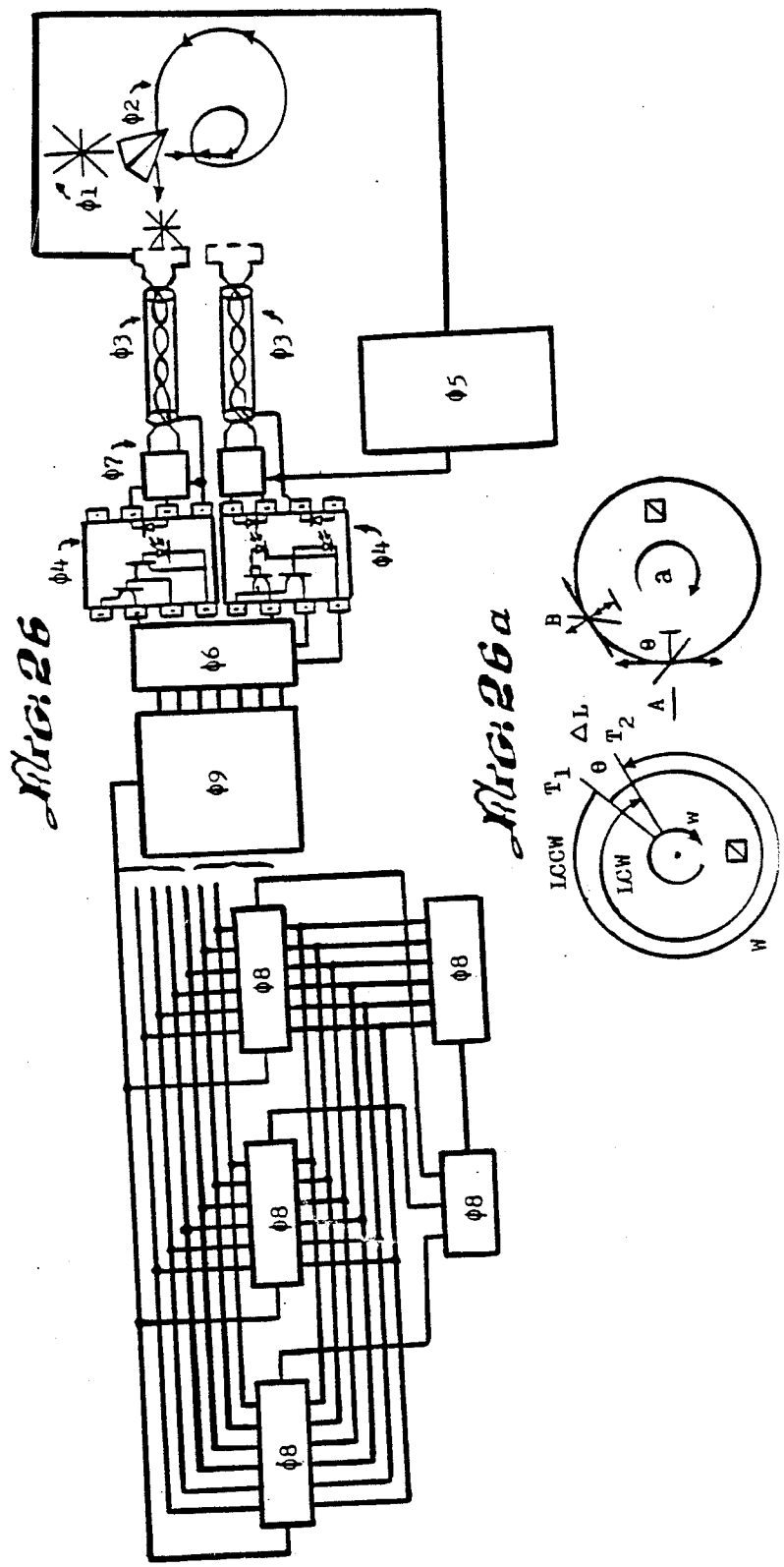

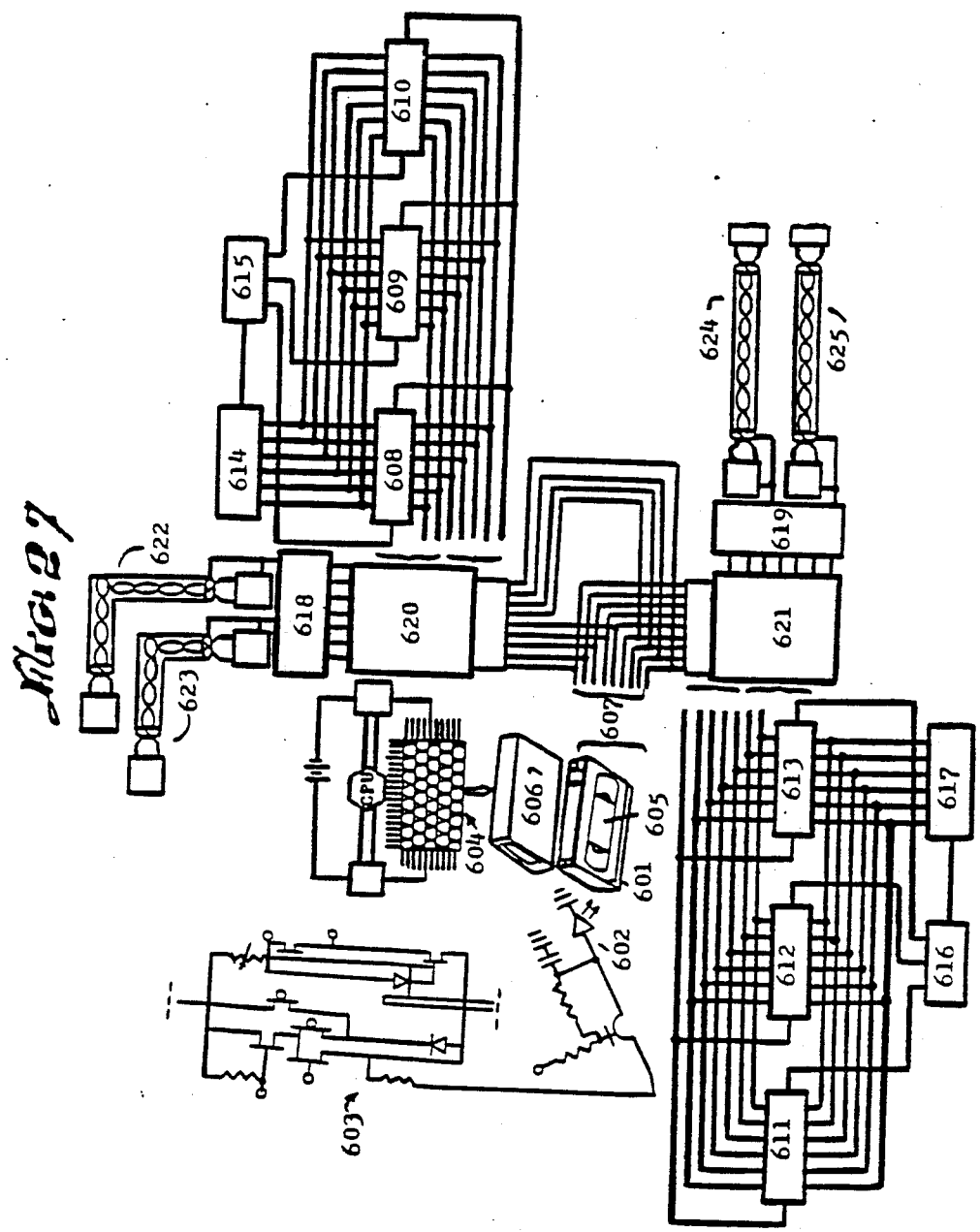

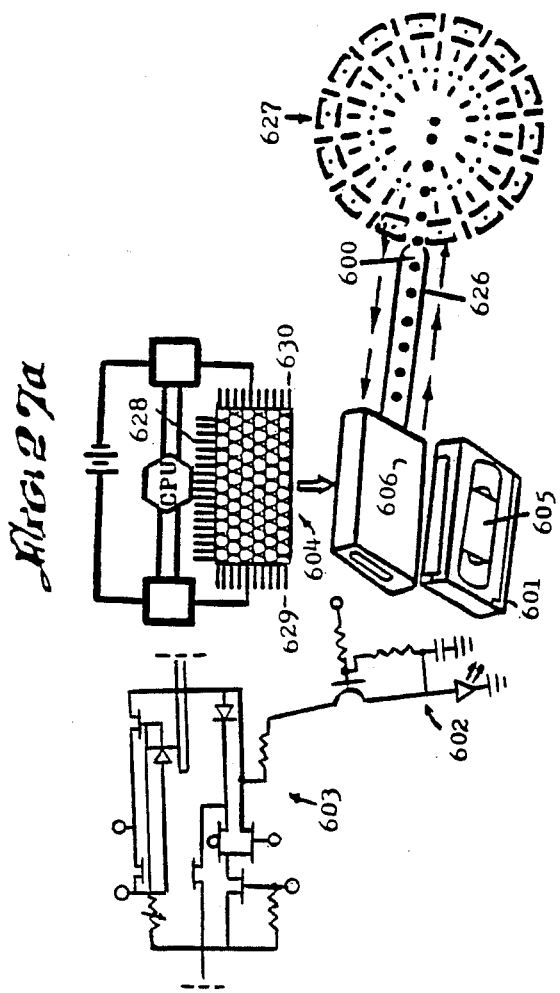

PIEZOELECTRIC MOTIVATOR FOR PROSTHETIC DEVICES

BACKGROUND OF THE INVENTION

1. Field of the Invention

The scope of the invention resides in the construction and application of piezoelectric contrivances in quantitative analytic processes ranging from microelectrophoretic measurement to laser doppler spectroscopy and in enhanced electro-optical signal processing. The enactment of electro-optical devices of precise wavelength and emission frequencies and of oscillation rates which are properly sequenced to provide the electromotive force necessary for the transduction of exact, well coordinated motion of piezoelectric elements is also disclosed. The piezoelectric elements or their equivalent are designed to form prosthetic devices so constructed as to provide specific motions as in the case of artifical limbs or the like, but without the incorporation of electromechanical devices or gears such as electric motors, hydraulic pumps, solenoids and/or other forms of motivation. Also within the field of invention are ancillary devices which support the operation of the mentioned prosthetic devices and are themselves optical sensory devices for measurement of variances of motion, pressure and temperature, or other sensor categories in the case of pH, ion transport and metabolic monitoring. These devices are located both internal and external to the prosthetic unit confines and may be associated with microcomputer arrays for aggregate integration of data for control functions.

2. Description of the Prior Art

Conventional piezoelectric means utilized for continuous wave motion suffer from a significant number of inherent drawbacks, related to their structural composition, disposition, and their response characteristics in the particular usage environment. Piezoelectric design parameters derived from the works of Conragan, Holand, Een Nišse and others based on a static or rigid structural configuration of ceramics, metallics or other suitable materials are are known by those skilled in the art. Conventional piezoelectric elements composed of ceramics, metallics or other suitable solid state materials have a multitude of difficulties when utilized as motivators for prosthetic devices in relation to their elasticity, electrode implacement, structural composition and fatigue due to protracted use and other complications arising from the implementation of power.

Alternate piezoelectric structures formed by polyelectrolytic flexible gels actuated by low currents solve problems dealing with elasticity or structural fatigue, inherent in crystalline means as the rigid configuration of piezoelectric means composed of metallics; but are susceptible to variations in acidity, ionic transport, temperture and related processes. The works of Ohmine and Swislow (U.S.N. grant N00014-80-C-500 supported by the office of Navel Research) along with more recent studies conducted by Fanaka, Sun and Nishio at M.I.T., 1981 through 1983 inclusive, provide the basis for low voltage induction piezoelectric polyacrylamide and polystyrene based Gels. The basic advantages of the aforementioned Gels resides in their resilence, differential stress parameters, absolute response time, and that their contractile elements most closely approximate that of the actomyocin complex indigenous to natural musculature. The disadvantages of Gels aside from the fact that their overall performance can be impeded by differences in pH, temperatures, and osmotic pressure is that their overall power output is presently less than ceramic or metallic piezoelectric means. The accessibility of a microcomputer means to control the output parameters of the piezoelectric gels has not been fully exploited; whereas the microcomputer control for prosthetic devices have been long established for electrical motor driven gear/ratio applications, as established by Solomomow and Lyman on the control of artifical limbs VA Contract V101(134) P-330 and hook opening feedback for below elbow amputee N.I.H. grant G M 21430. Microprocessor based control means have been established by Jarisch, Gustafson, Jain and others under contract PFR 7821670 and are indicative of more recent developments in the implementation of microprocessors in the use of prosthetic devices.

Gel based aggregates in aqueous acetone form toxinogens, when placed in close proximity with a viable organic medium, such as blood borne constituents like endocrine, hormonal, or lymphatic substances in addition to dissolved gases or ions and/or other factors.

All of the aforementioned piezoelectric means are insensitive to evoked potentials, neural humoral secretion, or blood borne chemicals, the effects of metabolism and various enzymatic reactions. Other chemical constituents relating to levels of cholesterol, fatty acids, levels of lactic acid, pyruvic acid, which are byproducts of metabolism, and subtle alterations in the ratios of dissolved gases including but not limited to $CO_2$, $O_2$, or $N_2$ do not effect the normal operation of the said piezoelectric or motorized prosthetic devices established in the prior art Methods of laser doppler spectroscopy, microelectrophoresis and electro-optical digitization and enhancement of signals when embodied within the structure of said piezoelectric structures, which if interfaced with a suitable microcomputer would still lack the sensitivity to effectively repond adequately to the needs of the user. The capacity of a prosthetic device to act in a compensatory fashion to reestablish intrinsic conditions is of great importance in the construction and operatof synthetic organ systems. Analytic operations involving signal processing, digital enhancement, laser spectroscopy, or reletered processes are listed in existing art. Examples of existing art are represented by U.S. Patented works, No. 4,538,613 titled Coherent Radiation Beam Coupler System And Method and related Patents and such works as Programming Format and Apparatus for the Improved Coherent Beam Coupler System and Method Pat. No. 4,589,078, Multiple Amplitude Logistic Kinetmatic Emitter XL-10 Simplified Structural Format Ser. No. /522,331 now abandoned, Exotronics Medical Alert Device, Ser. No. /536,195 now abandoned, and exerpts from A Hybrid Mass Action Driver Device: A Simplified Structural Formal Ser. No. /590,283, now abandoned authored by the inventor hereof. Existing piezoelectric materials capable of providing well coordinated, reliable synchroneous motions, compensating for biochemical and electrophysiological disturbances within the users are virtually non-existent for prosthetic devices providing locomotion. Presently the said prosthetic devices are either to bulky and/or are subject to high fault factors arising from the complexity of the prosthesis. Thus there has been a felt but unfulfilled need for the creation of prosthetic units consisting of operative components formed a renewable form of synthetic musculature responsive to the needs of the user and its system.

SUMMARY OF THE INVENTION

The structural configuration of the piezoelectric contractile elements conforms to and is functionally consistent with the natural design and functions of organic musculature. Each contractile element is composed of an encapsulated flexible trilayer laminate of separate piezoelectric elements embedded in a gelatinous emulsion composed of a suitable material such as, a soft or elastic polymorphic silicon or other equivalent compounds. The piezoelectric constituent layers are composed of a suitable matrix emulsion formed from such commercially available compounds of enveloped hydrolyzed acrylamide in an aqueous solvent, lead zirconate-titanate in a gel suspension, polystyrene gel substrate in a non-aqueous matrix, polymide (Kapton) sheets, Tellurium films deposited on either static or polymorphic/polycrystalline lattices of $BaTiO_3$, and/or any other suitable materials known by those skilled in the art.

Each conducting layer of the piezoelectric means is critically interdisposed between a flexible synthetic non-conducting gelatin of either polymorphic silicon, or polycrystalline graphite and/or any equivalent structural means. The flexible structural design appreciably reduces structural fatigue, fracturing or seepage, which is a necessary consequence of the renewable bonding characteristics of the gelatinous material. Solid laminated metallic ribbons of the of the above mentioned materials, such as lead zirconate-titanate, Cadmium Sulfide laminated films or other metallic crystalline laminates, or certain polymorphic compounds, have a tendency to undergo separation, or develop small fractures, or undergo other effects of structural fatigue due to wear with continuous use over a finite protracted period of time; whereas equivalent gelatins have a far greater longevity, a greatly optimum operating maximum limit and power efficiency than ribbon laminates of the same said materials. Photovoltaic piezoelectric version of the aforementioned substances utilizing direct laser beam coupling rather than electro-optical transduction were constructed, but lacked the sensitivity and operative power output of their said electro-optical equivalents. The piezoelectric units each are structured in the form of an elongated oblique sheet encapsulated or packaged in its own separate individual non-conducting elastic sheath isolating each separate contractile element both physically and electronically from every other equivalent unit. Each and every separate or independent contractile unit is innervated* with one or more arrays of bidirectional fiber optical bundles. The arrays are interfaced at both termines by common junctions, which are provided with separate and distinct electro-optical power converters, wherein the digitized optical inputs are transformed into their digitized electronic power equivalents. The electronic power equivalents or digitized electric signals are further transduced into physical motion or mechanical force, in a manner consistent with the well defined operations of all piezoelectric means.

Innervated by definition means the insertion and impingement of signal or impulse conducting means into substances or elements capable of being actuated by said conducting means.

The optical system drivers for the electro-optical converters are provided by a series of miniature high efficiency laser means whose generated coherent signals pass along the electro-optical conduits, arrays or equivalent structures. The optical arrays or conduits are covered with a reflective shield in order to prevent losses in the transmission power or incurred interference from other systems.

Each contractile means is graduated or tapers gradually to terminate at points which form end plates. The end plates structures are provided with woven tendrils formed from commercially available synthetic fibers, which are arranged further in the form of taut elastic cables. The tendrils or strands consist of extruded filaments of synthetic graphite, polymorphic silicon or some other equivalent material; which is affixed, epoxylated or fused to points of attachment. The points of attachment consist of the piezoelectric means proper, structural support means such as rotating joints, valvular means, or assemblages of synthetic skeletions formed from either ceramic composites or extruded plastics or other suitable structures. The exact methods of attachment in every case range from adhesive bonding, thermal bonding, the insertion of pins, rivets, screws, or other suitable procedures well known by those skilled in the art.

Each adjutant series or group of elongated piezoelectric contractile elements operate collectively to act as extensors or flexors and provide motions such as, peristaltic contractions, pronation, or subposition. A necessary consequence of the so-called adjutant series, or opposing contractile units are embodied within the antagonistic protagonistic piezoelectric groups. The piezoelectric element either bends some discrete distance upon application of voltage and elongates or stiffens, when the voltage is removed said element. Piezoelectric units are therefore collectively arranged in groups providing opposing motions. The strength, speed, direction of force each piezoelectric unit contributes is directly proportional to the diameter, the number of units actuated and the strength or field intensity of the electromagnetic fields applied to the aforesaid piezoelectric means per temporal interval therein.

Additional means of locomotion are provided in the event of a systems failure, or in the event that further support measures for the aforementioned piezoelectric means are needed. A unique and novel variation of a gearless arcless piezoelectric means has been devised to provide the necessary torque to drive a suspended drive shaft. A series of mutually exclusive piezoelectric elements are arranged in a circular array around the said drive shaft. Each operative piezoelectric element is set angularly providing a thrusting motion, when energized, to a complementary indented angular portion of the drive shaft means. The entire complement of the piezoelectric means engages the respective indented portion of the shaft in a sequential manner, which is conducive to the rotation of the said shaft means. The tip or plunger of the angular piezoelectric means is composed of a long wearing synthetic polymer as the indented portion of the shaft. The drive shaft itself is composed of a composite ceramic material which may or may not engage a gearless low-friction variable disc means providing rotation to artificial joints and equivalent structures. The lack of arcing associated with the normal operation of conventional electric motors provides a relatively quiescent, high efficiency, reliable, electronically stable mechanism with regards to interference hereto unachievable by present equivalent electric motors or solenoid means.

Digitized signals received from laser emitters provides the necessary electromotive force to animate the synthetic piezoelectric musculature. Suitable power sources for the said laser means are contained either within the framework of the prosthetic device proper or the exterior of the said device. Sources of power are presently available from commerically obtainable rechargable nickel cadmium or lithium batteries for limited operations to miniature nuclear power sources for extended operations. Other potential energy sources external to the prosthetic device are derived from the users own metabolic processes are initiated by the physical transduction of motion generated from the operations of other muscular elements as collective flow valves based on circulation provided by the users heart. Other forms of energy sources range from radiofrequency impulses feed by a mobile transmitter to solar energy means; however these exotic means and energy derived from metabolism have certain inherent difficulties.

The scope of the invention embodies the construction and subsequent implementation of two classes of piezoelectric motivator means or contractile elements which generate the necessary electro motive force required to drive an extensive number of prosthetic devices. The prosthetic devices include but are not limited to artifical limbs. The first class of piezoelectric motivators consist of piezoelectric Gels; whereas the second class of motivators consist of polyelectrolytic Gels. The piezolectric and polyelectrolytic Gels are encapsulated within a elastic polymorphic/polycrystalline membrane. The apparent contractile action of said polyelectrolytic Gels is instituted by a shift in the phase transition within materials forming the motivator means rather than being initiated by electromechanical transduction causing the piezoelectric material to undergo structural distortion, bending, or related processes. The aforementioned polyelectrolytic Gel, additionally undergoes volumetric changes, when subjected to alteration in the colligative properties associated with said polyelectrolyte material and solution in which it is immersed and subtle changes in applied electrical charges, pH and related parameters. Said volumetric changes initiated by the polyelectrolytic are accompanied by the aggregation and breakdown of chemical chains and/or complexes which enter and exit from the aforementioned solution.

Chemical complexes necessary for volumetric contraction are recovered by active reabsorption through laser actuated synthetic membranes embodied within the polyelectrolytic gel element. Said synthetic membranes structures actively reabsorb chemical aggregates by selectively altering the permeabilty of the membrane structures. The properties of the aforementioned synthetic membrane structures are collectively changed by altering the frequency, wavelength, duration and other properties of digitized optical emissions emanating from miniature laser sources. The reassimilation or reabsorption of expended chemicals derived from the operation of the aforementioned polyelectrolytic elements provide a continuous renewable source of materials necessary for the operation of said piezoelectric structure. A short transitory or latency period is necessary; wherein reabsorption and chemical recombency is initiated in for said polyelectrolytic elements, which corresponds to the recovery period of organic muscles in regards to the ATP~ADP ionic reactivation of the actomyocin complexes.

Additionally, embodied within the invention are networks of sensory elements monitoring acceleration, detecting pressure, temperature and variances in electrophysiological biochemical processes; which includes but is not limited to the measurement of ion concentration, osmolality, neurohumoral substances, the accumulation of metabolites and blood gas tension of $CO_2$, $O_2$, $N_2$ or other substances. Responsive electric conduction of and/or other impulses from neuronal templates, physiological structures. The sensory apparatus are interphased with feedback loops that are under the control of CPU, which transmits control signals to said piezoelectric structures. The aforementioned piezoelectric structures operate as synthetic analogs of living muscle tissue. Polyelectrolyte or polyelectrolytic piezoelectric Gels, as disclosed in the specifications more closely approximate the structure and operation of organic muscle tissue than any synthetic structures presently known by those skilled in the art.

BRIEF DESCRIPTION OF THE DRAWINGS

FIGS. 1, 1a, 1b, 1c, 1d and 1e are brief pictorial descriptions providing a detailed representation of an operative array of piezoelectric elements affixed to supportive means;

FIGS. 2d and 2e are pictorial representations of four separate and distinct piezoelectric elements and their respective electrode configuration;

FIGS. 2f, 2g and 2h are indicative of pictorial perspective views of four piezoelectric means which are undergoing electrical transduction;

FIGS. 3, 3a and 3b are perspective views of a single trilayer piezoelectric element grouping undergoing recursive voltage reversal;

FIG. 6 describes in a concise diagrammatic fashion the arrangement of laser drivers, field generators, electric optical converters, or other structures embodied within the polyelectrolytic piezoelectric Gel means;

FIGS. 6c, 6d are illustrative perspective views of an artificial membrane which is responsible for the release of specific ions and/or other molecular or chemical constituents.

FIG. 6f and 6g are diagrammatic representations of the artifical membrane undergoing photonic excitation;

FIG. 6h illustrates pictorially the process and means wherein solutes acids, bases, or other substances undergo reabsorption, reformation and dispersal;

FIG. 6i describes in a brief schematic manner the disposition of two equivalent adjacent, differentially permeable release reservoirs;

FIG. 7 is a concise graphical representation of an evoked potential propagated along the conducting axes of a piezoelectric element;

FIG. 7a describes in an illustrative manner the wave motion of a three dimensional piezoelectric structure of an arbitrary shape;

FIG. 9 describes graphicaly the phenomenon of phase transition associated with polyelectrolytic Gels taken in real time;

FIGS. 10, 10a are concise, partial schematical block diagram representations which illustrate in part the electro-optical signal generators and driver means utilized to power solid state and polyelectrolytic piezoelectric means;

FIGS. 11, 11a disclose in part exploded pictorial representations illustrating a robotic limb means;

FIGS. 12, 12a, 12b, 12c, 12d and 12e entail perspective views of a single piezoelectric drive engine;

FIG. 20 is illustrative of a simplified block diagram perspective, which denotes only one of the equivalent microcomputer array processor elements deposited on a single VLSI card responsible for motivation of several prosthetic units which are responsible for identifying chemical constituents of the user, evoked potentials and the like;

FIG. 21 describes in part only one of several timing oscillator circuits or sequencer means deployed in the prosthetic devices;

FIGS. 22, 22a, 22b, 22c, 22d, 22e, and 22f, represent in part detailed sectioned views of a single independent cushion type of pressure transducer;

FIGS. 24, 24a, 24b and 24c entail simplified pictorial views of a gravity dependent charged droplet proprioceptor means;

FIGS. 25, 25a, 25b and 25c are concise pictorial views of a portion of a continuous liquid crystal linear thermal sensing device;

FIGS. 26, 26a disclose in concise block diagram forms a simplified fiber optical laser gyroscopic device;

FIG. 27 describes in brief a partial block diagram of a single continuous flow microcuvette analyzer complex;

FIG. 27a entails the means by which bodily fluids of the user are obtained for analysis and the subsequent discharge of said fluids upon completion of analysis.

DETAILED DESCRIPTION OF THE INVENTION

Figure 1A:
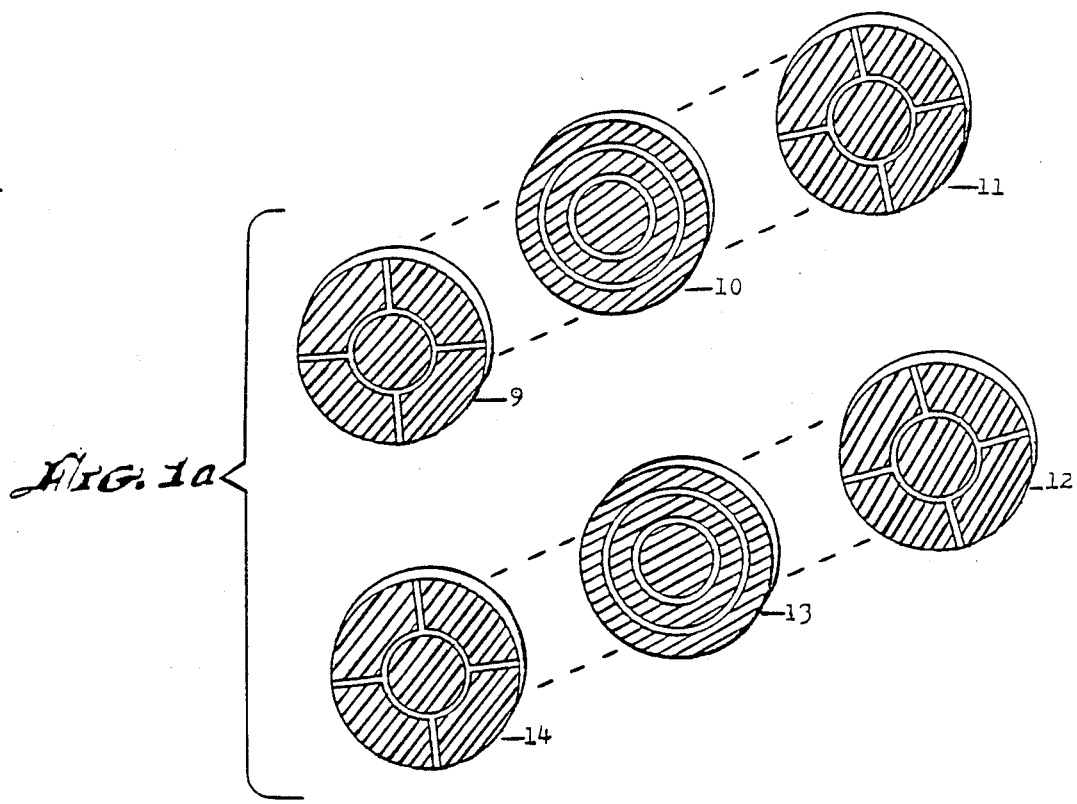
Figure 1B:
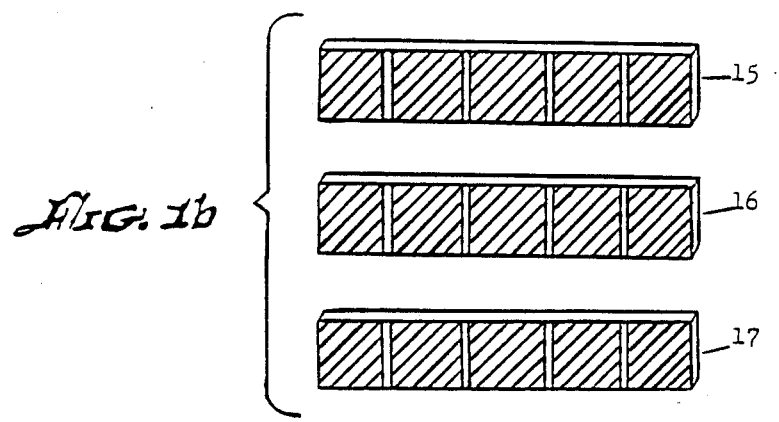
Figure 1D:
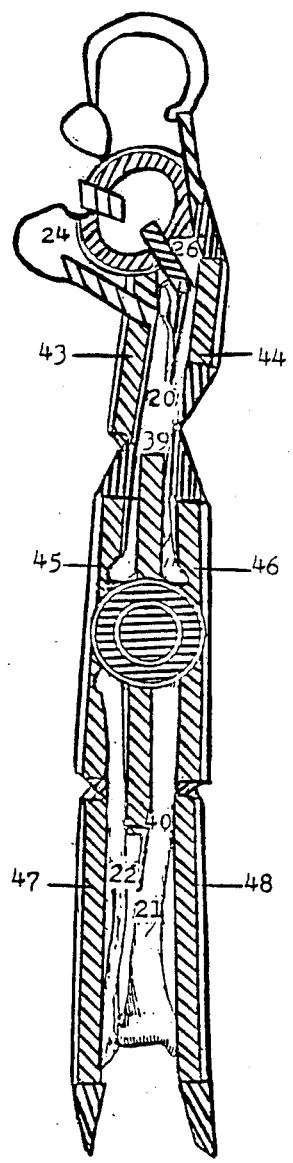
Figure 1E:
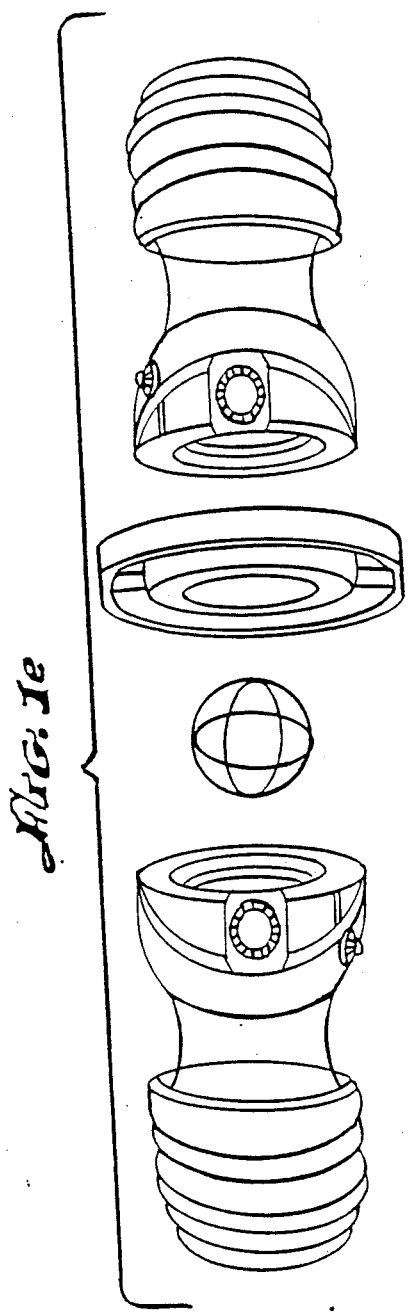

The piezoelectric motivator means for prosthetic devices as applied for in this patent disclosure are divided into two broad classes consisting of encapsulated solid state piezoelectric Gels and encapsulated polyelectrolytic Gels. Solid state gelatinous tri-layers of conductors and or semiconductors are encapsulated within a polymorphic/polycrystalline flexible matrix or membrane, as indicated in part by FIGS. 1, 2b and 3. Polyelectrolytic Gels are similarly encapsulated in elastic membranes and are capable of undergoing discrete volumetric changes with alterations in the collegative properties of the Gel due to subtle variations in osmality, molarity, or minute variance in extrinsic voltage, pH and various cofactors, as specified in part by FIGS. 2, 2a and including FIGS. 4, 5. Polyelectrolytic Gels operate in a gross observable manner more closely approximating the contractile actions of organic musculature when structured with physical diameters in the micrometer range and having a mean response/recovery interval in the millisecond range ($<100$ to $400+$ miliseconds). The contractile action of polyelectrolytic Gels are accomplished via a shift in the phase transition process rather than undergoing physical distortion by an electromechanical transduction process, as ascribed to the aforementioned solid state piezoelectric means. The basic limits of polyelectrolytic Gels relate to the relative deficiencies in speed, torque and the mechanical force generated per volume weight of a single unit; when compared to solid state piezoelectric encapsulated gelatinous ribbons of barium zinc titanate, lead titanate, or similar such materials generate in excess of 60 (sixty) percent more mechanical force than polyelectrolytic Gels. Polyelectrolytic Gels appear to be more acclimated to undergo continuous use, as in the execution of peristaltic motions and/or numerous extended, or repetitive operations being far less susceptible to fatigue, reducing fractures, or matrix distortion and other degenerative events indicative of more rigid crystalline piezoelectric means.

FIGS. 1, 1a, 1b, 1c, 1d, and 1e describe in brief concise pictorial representations of an operative array of piezoelectric elements affixed to their respective support means. Numerals 1, 2, and 3, 4 of FIG. 1 describe the external structural support elements or adaptor means, the single spherical bivot and the rotational frame for articulating joint means 5. Elements 6 through 6e are inlet structures which supply articulating joint means 5 with a low friction lubricant derived from a renewable synthetic graphite surfactant, 7, which is supplied passively by reservoir 8. Means 5 is embedded into femur means numbers 18 and 20, as well as, the pubis region described by number 19. Numeral 23 denotes an articulating joint means equivalent to that of number 5, but located in the patellar region. The patellar piezoelectric motivator, numeral 33, consists of a multiple electrode trilayer, described by units 9 through 14, which are composed of a suitable material, such as, lead or zinc titanate, or other more suitable materials. Numerals 15, 16 and 17 depict the electrode configuration of a typical ribbon piezoelectric means consistant with structures 24 through 32, which are equivalent to elements 38,39,42 and 43. Structures 20,21 and 22 represent premolded extruded structures composed of tubular composites of ceramic, graphite and nylon; which are casted in the shape of a femur, fibula and tibia, respectively. Structures 24, 24a and 24b and 24c are radial piezoelectric structures utilized to rotate means 5. Points of attachment or insertion for the various piezoelectric units for leg, knee and the foot region are denoted in part by operative extensor, or flexor, elements 39 through 42. Motivator means consisting of cables formed from woven threads of flexible nylon, polymorphic silicon and/or graphite are designated by elements 34 through 38a. Additional extensor and flexors are obversely placed and indicated in part by numerals 43 through 47.

Figure 2:
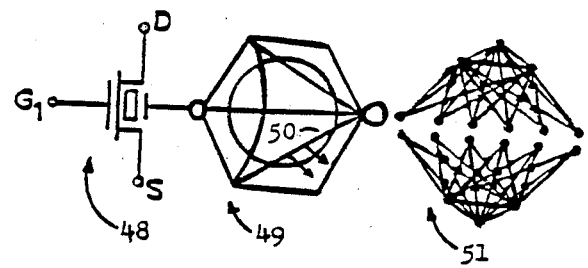
FIG. 2 denotes a schematic representation of a single typical polyelectrolyte encapsulated piezoelectric element.

FIG. 2 denotes a schematic representation of a single discrete polyelectrolyte encapsulated piezoelectric element formed from a suitable medium, such as, polyacrylamide Gels in aqueous mediums, polystyrene Gels in a non-aqueous solution, or other suitable compounds. A multiphased solid state piezoelectric attachment, described by numeral 48 is associated with a complex chemical configuration, which is indicated by ring structure 49. The ring configuration has embedded into its structure a series of electro-optical means, which are designated by emitter structure 50. The entire assemblage of component numbers 48, 49 and 50 are further associated with a reversible phase transition segment, indicated by number 51, which performs various contractile operations with variations, ionic concentration, osmotic disposition, pH, voltage and related processes.

Figure 2A:
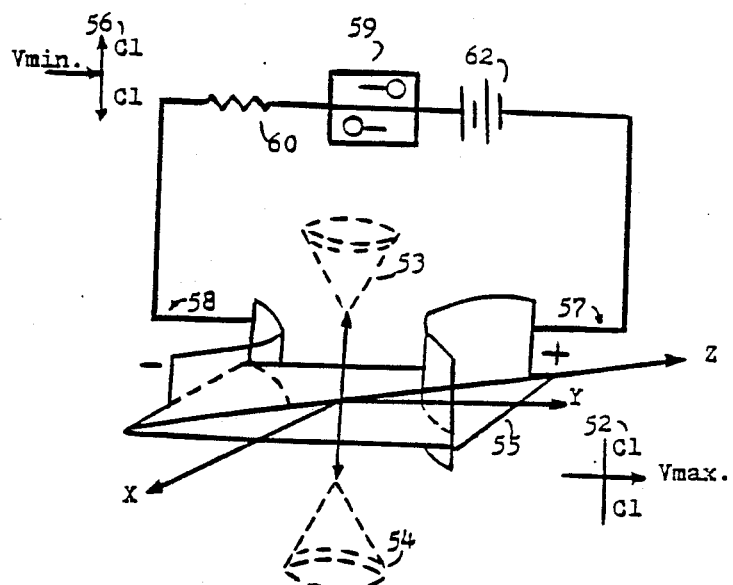
FIG. 2a describes in an illustrative manner the geometric motion of a single polyelectrolyte piezoelectric Gel element.

FIG. 2a describes in an illustrative manner the geometric motion of a single polyelectrolyte piezoelectric Gel contractile element. Electromagnetic field closure providing a closed circuit is signified by structure 52, which elicits the contraction of elements 53 and 54 towards the origin of the plane designated by numeral 55. An open circuit allows reversible expansion of elements 53 54 away from the origin of element 55, which is described by numeral 56 The cathode and anode means are depicted by numerals 57 and 58; whereas the remainder of the simplified circuit is indicated by number 59. A simple low power source provided within the circuit is denoted by numeral 60, a resistive element is represented by number 61, and an optical switching element is exemplified by symbol 62.

Figures 2B, 2C:
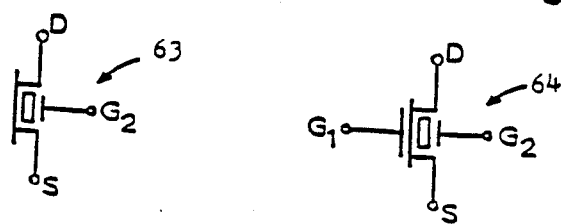
FIGS. 2b and 2c are schematic representations of two solid state piezoelectric elements.
Figure 4E:
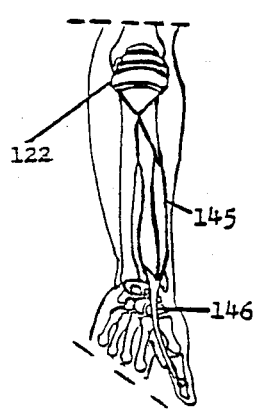
FIGS. 4, 4a, 4b, 4c, 4d, 4e, 4f, 4g and 4a are perspective views of antagonist and protagonist polyelectrolytic embodiments of Gels encapsulated and affixed to support structures.
Figure 4F:
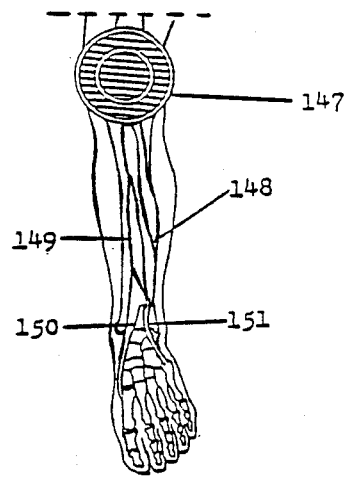
Figure 4G:
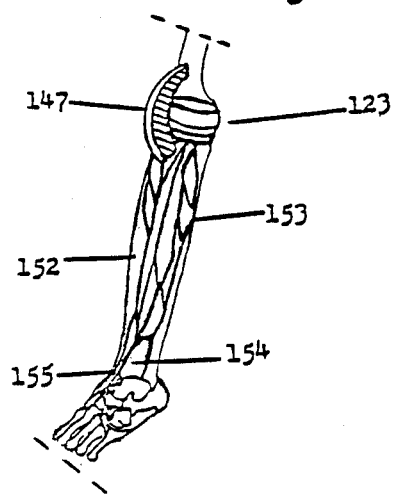
Figure 4H:
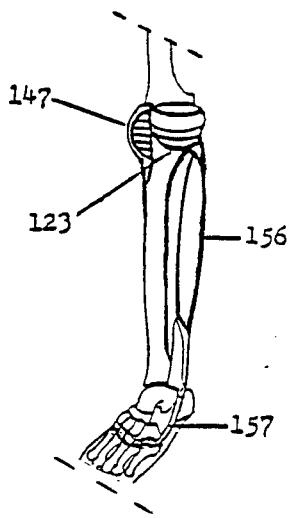

FIGS. 2b and 2d are schematic representations of two typical solid state piezoelectric elements designated by numerals 63, 64 respectively.

FIGS. 2d and 2e are pictorial representations of four separate and distinct piezoelectric elements and their respective electrode configurations. Each structure of the four aforementioned structures have embedded in its design an array of electrodes. The circular piezoelectric disc structures are described by elements 65, 66, while the rectangular ribbon electrodes are designated by units 67, 68.

FIGS. 2f, 2g and 2h are indicative of a pictorial perspective views of four separate and distinct piezoelectric elements conducting current or otherwise completing a circuit, and in so doing transducing electrical energy into a mechanical force. The directions of mechanical force are indicated by arrows emitted from each piezoelectric means and incurred by an array of electrodes and/or current sources, which are designated by the symbol $\phi$ or in some instances denoted by hatched configuration, as signified by elements, 72. Each said piezoelectric element is assigned a numeric value, as denoted by numeral 69, 70. 71 and 72.

FIGS. 3, 3a and 3b are perspective views of a single trilayer piezoelectric element grouping undergoing recursive voltage reversal from an initial static, or deactivated state, to a voltage actuated state. Nine structure are depicted in an illustrative manner and each is assigned a separate numeric value denoted by numbers 73 through 81. The gelatinous trilayers are formed from a suitable piezoelectric material such as, lead or zinc titanate, or variations thereof, or any similar such materials capable of undergoing mechanical transduction. Here the voltage bias is reversible and the direction of physical distortion can be altered with the subsequent reversal of field polarity. Numerals 76, 77 and 78 are indicative of the same said piezoelectric elements in an electrically neutral, or unbiased state. Once a forward biased is exacted the piezoelectric means bend in a forward direction, as indicated by numbered structures 73, 74 and 75. If a reversal of polarity is exacted the bind of the piezoelectric means occurs in the obverse or opposite direction, as indicated by numerals 79, 80 and 81.

FIGS. 4, 4a, 4b, 4c, and 4d are perspective views of an antagonist and protagonist polyelectrolyte encapsulated piezoelectric Gel elements, are fused, riveted, affixed by an adhesive, or otherwise attached to structures in a specific manner conductive to the motivation of certain articulating joint means. The nomenclature of the synthetic structures correspond to their living counterparts. An artifical hand means described by numeral 82 is composed of structural support elements 83 through 101. Each artifical structural phallange, or finger is equipped with either three or four articulating joint means, represented in part by elements 102 through 116. An additional rotary means is provided for the synthetic carpal structures, which are designated by numerals 117, 118, 119 and 120. Numerals 121 through 123 exact equivalent articulating structures and units 102 through 116 are all identical to the articulating joint means, as described by numeral 82. The polyelectrolyte piezoelectric motivator means for the artifical hand are designated in part by elements 124 through 132. A radial motivator means is indicated by numeral 132, which motivates flexor cable means 134 through 137. Motivator 138 operates extensor cables 139 through 142, whereas motivator means 143 powers extensor means 144, as described in FIGS. 4a to 4d.

FIGS. 4e to 4h describe in an illustrative manner the geometric motion of a single radial motivator, 145 powers longitudinal exactor means 146. Numerals 147, 148 and 149 designate a radial patellar, a tibular and a fibular motivator means. Motivators 148 and 149 power extensor means 150, and 151. The patellar articulating joint means is assigned the numeric value 123. Tibular and gastrocnemius motivators 152, 153 motivate or drive extensors 154, 155, whereas motivator 156 powers cable means 157.

Figure 5:
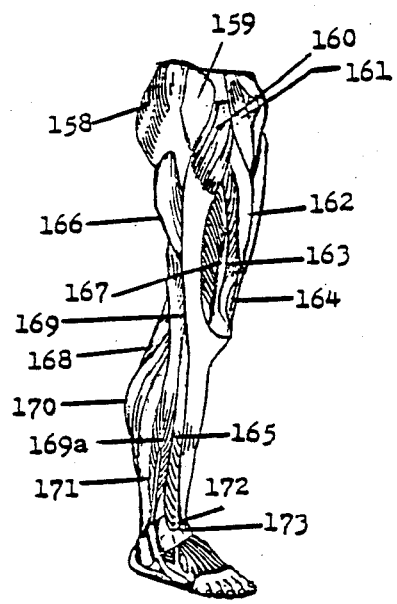
FIGS. 5 through 5e are a concise pictorial representation of synthetic polyelectrolytic embodiments of prosthetic appendages.
Figure 5A:
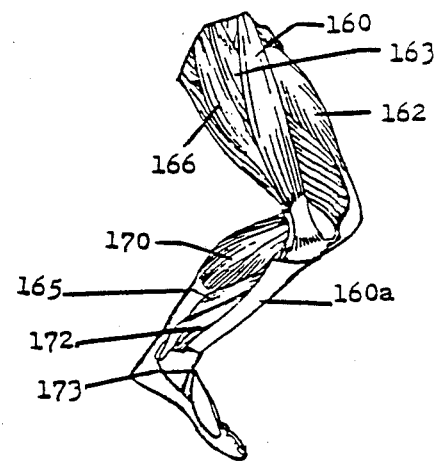
Figure 5B:
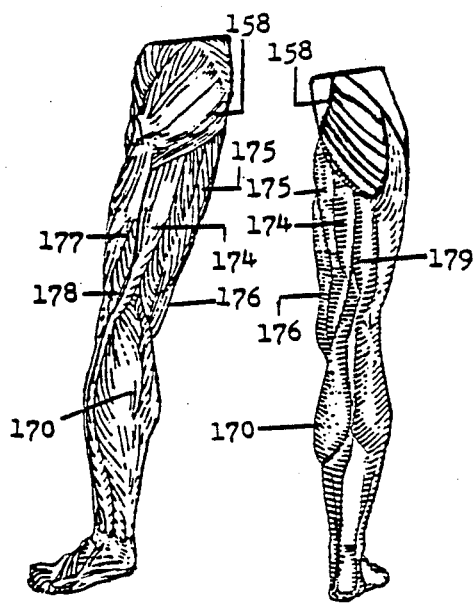

FIGS. 5 to 5e are a concise pictorial representation of the anatomical disposition of the piezoelectric polyelectrolytic Gel groups forming the bases of a protagonist-/antagonist configuration. The similarity between the nomeclature assigned to synthetic groupings corresponds to those of the natural system analogs, which occupy the same regions and perform the equivalent functions. Numerals 158, 159, 159a and 160 correspond to the gluteus maximus, a longitudinal femur adductor and the tensor fasciae latae means. Elements 162 through 164 denote the motivator corresponding to the quadrieps femoris, whereas unit 161 describes a sartorius motivator means. Numeral 165 is assigned to the soleus motivator and units 166 through 169 are indicative of lateral extensor and lateral flexor means. The gastrocnemius majoralis and peronus are represented by elements 170 and 171. The soluus elements are described by number 172 and the annular cable proper corresponds to element 173. Regions of the biceps femoris, vastus lateralis and femoral extensors are designated by numerals 174, 175 and 176. The femoral adductor; adductor not shown, and associated cable means are indicated by numerals 177, 178 and 179, respectively. The upper limb portion prosthetic units are described in part by elements 180 through 190. Numerals 180 denotes the deltoideus motivator. Elements 181, 182 and 183 are assigned to a humoral flexor, the biceps brachii and triceps brachii motivator means. The equivalents to the Brachioradialis Exteral ulner extensor and radial abductor means are designed by numeric values 185, 186 and 187, respectively. The Numeral 184 designates a radial abductor. The ulnar abductors, phallange flexors and phallange extensors are collectively assigned the values 188, 189 and 190.

Figure 6A:
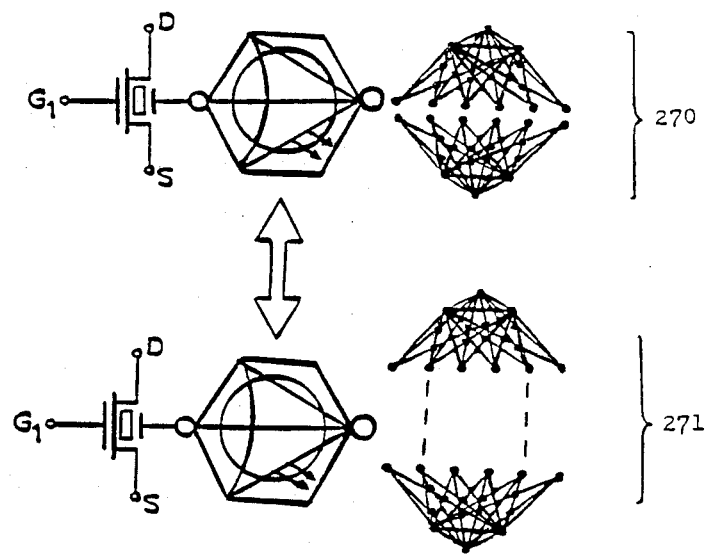
FIG. 6a is a pictorial representation of a single polyelectrolytic Gel element undergoing photonic excitation from a ground state to an elevated state.
Figure 6B:
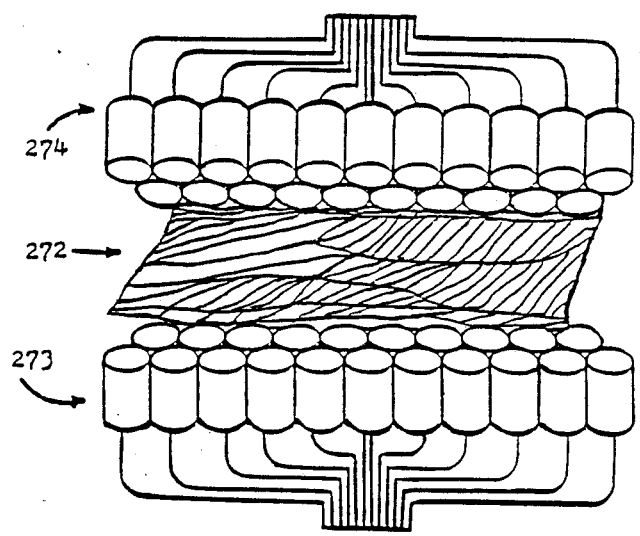
FIG. 6b is a concise pictorial representation of a portion of a single membrane structure.

FIG. 6 describes in a simplified diagrammatic fashion the arrangement of various laser drivers field generators, electro-optical power converters and chemical initiators embodied within the structure of a polyelectrolyte piezoelectric gel means. Numerals 258, 259 and 260 from FIG. 6 are assigned to elements which are indicative of an amplification power pulse circuit, a rechargable gas ion laser driver and an automated recycling reservoir/gasifier complex. Ion lasers are presently bulkier than solid state galium arsinide diode lasers (10,000:1 size differential), which are less energy efficient than diode lasers (0.10:0.95) and are comparatively limited in the life of lasing materials ($10^2$–$10^4$ hours versus $10^5$–$10^6$ hours continuous operation). The basic advantages of deploying an ion laser are that comparatively large quantities of continuous power can be reliably generated over a wide variety of optical bands (0.250–10.0 watts). Numerals 261, 262 and 263 denote a charging reservoir, an automated filter and pump means, as well as an electronic beam splitter, splitter-/optical band separator means. The power converter complex is indicated by element 264. Number 265 designates a single polyelectrolytic piezoelectric Gel element. Elements 266 and 267 are indicative of a semipermeable enclosed reservoir release means and reabsorption mechanism, respectively. Paired units 268 and 269, 270 and 271 shown in FIG. 6a, 272 and 272a, as well as 273 and 274 shown in FIG. 6b are illustrative of solid state single substrate laser actuators, a single polyelectrolytic piezoelectric Gel, is symbolically shown undergoing phase transition and a number of encapsulated polyeletrolytic piezoelectric elements, which are interdisposed between electro-optical chemical release actuator elements.

FIG. 6c is an illustrative perspective of the semipermeable membranes responsible for the release of specific anions, or cations, or other molecular constituents on the basis of differential size and/or charge. The speed and extent of contribution of a polyelectrolytic Gel is contingent on infinitesimal alterations in solvent composition, ionic concentration, salinity, pH and temperature including small variances in voltage. All volumetric alterations are considered to occur as a manifestation of phase transition, which is contingent upon the osmotic pressure gradients generated by counterions, a negative pressure exerted by polymer to polymer affinity and the variable elasticity of the given polymer network. The phase transition induced by the application of an electric field across a given polyelectrolytic Gel generates electric forces on charged sites of a given network initiating a stress gradient along the electric field lines of the specified active polyelectrolytic Gel complex. The collapse time of a given polyelectrolytic piezoelectric Gel varies in direct proportion to the square of its diameter and in keeping with this relatively long segments of Gels (3.0–10.0 cm) were prepared with diameters, which corresponds to micron proportions (50–500 microns). Therefore a single semipermeable membrane enclosure containing adequate supply of ions can and does service more than one polyelectrolytic Gel element. The outer most membranes component is designated by numeral 275 and is composed of an elastic composite of commerically available ceramic, celophane and polysacrhrides impregnated with hetrogeneous hydrophillic and hydrophobic exchange ions. The membrane has natural pores and is rendered porous by bombardment of high velocity charged ions, continuous radial bombardments of radioactive nuclei by an alpha source emitter, percolation, or other well known applied processes utilized by those skilled in the art. Elements 276, 277 and 278 of FIG. 6a designate a passive ceramic matrix rendered porous to specific ions, a polymorphic silicate layer and a fiberous layer, providing motility by capillary action. Reservoirs of ions or other substances are described by element 279. Numerals 280, 281 and 282 denote in part a complement of solid state diode lasers which emits at a specific frequency and wavelength complementary to the characteristic resonant frequency of a said membrane material. Elements 283 and 284 denote the vasodilation each pore site undergoes, due to internal stress factors produced by internal intrinsic resonance of the membrane structure itself upon photonic excitation. Numeral 285 designates the same said pore sites in their natural state in the absence of an emissive source. Numeral 286 is indicative of an electron micrograph of the membranes surface, which is undergoing photonic excitation.

Figure 6E:
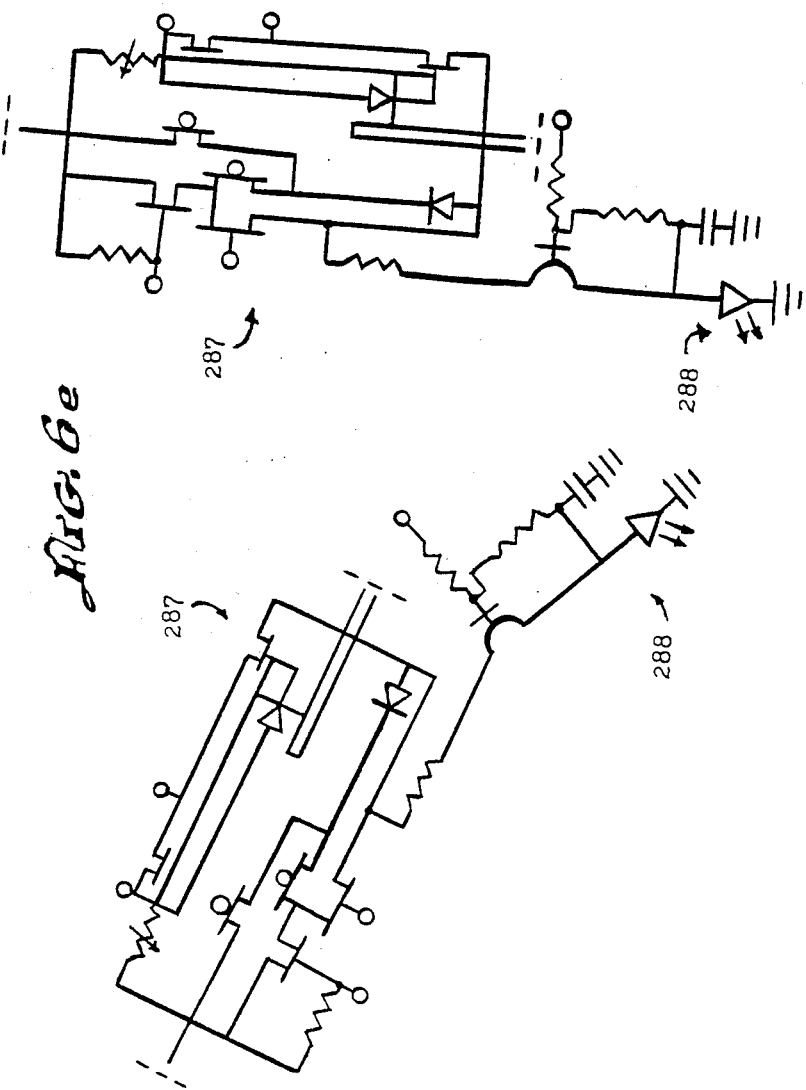
FIG. 6e is indicative of a concise schematic representation of a single modified optical circuit constructed on a single substate, which is utilized to alter membrane permeability, in low power applications and/or other related processes.

FIG. 6e is indicative of a simplified schematic representation of a single modified optical circuit, constructed on a single substrate and utilized for low power applications, as required by the polyelectrolytic gel means. The entire circuit for the sake of simplicity is assigned a single numeric value 287; whereas the extrinsic emitter, a laser diode composed of galium phosphate arsinide or other suitable compounds, as described by numeric value 288. The circuit is of an experimental but commerically available type, including all of its components are obtainable from subsidiaries of Hitachi, Fairchild, Texas Instruments and other suitable suppliers. The type and disposition of the single substrate circuit is incorporated into the framework of the artifical membrane system. The extrinsic laser diode source is specifically designed to emit the corresponding optimal resonant frequency of a given membrane complex. Systems employing laser diodes of the above mentioned type, also provide in large quantities the low power (2.54 to 5.00 V.D.C.) needed to drive polyelectrolytic piezoelectric means and can be modified to perform minute laser doppler analysis.

FIG. 6f are diagrammatic representations of the artifical membrane undergoing photonic excitation. A longitudinal section of the membrane is designated by numeral 289 and continuous portions of the same said membrane which are denoted by closely spaced vertical lines 289a through 289n!. The effective pore sites undergoing vasodilation due to photonic emissions that are distributed evenly throughout the membrane proper number 289 and are collectively assigned the numeric value of 290. The ionic constituents or osmotic components released from the reservoir due to excitation are represented by 290a through 290n!, and are depicted as numerous small black dots. The membrane structure has an intrinsic vibrational frequency or resonance based on its physical electrochemical nature, which is in effect its ground state. At ground state the diameter of pores are constricted; rendering said membrane relatively impervious to the flow of ions or other chemical constitutes, until activated by an emissive source. The emissive source in this case is a series of laser emitters, which act in an operative manner to dilate the pore sites by in effect causing the membranes lattice structure to resonant, expanding the membranes physical structure. Laser emissions of a characteristic wavelength and oscillation frequency is referred here to as photonic stimulation, or applied photonics. The resonant ground state is described graphically by elements 291, 292, 293 and 294. Levels of excitation, wherein specified chemicals (ions and the like) are released from dilated pore sites are graphically indicated by elements 295, 296 and 297. Note that there is a temporal lag between photonic stimulation and the release of specified chemicals from the surface of the artificial membrane, which may, or may not, have an electric charge bias placed on said structure. The release of chemicals enhance the contraction and reduce the intervals of contraction and the recovery periods. The chemical constitutents such as H+ ion concentration, or pH, increases the acidity of an aqueous medium when released into solution can enhance the rate and strength of contraction of a polyacrylamide motivator or its equivalent by a small but significant degree. The effect of the H+ release can of course be countered, or neutralized by the effects of a base, such as a hydroxyl group. The simplified equation $H^+ + OH^- \rightleftharpoons H_2O$ reaction, wherein water is reformed, forms the basis for chemical reconstruction of components. Water or other reformed chemical constituents such as salts of sodium, potassium, or other chemical means can also be reused by undergoing electrolysis in the presence of a catalyst. The separate ionic constituents once isolated from one another can be recycled continuously over the given life of a specified polyelectrolytic Gel means.

FIG. 6h illustrates briefly the process wherein acids, bases solutes, or other substances undergo chemical reformation, assimilation and dispersal. Effective reabsorption of excess residual chemical recombinants derived from acid/base titration, dissolved solutes, solvent, or other substances, undergo microelectroylsis in the presence of a catalyst disassociating a given recombinant into its constituent parts. Each constituent part is upon electrolytic separation isolated from one another and compartmentalized by electric field propagation. The motility of ions are enhanced by subjecting each constituent unit or ionic forces generates a concentration gradient which entails active transport. Active transport of ions across a given membrane occurs by photonic excitation. Embedded into the structural framework of each membrane are a series of uniformed electro-optical systems formed on single substrates associated with diffusers and a solid state laser diode means. The wavelength and oscillation frequency of the given laser diode means is selected to precisely match the intrinsic resonant frequency of the specified artifical membrane structure. The pore structure of a given membrane is intentionally sized to a specified diameter, such that under conditions of photonic excitation the pore diameters expand rendering the membrane permeable to a specific ionic constituent. The pore size upon termination of photonic excitation constricts, returning said membrane to an impermeable state. The process of reabsorption and assimilation procedes in the following manner; first the reconstituted material numeral 299 is passively absorbed from the synthetic polyelectrolytic Gels, numeral 298, by a simple passive concentration gradient. The reconstituted material undergoes electrolysis in the presence of a catalyst numeral 300. The separate ionic constituents are compartmentalized described by 301, 302; wherein appropriate sized ions are transferred to a secondary reservoir designated by numeral 303. The secondary reservoir has a much higher concentration gradient so when the membrane 304 undergoes photonic excitation by laser emitters, 305, 306, as the contents advance from 303 to a primary reservoir 307. An additional filtration ionic transfer membrane, which is described by 308 is followed by capillary action means 309 and elements 310, 311 and 312. The respective laser diode sources are designated by 313, 314, respectively.

FIG. 6i describes in a brief schematic manner the disposition of two equivalent adjacent differentially permeable release reservoir mechanisms. Each chemical release reservoir, 315, 316 is encapsulated by membranes 317, 318 and 319; which are impervious to the release of ions except in specified regions. The reformed or reconstituted chemical medium, numeral 320, is absorbed through membrane 321, by a chemically active layer, defined by number 322 from the motivator means, which is not shown here. The chemically active layer 321 consists of a catalytic agent in the presence of an electrolytic field separator. The electric field propagates the motion of charged ions to their respective isolation chambers, or secondary reservoirs listed by elements 323, 324, respectively. A positive pressure gradient builds up in reservoirs 323, 324; and via a microfeed back circuit the catalytic process is terminated, until a negative pressure gradient is generated at some future date. The contents of secondary reservoirs 323, 324 are released into primary reservoirs 327, 328 as a result of photonic excitation from a given laser diode source, not shown, of membrane elements 325 and 326. Phontonic excitation of said membranes 325, 326, occurs as a direct consequence of a negative concentration gradient generated by primary reservoirs 327, 328, as their respective ionic or chemical constituents are dispersed through membrane complexes 329 and 330. Membrane elements 329, 330 are isolated from one another by elements 315, 316, releasing said contents by photonic excitation. Each semipermeable membrane acts as a molecular or ionic sieve and is impervious to release of ions or other substances, until stimulated to do so by emission of photons at a specific wavelength and oscillation frequency. The release of ions or other substances varies directly with the specific quanta generated by the laser diode diffuser means, not shown here, and the number of quanta needed to vasodilate a given number of pore sites. The ions or other chemical constituents once released from the peripheral membrane structural units 329, 330 exit in groupings or packages, which are assigned the numeric values 331, 332, respectively. The packages numbers 331, 332, are released into the region of specified polyelectrolytic contractile elements propagated by a negative pressure gradient and/or electric field placed on the same said Gel means.

FIG. 7 is a simplified graphical representation of an evoked potential, which is propagated along the conducting axis of a piezoelectric element. Numeral 333 represents the electronic signal propagated; whereas numeral 334 denotes the axis of the piezoelectric material.

FIG. 7a describes in an illustrative manner the wave motion of a three dimensional piezoelectric structure with an arbitrarily shaped electrode configuration and external force distribution taken in real time. The total volume is defined by V with total surface defined by $\delta V$ and piezoelectric volume is defined by V'. The portion of $\delta V$, where $u_i$ is specified by $\delta V u$, of $\delta V$ where $T_{ij}N$ is specified by $\delta V_t$. The surface is indicated by $V'\delta V'$, with the electrode volume V-V' and interference between V' and electrode p is $\delta V'p$. The ground for the piezoelectric means is indicated and the actual physical wave motion of piezoelectric is described in brief by F and other cofactors.

The practical as well as theoretical implications of solid state piezoelectric operations have accurately been described by Holand, Eer Nisse and others in the field and are expressed in part by the equations described herein below:

$$F \int_{1 \to \infty}^{0 \to 1} = \frac{\delta V}{V'} \cdot \frac{T_{ij}N - \rho\omega^2 u_i}{dt} \left( \frac{V'\delta V' - \delta V'p}{V - V' - \delta V'p} \right) F \left( \frac{dx}{dt} \quad \frac{dy}{dt} \quad \frac{dz}{dt} \right)$$

The piezoelectric medium need not be homogeneous, but it will assume linear sinusoidal conditions prevail. Moreover, one will assume any motions, which are present vanish, as one retreats infinitely far from the origin, so that boundary effects at infinity may be neglected where, $$T_{ij} = c_{ijkl}{}^E S_{kl} - e_{mij} E_m$$

$$D_n = e_{nkl} S_{kl} + \epsilon_{mn}{}^S E_m$$

When these relations are expressed with particle displacement and electric potential $\phi$ as independent variables, to yield $$T_{ij} = c_{ijkl}{}^E U_{k,l} + e_{mij}\phi,m$$

$$D_n = e_{mkl} U_{k,l} - \epsilon_{mn}{}^S \phi,m$$

Commas denote differentiation, which is understood to be covariant in cases of non-Cartesian coordinates. Conservation of momentum is now expressed in differential form as $$T_{ij,j} = (c_{ijkl}{}^E k,l + e_{mij}\phi,m),j = -\rho\omega^2 u_i$$

Additionally, for insulating materials $D_n$ must not diverge, $$D_{n,n} = (e_{ukl} U_{k,l} - \epsilon_{mn}{}^S \phi,m),n = 0$$

Again, the problem of describing this situation with variance consists of finding some Lagrangian expression with a first variation, which is zero only if preceeding equations are valid. The following expression possesses this property:

$$L = \iiint_\alpha \frac{1}{2}(T_{ij}S_{ij} - D_m E_m - \rho\omega^2 u_i u_i)dV$$

$$= \iiint_\infty \frac{1}{2}(u_{i,j} c_{ijkl}^E u_{k,l} + 2\phi,m e_{mkl} u_{k,l} - \phi,m \epsilon_{mn}^S \phi,n - \rho\omega^2 u_i u_i)dV$$

In particular, if arbitrary independent variation are assigned to $U_i$, $U_{i,j}$, $\phi$, and $\phi,m$, we find the first variation in L is $$\delta L = \iiint_\infty \{[(-u_{i,j} c_{ijkl}^E - \phi,m e_{mkl}),l - \rho\omega^2 u_k]\delta u_k + \\ [(-e_{mkl} u_{k,l} + \epsilon_{mn}^S \phi,n),m]\delta\phi\}dV + \\ \oiint_\infty \{(u_{i,j} c_{ijkl}^E + \phi,m e_{mkl})\delta u_2 N_1 + (e_{mkl} u_{k,l} - \epsilon_{mn}^S \phi,n)\delta\phi N_m\}dA$$

Evaluation of $\delta L$ in this manner and use of the divergence theorem lead to the result, $$\delta L = -\iiint_V \delta u_i[(c^E_{ijkl}u_{k,l} + e_{nij}\phi_{,n})_{,j} + \rho\omega^2 u_i + f_i]dV$$

$$-\iiint_{V'} \delta\phi[(e_{mkl}u_{k,l} - \epsilon^S_{mn}\phi_{,n})_{,m}]dV \quad +\iint_{\partial V_T} \delta u_i[N_3(c^E_{ijkl}u_{k,l} + \phi_{,n}e_{nlj}) - \dot{F}_i]dA$$

$$-\iint_{\partial V_u} [u_i - u'_p]N_g(c^E_{ijkl}\delta\{u_{k,l}\} + e_{nij}\delta\{\phi_{,n}\})dA \quad +\iint_W \delta\phi[N_m(e_{mkl}w_{k,l} - \epsilon^S_{mn}\phi_{,n}) + A]dA$$

$$-\sum_{r=0}^M \iint_{\partial V_{u'}} [\phi - \phi_p]N_m(e_{mkl}\delta\{\mu_{k,l}\} - \epsilon^S_{mn}\delta\{\phi_{,n}\})dA + \sum_{r=1}^{M'} \delta\phi_r\left[\iint_{\partial V'} N_m(e_{mkl}u_{k,l} - \epsilon^S_{mn}\phi_{,n})dA + Q_r\right]$$

$$-\sum_{r=1}^{M'} \iint_{\partial l'_{v'}} [\phi - \phi_r]N_m(e_{mkl}\delta\{\mu_{k,l}\} - \epsilon^S_{mn}\delta\{\phi_{,n}\})dA$$

Consider, for example, the special case in which the external mechanical force is specified on the entire boundary and the displacement is specified nowhere. Then $$\partial V_u = 0$$

$$\partial V_T = \partial V$$

Similar restrictions on the electrical boundary conditions may often exist. For example, assume that there is no fee charge on the unelectroded portion of the surface and that the potential rather than the total charge is specified on all the electrodes, $$M' = 0$$

$$\lambda = 0 \text{ on } \partial V_\lambda'$$

Under the limitations of the above equation, it is most convenient to describe the linear response of the system by its electromechanical admittance matrix. In particular, the Lagrangian now reduces to $$L = \iiint_V \tfrac{1}{2}(u_{i,j}c^E_{ijkl}u_{k,l} - \rho\omega^2 u_i u_i)dV - \iiint_V u_i f_i dV +$$

$$\iiint_{V'} \tfrac{1}{2}(2\phi_{,m}e_{mkl}u_{k,l} - \phi_{,m}\epsilon^S_{mk}\phi_{,n})dV -$$

$$\iint_{\partial V_T} F\partial l_i dA -$$

$$\sum_{y=0}^M \iint_{\partial V_{p'}} (\phi - \phi_p)N_m(e_{mkl}u_{k,l} - \epsilon^S_{mn}\phi_{,k})dA$$

To determine the admittance matrix in this case, we first evaluate the particle displacement and potential patterns u and φ. This is done by expansion in terms of the normal modes of the system. Let $U_i^{(\nu)}$ and $\phi^{(\nu)}$ be the νth particle displacement and potential eigenmode solutions with $f_i$, $\partial V_u$, $F_i$, $\lambda$, $\phi_p$, and $M'$ all zero. In other words, these eigenmodes represent the homogeneous or unforced solutions of the body shown with all the electrodes short circuited.

The mechanical surface force $F_i$ is just a concentrated body force localized at $\partial V_T$. Thus, $F_i$ and $f_i$ can be combined symbolically into a single body force $f_i'$ given by $$f_i' = f_i + F_i\delta(V - \partial V_T)$$

Finally, it is necessary to state two orthogonality relations with eigen modes of different resonant frequencies can be shown to obey:

$$\iiint_V \rho u_i^{(\nu)} u_i^{(\mu)} dV = \begin{cases} N^{(\mu,\nu)} & \omega_\nu = \omega_\mu \\ 0 & \text{otherwise} \end{cases}$$

and $$\int_V \int u_{i,j}^{(\nu)} e^E_{ijkl} u_{k,l}^{(\mu)} dV +$$

$$\int_{V'} \int [\phi_{,m}^{(\nu)} e_{inkl} u_{k,l}^{(\mu)} + \phi_{,m}^{(\mu)} e_{mkl} u_{k,l}^{(\nu)} - \phi_{,m}^{(\nu)} \epsilon^S_{mn}\phi_{,n}^{(\mu)}] dV =$$

$$\begin{cases} N^{(\mu,\nu)}[\omega_\nu]^2 & \omega_\nu = \omega_\mu \\ 0 & \text{otherwise} \end{cases}$$

In the equation, the w is the resonant frequency, or eigen/frequency associated with mode ν and $N^{(\mu,\nu)}$ is the normalization integral. We shall assume hereafter that appropriate diagnonalization procedures have been carried out in the event of frequency degeneracy and that the modes have been normalized in analogy with $$N^{(m,m)} = 1$$

and $$L = \tfrac{1}{2} \sum_\nu (A^{(\nu)})^2(\omega_\nu^2 - \omega^2) - \sum_\nu A^{(\nu)} \iiint_V \int u_r^{(\nu)} f_r' dV +$$

$$\sum_\nu A^{(\nu)} \iiint_{V'} \int \phi''_{,m}[e_{inkl}u_{k,l}^{(\nu)} - \epsilon^S_{mn}\phi_{,n}^{(\nu)}]dV -$$

$$\tfrac{1}{2} \iiint_{V'} \int \phi''_{,m}\epsilon^S_{mn}\phi''_{,n} dV$$

At this point, we apply the stationary property of L to determine the $A^{(\nu)}$, $$-\frac{\partial L}{\partial A^{(\nu)}} = 0 \text{ for all } \nu.$$

By the process of subsitution, integration by parts of the second volume integral from utilization of the divergence theorem and other equations, as applied to mode ν, which yields $$A^{(v)} = \frac{1}{\omega_v^2 - \omega^2} \left\{ \iint_V \int u_i^{(v)} f_i dV - \sum_{p=\epsilon}^{M} \iiint_{\partial V} {}_{p'} \phi^v N_m[e_{mkl} u_{k,l}^{(v)} - \epsilon_{mn}^S \phi_{,n}^{(v)}] dA \right\}$$

Evaluation of the Short-Circuit Modes proceeds as the short circuit eigen modes introduced cannot in general be determined exactly. However, they may be approximated using the variance and again the Lagrangian Equation. In particular, substituting the relevant conditions of zero $F_i$, $\partial V_u$, $F_i$, $\lambda$, $\phi_p$, and $M'$ reduces to $$L = \iint \int_V \frac{1}{2} (u_{i,j} e^E_{ijkl} u_{k,l} - \rho \omega^2 \mu_i \mu_i) dV +$$

$$\iint \int_{V'} \frac{1}{2} (2\phi_{,m} e_{mkl} \mu_{k,l} - \phi_{,m} \epsilon^S_{mn} \phi_{,n}) dV -$$

$$\sum_{p=0}^{M} \iint_{\partial V} {}_{v'} \phi N_m(e_{mkl} \mu_{k,l} - \epsilon^S_{mn} \phi_{,n}) dA$$

Utilize this Lagrangian and approximate the u, and $\phi$ with a linear combination of trial functions, $$U_i \doteq \sum_{\alpha=1}^{S_m} B^{(\alpha)} U_i^{(\alpha)}$$

$$\phi \doteq \sum_{\beta=1}^{S_e} C^{(\beta)} \Phi^{(\beta)}$$

and here, $B^{(\alpha)}$ and $C^{(\alpha)}$ are unknown coefficients to be determined. The trial functions $U_i^{(\alpha)}$ and $\Phi^{(\beta)}$ should all possess second derivatives. However, they need not satisfy any of the differential equations or boundary conditions, except that $U_i^{(\alpha)}$ should not be zero for all $\alpha$ and $\Phi^{(\beta)}$ should not be zero for all $\beta$ at any point in V or on $\partial V'$ or $\partial V'$ where the exact solutions are not zero. Nevertheless, certain desirable results are achieved if the trial functions do satisfy some of the differential equations or boundary conditions, even though this is not required. For example, if the $\Phi^{(\beta)}$ satisfy $\phi = 0$ on $\partial V_p'$, the Lagrangian Equation may be simplified by the omission of the last term. Also, as in the elastic case the convergence rate will be increased by picking trial functions that satisfy some or all of the boundary conditions. These statements will be reviewed in more detail later. Generally speacking, if the $U_i^{(\alpha)}$ and $\Phi^{(\beta)}$ are complete sets of functions, this method will converge to the exact eigenmodes of the problem as $S_m$ and $S_e$ go to infinity, provided the above nonzero restriction is not violated.*

*Sets of functions that are complete in the ordinary Fourier or normwise sense and which are not all zero at the same point are said to be pointwise complete. Thus, (cos mix) forms a pointwise complete set on $0 \leq x \leq \pi$, but {sin mix} is only normwise complete.

Obtaining the following approximation for L:

$$L \doteq \frac{1}{2} \sum_{\alpha=1}^{S_m} \sum_{\beta=1}^{S_m} B^{(\alpha)} B^{(\beta)} [P(\alpha,\beta) - \omega^2 H(\alpha,\beta)] -$$

$$\frac{1}{2} \sum_{x=1}^{S_e} \sum_{H=1}^{S_e} C^{(\alpha)} C^{(\beta)} E(\alpha,\beta) + \sum_{\alpha=1}^{S_m} \sum_{\beta=1}^{S_e} B^{(\alpha)} C^{(\beta)} K(\alpha,\beta)$$

The P (elastic), H (kinetic), E (electric), and K (piezoelectric) interaction matrices in this equation are given.

The $B^{(\alpha)}$ and $C^{(\beta)}$ are now evaluated by using the stationary property of the Lagrangian, $$\frac{\partial L}{\partial B^{(\gamma)}} = \sum_{\alpha=1}^{S_m} B^{(\alpha)} [P(\alpha,y) - \omega^2 H(\alpha,y)] + \sum_{\beta=1}^{S_e} C^{(\beta)} K(y,\beta) = 0$$

$$\gamma = 1, 2, \ldots, S_m$$

$$\frac{\partial L}{\partial C^{(\gamma)}} = -\sum_{\alpha=1}^{S_e} C^{(\alpha)} E(\alpha,\gamma) + \sum_{\alpha=1}^{S_m} B^{(\alpha)} K(\alpha,\gamma) = 0$$

$$\gamma = 1, 2, \ldots, S_e$$

This operation corresponds to setting $\delta u_i = U_i^{(v\delta} B^{(n}$ and $\delta \phi = \Phi^{(v)} \delta C^{(v)}$ The condition expressed that these $\delta u_i$ and $\Phi^{(v)}$ need not satisfy the boundary conditions and differential equations. Like $\delta \phi$ and $\delta u_i$ and $\Phi^{(v)}$ and $U_i^n$ should, however, possess second derivatives in the domains of interest.

Equations can be more concisely expressed in matrix notation, $$[P - \omega^2 H][B] + [K][C] = 0$$

$$-[E][C] + [K_t][B] = 0$$

Holand & E. P. Eer Nisse i.e. Design of Resonant Piezoelectric Devices

The P, H, E, E, K, G, and J Interaction Matrices $$P(\alpha,\beta) = \iiint_V U_{i,j}^{(\alpha)} e^E_{ijkl} U_{k,l}^{(\beta)} dV$$

$$H(\alpha,\beta) = \iiint_V U_i^{(\alpha)} \rho U_j^{(\beta)} dV$$

$$E(\alpha,\beta) = \iint_{V'} \phi_{,m}^{(\alpha)} \epsilon^S_{mn} \phi_{,n}^{(\beta)} dV + SYM[E'(\alpha,\beta)]$$

where $SYM[E'(\alpha,\beta)]$ is the symmetric part of $$E'(\alpha,\beta) = -2 \sum_{p=0}^{M} \iint_{\partial V} {}_{s'} \phi^{(\alpha)} N_m \epsilon^S_{m,n} \Phi_{,n}^{(\beta)} dA \text{ for the short-circuit modes}$$

$$E'(\alpha,\beta) = -2 \left( \iint_{\partial V} {}_{a'} + \sum_{r=1}^{M} \iint_{\partial V} {}_{r'} \right) \Phi^{(\alpha)} N_{ln} \epsilon^S_{mn} \Phi_{,n}^{(\beta)} dA \text{ for the open-circuit modes}$$

-continued $$K(\alpha,\beta) = \int\int_V \phi^{(\beta)}_{,m} e_{mkl} U^{(\alpha)}_{k,l} dV + K'(\alpha,\beta)$$

where $$K'(\alpha,\beta) = -\sum_{p=0}^{M} \int\int_{\partial V'\,\nu'} \phi^{(\beta)} N_m e_{mkl} U^{(\alpha)}_{k,l} dA \text{ for the short-circuit modes}$$

$$K'(\alpha,\beta) = -\left(\int\int_{\partial V\,\nu'} + \sum_{r=1}^{M'} \int\int_{\partial V\,r'}\right) \phi^{(\beta)} N_m e_{mkl} U^{(\alpha)}_{k,l} dA \text{ for the open-circuit modes}$$

$$G(r,\alpha) = \int\int_{\partial V\,r'} N_m e_{mkl} U^{(\alpha)}_{k,l} dA$$

$$J(r,\beta) = \int\int_{\partial V\,r'} N_m \epsilon^S_{mn} \phi^{(\beta)}_{,n} dA$$

Here the subscript t designates a transposed matrix. Alternatively, may be represented as, $$[C] = [E^{-1} K_t][B]$$

$$[P + KE^{-1} K_t - \omega : H][B] = 0$$

It may be seen that this equation for the electroelastic short-circuit modes differs from equation for the purely elastic modes by the addition of the piezoelectric term $KE^{-1} K_t$.

Equations comprise a symmetric characteristic value problem, which possesses a solution only for discrete values of $\omega^2$. These eigen values, of course, give the approximate short-circuit resonant frequencies of the system squared $\omega^2$.

Let us represent the eigenvectors associated with the $\omega_v$ by $[B^{(v)}]$ and the individual components of $[B^{(v)}]$ by $B^{(\alpha,v)}$. These eigenvectors are determined only to a multiplicative constant the following equation. However, the approximate modal displacement patterns, which are specified by substitution of the $[B^{(v)}]$ into $$u_j^{(v)} \doteq \sum_{e=1}^{S_m} B^{(\alpha,v)} U_i^{(\alpha)}.$$

Two examples of short-circuit variational electroelastic modal calculations using the techniques are presented later on.

It is also possible to obtain variational approximate solutions for the open-circuit eigenmodes. The conditions of zero fi, $\partial vu$, Fi, $\lambda$, $Q_I$ and M appropriate to this computation reduce the Lagrangian Equation to $$L = \int\int\int_V \frac{1}{2}(\mu_{i,j} e^E_{ijkl} \mu_{k,l} - \rho\omega^2 \mu_j \mu_i) dV +$$

$$\int\int\int_{V'} \frac{1}{2}(2\phi_{,m} e_{mkl} \mu_{k,l} - \phi_{,m} \epsilon^S_{mn} \phi_{,g}) dV -$$

$$\int\int_{\partial V\,e'} \phi N_m(e_{mkl}\mu_{k,l} - \epsilon^2_{mn}\phi_{,n}) dA -$$

$$\sum_{r=1}^{M'} \int\int_{\partial V\,r'} (\phi - \phi_r) N_m(e_{mkl}\mu_{kl} - \epsilon^S_{mn}\phi_{,n}) dA.$$

We again expand $u_i$ and $\phi$ in a linear combination of trial functions $$\mu_i \doteq \sum_{s=1}^{S_m} B^{(s,0)} U_i(\alpha)$$

$$\phi \doteq \sum_{\mu=1}^{S_e} C^{(\beta,o)} \Phi^{(\beta)},$$

and substitute this into the Lagrangian. Again the $U_i^{(\alpha)}$ and $\Phi^{(\beta)}$ need not satisfy any of the boundary conditions or differential equations and may be quite arbitrary, except that they should not all be zero at any point where one does not anticipate the actual solution to be zero. Of course, the more of the boundary conditions or differential equations that are obeyed, the more rapid the convergence will be.

Performing the required substitution, we have the following approximation for L:

$$-L \doteq \frac{1}{2} \sum_{\alpha=1}^{S_m} \sum_{\beta=1}^{S_m} B^{(\alpha,v)} B^{(\beta,o)} [P(\alpha,\beta) - \omega^2 H(\alpha,\beta)] -$$

$$\frac{1}{2} \sum_{\alpha=1}^{S_e} \sum_{\beta=1}^{S_e} C^{(\alpha,o)} C^{(\beta,o)} E(\alpha,\beta) + \sum_{\alpha=1}^{S_m} \sum_{\beta=1}^{S_e} B^{(\alpha,o)} C^{(\beta,o)} K(\alpha,\beta) +$$

$$\sum_{r=1}^{M'} \sum_{\alpha=1}^{S_m} \phi_r B^{(\alpha,o)} G(r,\alpha) - \sum_{r=1}^{M'} \sum_{\rho=1}^{S_e} \phi_r C^{(\beta,o)} J(r,\beta)$$

where the P, H, E, K, G, and J matrices are given.

Figure 7B:
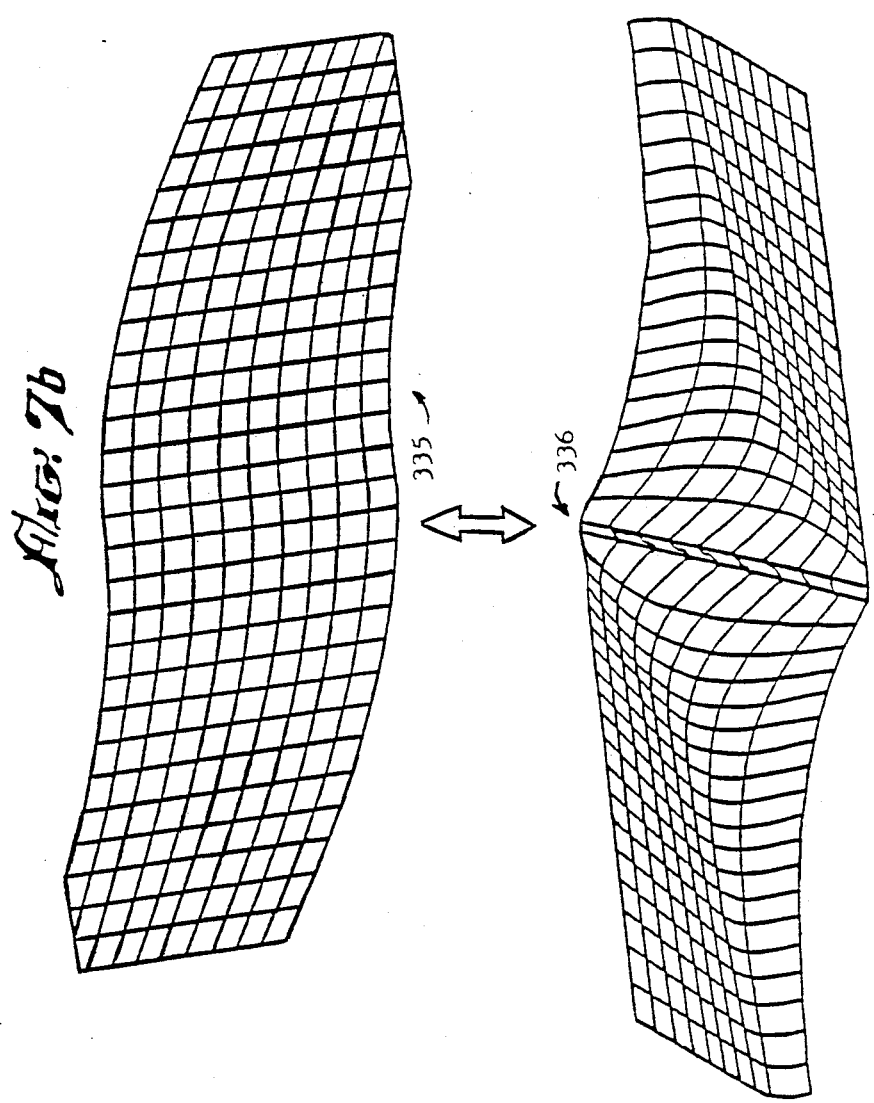
FIG. 7b is a pictorial representation of an evoked potential initiating a peristaltic motion of a piezoelectric means.

FIG. 7b is a pictorial representation of an evoked potential initiating a peristaltic motion of a piezoelectric means. The origin of primary sinusoidal contortion is indicated by numeral 335; whereas the minor modality of physical or mechanical distortion is designated collectively be numeral 336.

Figure 8:
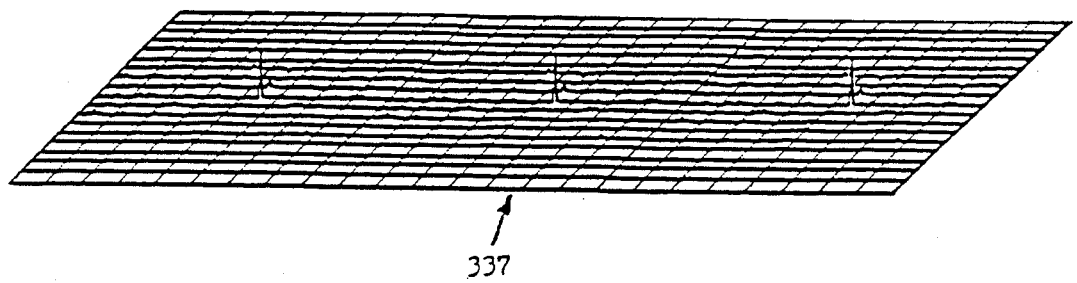
FIGS. 8, 8a, and 8b denotes a pictorial representations illustrating an over view of the evoked potential and wave motions described in FIGS. 7, 7a and 7b, respectively.
Figure 8A:
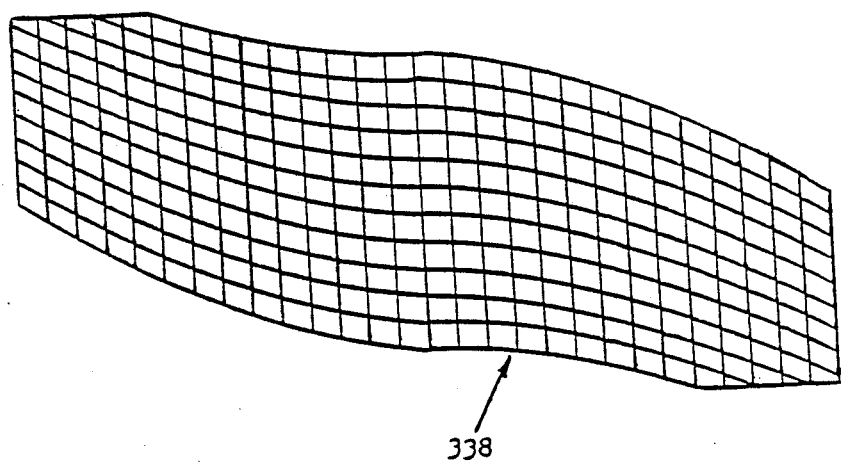
Figure 8B:
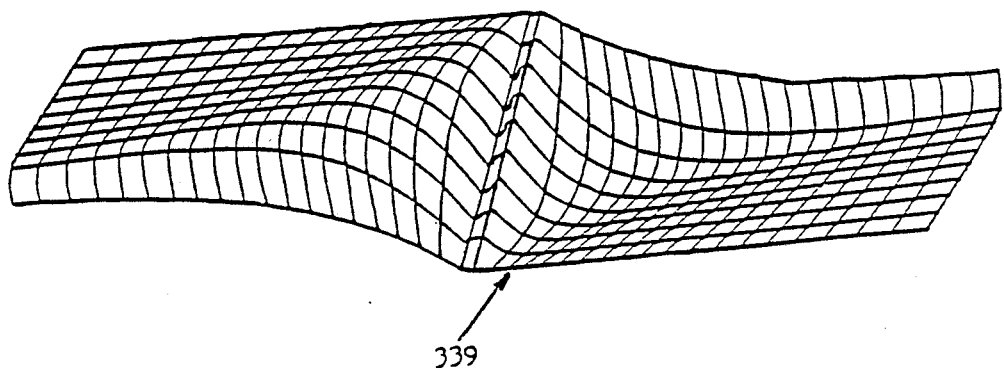
Figure 12A:
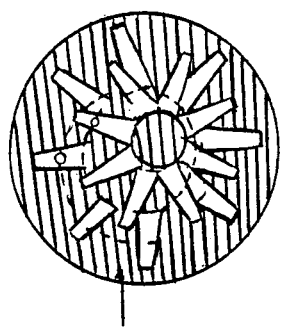
Figure 12B:
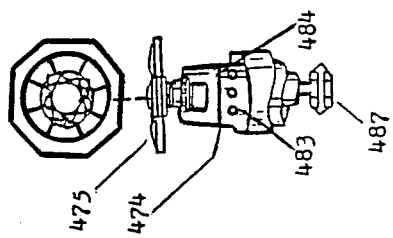
Figure 12:
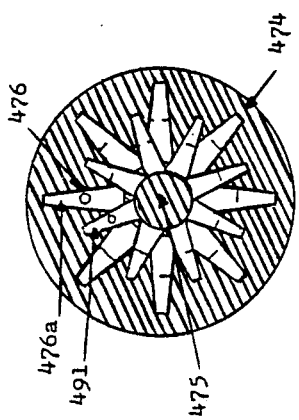

FIGS. 8, 8a, and 8b denote pictorial representations illustrating an over view of the evoked potential and wave motions, as described in FIGS. 7, 7a and 7b, respectively. Each element of FIG. 8 is assigned a numeric value, of which there are three, 337, 338 and 339, respectively.

The phenomenon of phase transition can be initially described by the simplified diagram disclosed in FIG. 9 and in terms of mean field equations developed by Flory and Huggins. The following parameters are a definitive finite network consisting of V polymers each cross-linked and each polymer containing No freely jointed segments, of which a fraction, $f$, are ionized. Each gelatinous network is formed with a cylindrical configuration with length Lo, diameter Do and concentration $\phi_o$. There also exists a so called special condition of no interaction between polymer segments, which is initialized as a reference state from which either expansion or contraction is measured. E defines a uniformed electric field applied along the axis of the gelatinous polyelectrolytic medium. Translational motion of the entire polyelectrolytic Gel along the electric field E is prohibited by fixing to a stationary electrode at one end  and attaching the other end to a fused juncture, supports, pins, rivets, or other structures. The contractile gelatinous medium is either compressed or stretched along its axis depending upon the direction of the electric field and/or polarity of the current. Contractile motion is also do to charged sites embodied within the given polymer network of uncharged cylindrical Gels with a variable thickness $\Delta Zo$ are located at a distance Z and subjected to an electric field E, the thickness changes to $\beta \Delta Zo$ with a diameter or $\alpha Do$, a radial expansion of $\alpha$ values; and axial expansion $\beta$, which minimizes the free energy F of a given cylindrical Gel for a given reduced temperature T, and reduced electrical potential B. The null or unusable states are indicated by a hatched parabolic-like boundary, whereas the dashed and dotted lines of the so-called unstable region are within the assignable states with the same free energy or F values. The polyelectrolytic Gel can change between the aforementioned given states with infinitesimal alterations in the electrical potential B described by dashed lines, or as a function of temperature T, denoted by the dotted line, as indicated in the modified transition phase diagram based on the equations of Flory and Huggins and in part on a diagram originally proposed by Tanaka, Nishio and others. The X axis and the Y axis elements are by values of $\alpha$, $\beta$ and spatial temporal field vectors X, Y, Z and T. The accumulative force generated by a systematic grouping of equivalent polyelectrolytic Gel contractile elements acting in concert is generated in the form of a hyperbolic paraboloid, described by numeral 340.

The polyelectrolytic Gel are prepared serially in accordance with methods of Tanaka, Nishio, Sun and others. In the case of polyacrylamide Gels, which are prepared by free radical polymerization. Acrylamide, the linear constituent; N, N'-methylenebisacrylamide, the tetrafunctional cross-linking constituent; and ammonium persulfate and N, N, N', N'-tetramethylethylene diamine (TEMED), the initiators, were dissolved in water. Micropipettes with a well-defined diameter ranging from 200 micrometers to 1.4 mm are immersed in this solution. In ten minutes, the solution is gelled and after an hour, the Gels are removed from the micropipettes and immersed in water to wash away residual monomers. The Gels then underwent hydrolysis in a 1.2 percent solution of TEMED (pH 12) for more than a month. Approximately 20 percent of the acrylamide groups were converted to acrylic acid groups, some of which were ionized in water.

$$-CONH_2 \rightarrow -COOH \rightleftharpoons -COO^- + H^+$$

If the composition of the acetone water mixture is varied, the volume of these Gels can change by a factor of 300 with an infinitesimal change in the solvent composition. After hydrolysis the Gels were immersed in a 50 percent acetone water mixture. Once equilibrium was reached, the Gels were cut into segments 3-60 cm long. The diameter of each segment was approximately 200 micrones to 4 mm.

Once the gels are properly shaped they are situated or interdisposed in between two micro-miniature platinum electrodes, such that a stationary current is momentary generated in the Gel placing a force on the negatively charged acrylic acid group of the polymer network pulling the Gel medium towards the positive electrode. A uniaxial stress is generated along the axis of the gel, which is maximized at the positive end electrode and minimized at the negative electrode end; producing a generalized stress gradient causing the polyelectrolytic Gel to undergo physical deformation systematic of contraction.

It is within the process known as the phase transition phenomenon where in the Gel collapse is reversible when the electric field is reversed. If the 50 percent acetone water mixture in which the polyacrylamide is immersed and replaced with pure distilled water the Gel's diameter will change continuously along its axis with the application of said electric field. The speed of contraction varies proportionately with the square of the Gels diameter, such that, polyelectrolytic Gel means requiring fast contractile rates have diameters in the micrometer range; whereas those Gel units required to perform relatively slow continuous or repetitive tasks indicative of peristaltic contraction have larger diameters than veins or arteries Variations of the Flory and Huggins equations are for phase transition under electrical field excitation, are straight forward and clearly explicated in a representative fashion in annexed equations contained herein below;

The combinations $(\alpha, \beta)$ that minimize the free energy F of the disk. The free energy includes a term associated with the deformation of the Gel Fg and a term for the work done against the electric field Fe.

$$F = Fg + Fe$$

For Fg we use the Flory-Huggins formula, $$Fg = vkT \left\{ N_o \frac{1-\phi}{\phi} \left[ \ln(1-\phi) + \frac{\Delta F}{kT}\phi \right] + \frac{1}{2}[2\alpha^2 + \beta^2 - 3 - (2f+1)\ln(\alpha^2\beta)] \right\} \frac{\Delta Zo}{Lo}.$$

where I is the absolute temperature, K is the Boltzmann constant, $\phi$ is the volume fraction of the polymer network, and $\Delta F$ is the free energy decrease associated with a contact between two polymer segments ($\Delta F$ varies with the solvent composition). The free energy needed to expand the network against the electric potential is given by $$Fe = vfeE(Z/Lo)(\beta-1)\Delta Zo \equiv \beta vkT(\Delta Zo/Lo)(\beta-1)$$

where e is the electron charge and $\beta \equiv feEz/kT$ is the reduced electric potential. Minimization of the total free energy yields two equations, $$\alpha^2 = B^2 + B\beta$$

and $$(N_o)/\phi_o[\ln(1-\phi)+\phi+(1-r))\phi^2/2]-(f+\tfrac{1}{4})(\alpha^2\beta)+1/\beta=0,$$

where $r \equiv 1-2\ \Delta F/kT$ is the reduced temperature. Equation above shows that the anisotropy of deformation of the disk is uniquely determined by B. If B is positive, the disk is compressed more in the axial direction than radially ($\alpha > \beta$). The reverse if true if B is negative. For certain values of r and B, they have two solutions corresponding to two minima of free energy.

FIGS. 10, 10a are concise, partial schematic block diagrams representation illustrating electro-optical signals generators and driver means utilized to power artifical solid state piezoelectric polyelectrolytic means. Elements 341 through 346 of FIG. 10 are indicative of electro-optical coupling circuits associated with sensory feedback systems, optical electrical line drivers are assigned values 347 through 349 for the temporal signal synchronizing electro-optical converter means 350. Numerals 351 through 363, describe low-power bidirectional system drivers. Elements 364 and 365 designate a complex of signal processors which modulate and control the electronic signal characteristics of signals 366 shown in FIG. 10a, 367 and 368. Element 369 is electro-optical coupling devices utilized to amplify and expand signals based on supplementary input from feedback systems. Numerals 370 through 377 represent auxillary solid state laser diode drivers. Element 378 designates an electro-optical signal coupler and integrator means. Unitary means 379 through 383 are assigned to devices representative of units ranging from solid state piezoelectric means to polyelectrolytic Gels. Polystyrene in a non-aqueous solution is equivalent in operation to polyacrylamide previously disclosed and is embodied within polyelectrolytic Gels.*

*functional parameters of contractile elements composed of polystyrene deviate nominally from the parameters of the aforesaid polyacrylamide contractile units, then disclosure of one said contractile unit discloses the other aforementioned contractile element.

FIGS. 11, 11a are indicative of exploded pictorial views of an industrial type robotic limb means composed of multiple gearless disc drive units powered by several special piezoelectric engine means. Numerals 384 and 385 of FIG. 11 depicts two self contained adjustable synchronous piezoelectric engines. Each engine is provided with a flexible articulating shaft described by numbers 386 and 387 which provides the system with a rapid percise angular motions that can be exacted. Rotary motion and torque are transmitted between the disc plate structures, as denoted by numbers 388 through 395. Each plate structure is separated from one another by jeweled ball bearing elements, as indicated by numbers 396 through 424. Each ball bearing element is contained within its own complementary matching receptacle, as defined by numbers 425 through 442. The raised surfaces or curvatures located on the disc structures are of a spiral retrograde nature, which are described by numbers 443 through 460. The rate of speed exacted by the drive shaft may either be reduced or increased, as well as increasing the torque value by altering the dimensions of the raised spiral curvature which exists on two of the four interfacing plates. The circumferences of said discs and ancillary structures such as the overlapping hubs provide variable ratios. The system is so constructed to provide at any given time that forty-five to fifty percent of the jeweled ball bearings are in the driving mode. The action of disc system in the driving mode is entirely different than gear systems which at any given time have the entire output load riding on only a few gear teeth. The gearless antifriction disc system is virtually devoid of backlash or slippage. A synthetic high polymer graphite lubricant which is not shown, increases the drive efficiency and wearing properties of the ball bearing system. The outer casing denoted by numerals 461 through 465, with all materials composing the disc drive system, which is composed of a laminated, multi-layer, non-metallic composite material, well known by those skilled in the art. Each of the shells of the outer casing structures are secured to one another by eight securing bolts, described by numbers 466 through 473; with sealing washers or gaskets, denoted by numerals 487 and 488, not shown.

FIGS. 12, 12a, 12b, 12c, 12d, and 12e are detailed partial perspective views of a piezoelectric drive engine with operative piezoelectric drive elements circumferentially disposed around a common central drive shaft. Rotation of shaft 444 provides an elliptical motion for primary disc 475. The contact disc 475 interfaces with a secondary complementary disc of the robotic unit, which is not shown here. At any given time there are at least six to eight piezoelectric units, described by numerals 476 through 491 that drive said shaft means 474. Each piezoelectric driving means is fitted with a angular fused, self-lubricating, composite plunger means; which upon actuation is thrusted precisely into a complementary angular depression or insert located in the shaft 474. The axial depression or point of angular insertion are shown in part by elements 483 and 484 with the angularized piezoelectric plunger means that are designated in part by elements 477 through 482. The individual piezoelectric or elements are actuated sequentially in a manner conducive to the rotation of shaft 474 and disc structure 475 in a circular elliptical fashion. The piezoelectric groupings are arranged in multiples of three such that forward rotation is provided by six separate and distinct elements, with reverse circumferential motion motion, which is provided by an equivalent number of piezoelectric elements. Additionally, six equivalent units are arranged in a neutral fashion providing for breaking, ancillary forward and reverse standby modes. The shaft numeral 474 is composed of a ceramic synthetic graphite base 485, with the capability of having minor localized portions, 486, that are capable of undergoing magnetic induction, such as the aforementioned angular portions and the secondary floating ball bearing system, located at the base of the same said shaft. Now we come to the base and angular ports that may or may not undergo localized magnetic induction 486, unlike standard electric motors, which are primarily powered by large scale alternating magnetic fields via local magnetic brush means. The shaft is affixed to and revolves in a synthetic self lubricating jeweled ball bearings system, which is described in brief by elements 487. The absence of magnetic brushes, solenoids, or other structures greatly reduces power surges that might otherwise interfer with the operation of electronics such as microprocessors, which are responsible for signal synchronization. Rotation of the said shaft 474 and disc means 475 are provided by a series of synchronous signals sent to each separate and distinct piezoelectric element. The piezoelectric element can be composed of those commerically available materials, which were mentioned earlier, or variations thereof. Power converters are needed to convert optical digitized signals into their electronic electrical analogs; however photovoltaic Gels, a subclass of the aforementioned polyelectrolytic Gels are well known by those skilled in the art. Ion or plasma laser means are indicated by unit 488 through 491 and act as driver means for a complex of photovoltaic Gel means, which are designated by numeral 492. In cases where numerous piezoelectric elements are indicated, fewer ion laser systems are deployable because of limited available power sources, size, weight and other considerations. A single laser source driver element is separated into multiple divergent beams which are conducted to multiple piezoelectric elements by solid state Q-switching elements designated by numerals 493 through 496, which are coupled to a complex of fiber optic means assigned a single numeral 497. The control of emittance, amplitude, frequency, intensity and electronic state of electro-optical systems and the designated responses to feedback processes are under the specific command of the main microcomputer, as described collectively by numerals 498 through 500.

Figure 13:
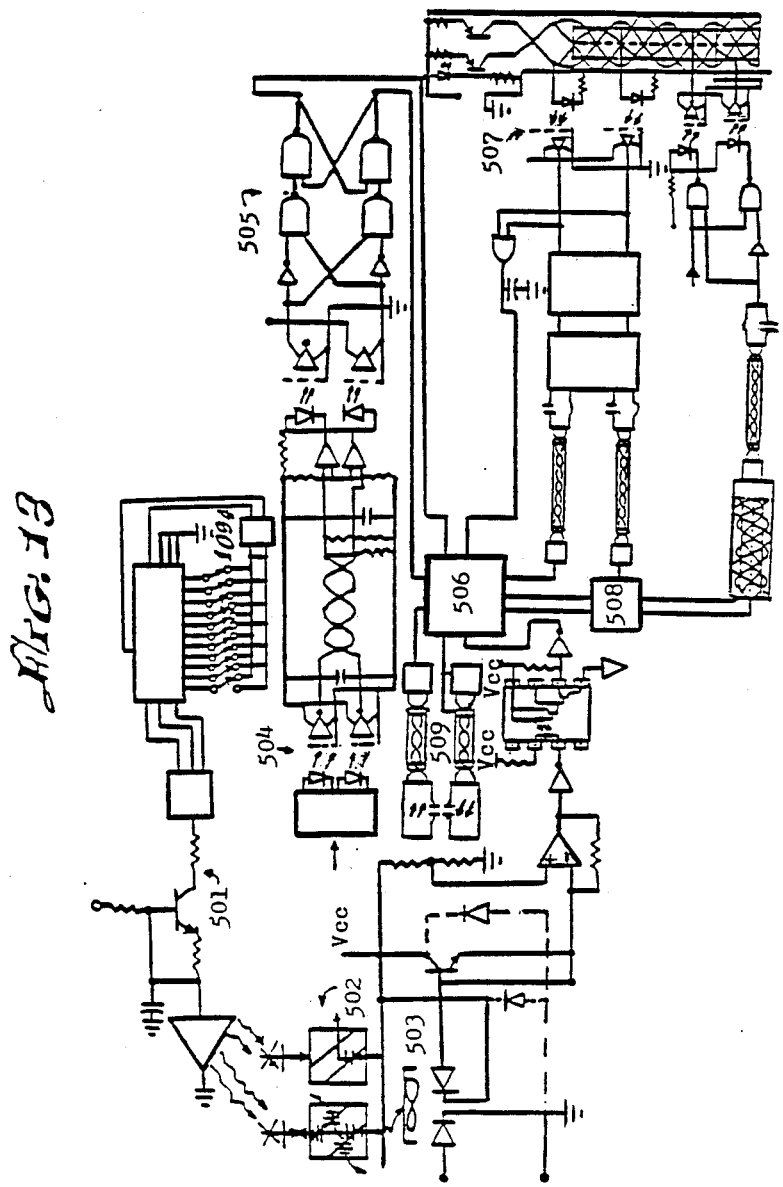
FIG. 13 is a concise combination block diagram and schematical representation in which only one of several optical electronic analog/digital converter units deployed by the piezoelectric means is exhibited.

FIG. 13 is indicative of a concise block diagram/circuit diagram of the system specifically keyed to track the exact wavelength and frequency oscillation of a coded laser diode means. Here the optical electronic means governs the intercept of a designated emission by a given fiber optics elements associated with projectiles pursuit or otherwise. Numerical values will be assigned to various simplified subsystems rather than their commercially available component parts for the sake of simplicity. Numeral 501 of FIG. 13 describes a typical laser diode; whereas elements 502 and 503 designates a PGL Q-switch and reflective tracking means. The split phase driver unit is depicted by numeral 504 and the line signal, electro-optical/flip-flop means is denoted by element number 505. A high speed commercially available electro-optical microcomputer designated by numeral 506, acts as a high speed comparator and tracker which is being keyed to home in not only on the specified laser wavelength and frequency, but on a specific coded oscillation rate, in order to negate the possibility of reacting to spurious signals. The optical electronic transmission lines provide signals to be reacessed and sent to explicit feedback systems, which are not shown. Numeral 509 denotes a simple servo mechanism, such as the articulating arm bearing the conduit system which receives and sends laser impulses to the command unit element 507. Numeral 508 designates a typical laser gyro system equivalent to that embodied within the structure of said piezoelectric means, and interfaced with elements 506, 509.

Figure 14:
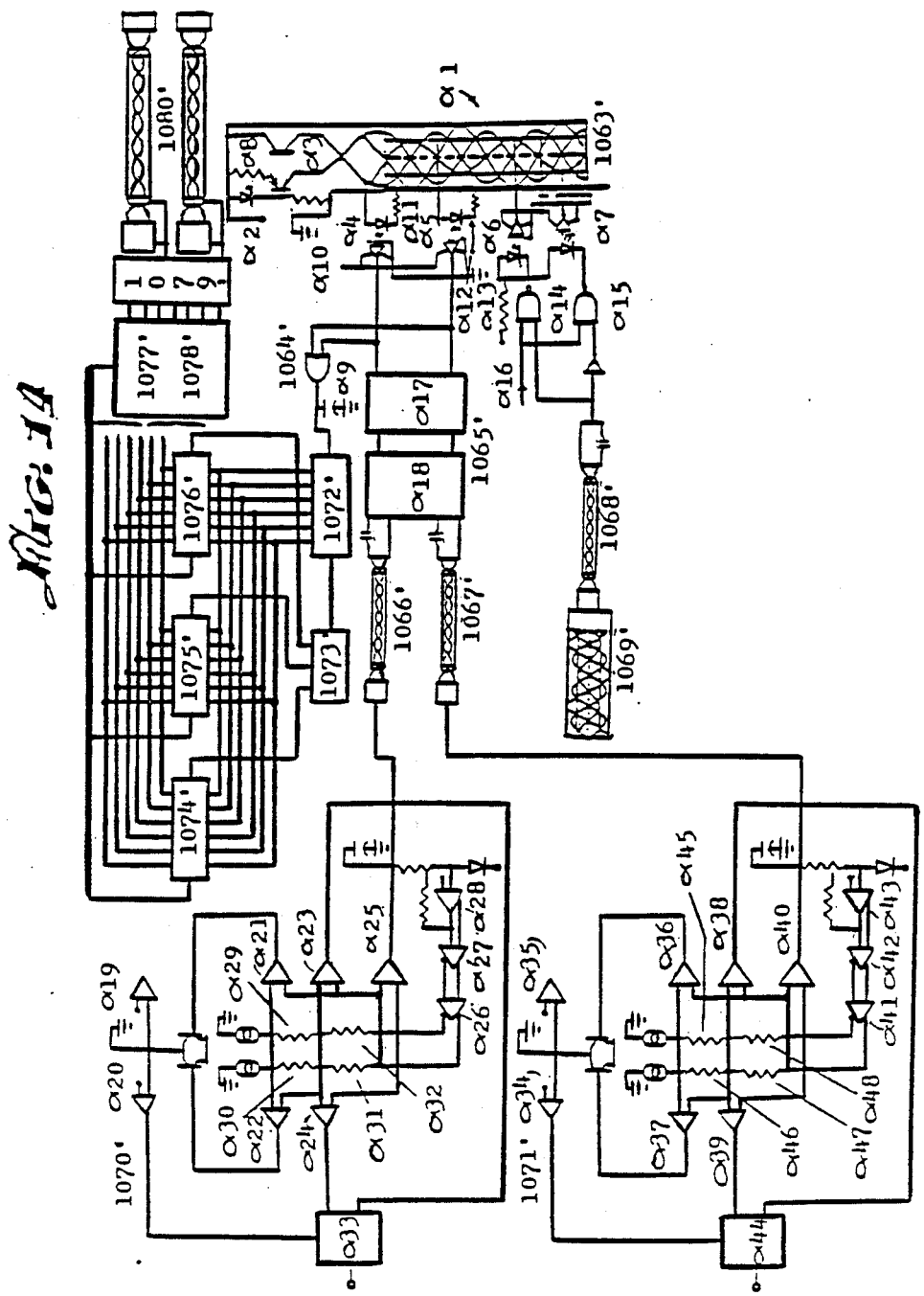
FIGS. 14, 15 describe in part schematic representations and block diagrams of other exemplary forms of optical electronic analog/digital converter means also employed within the embodiment of the piezoelectric prosthetic device.

FIG. 14 is a combination block diagram and a simplified schematic representation of only one of several equivalent optical electronic multiplexing stations associated with the preferred embodiment. Each electronic subsystem will be assigned a numerical equivalent and all pertinent component parts will be designated an alphanumeric value. Each and every component structure or equivalent structure is readily commerically available from such sources as Hewette-Packard, Texas Instruments, or other suitable manufactures. A generalized version of a multiplex station is illustrated by numeral 1063, and 1064, which denotes a logic gate, while $\alpha 1$ is descriptive of a typical signal line and $\alpha 2$ defines the transmission line supply. Alphanumeric symbols $\alpha 3$, $\alpha 4$, $\alpha 5$, $\alpha 6$ and $\alpha 7$ collectively denotes open collector outputs. $\alpha 8$ through $\alpha 13$, describes various resistive elements. The data is inputed via line $\alpha 14$ and $\alpha 15$, denoting an enable segment. The line status is denoted by $\alpha 16$. Numeral 1065 consists of two mutually exclusive or flip-flop subsystems, that are denoted by $\alpha 17$ and $\alpha 18$. Incorporated in $\alpha 17$ is an independent wave interrupt sequence, whereas $\alpha 18$ consists of an exclusive, or flip-flop system with a Kalman filter. Numerals 1066 and 1067 consist of specially encoded optical electronic data output channels. Numerals 1069 and 1068 are indicative of a data influx channel with element 1068 being a data compression undergoing compression prior to systems entry. Numerals 1070 and 1071 describe two separate but equivalent block diagrams from a four chip hybrid receiver means, each of which act to separate wave characteristics, with $\alpha 19$ denoting the link monitor output VREF; whereas $\alpha 20$ describes the ALC Amp and VREF. $\alpha 21$ is indicative of a negative peak comparator; whereas $\alpha 22$ is indicative of a positive peak comparator. The logic low and high comparators are denoted by $\alpha 23$ and $\alpha 24$. The differential amplifier stage and the gain control stage are described by $\alpha 25$ and $\alpha 26$. The bias voltage pre-amp, described by $\alpha 27$, $\alpha 28$ explains the D.C. restorer amp. Elements $\alpha 29$ through $\alpha 32$ depict resistors. The element $\alpha 33$ is representative of an R-S flip-flop data output means. Numeral 1071, as previously noted is equivalent to numeral 1070; and therefore elements $\alpha 19$ through $\alpha 33$ are equivalent to elements $\alpha 34$ through $\alpha 48$. The present status of each signal enters element 1072, a mainline sequencer, which then sends its input data to a clock means, which is denoted by numeral 1073. The data processed by numerals 1072 and 1073 are collectively sent to numeral 1074 through numeral 1076, which consists of three equivalent short term storage multivibrator means. Numeral 1077,1078 consists of a Kalman filter encoder means. Numeral 1079 depicts a biphasic line. The digitized electronic signals are converted into their optical electronic binary equivalents, and is the sent to the main computer complex for further analysis, as noted by numeral 1080.

Figure 15:
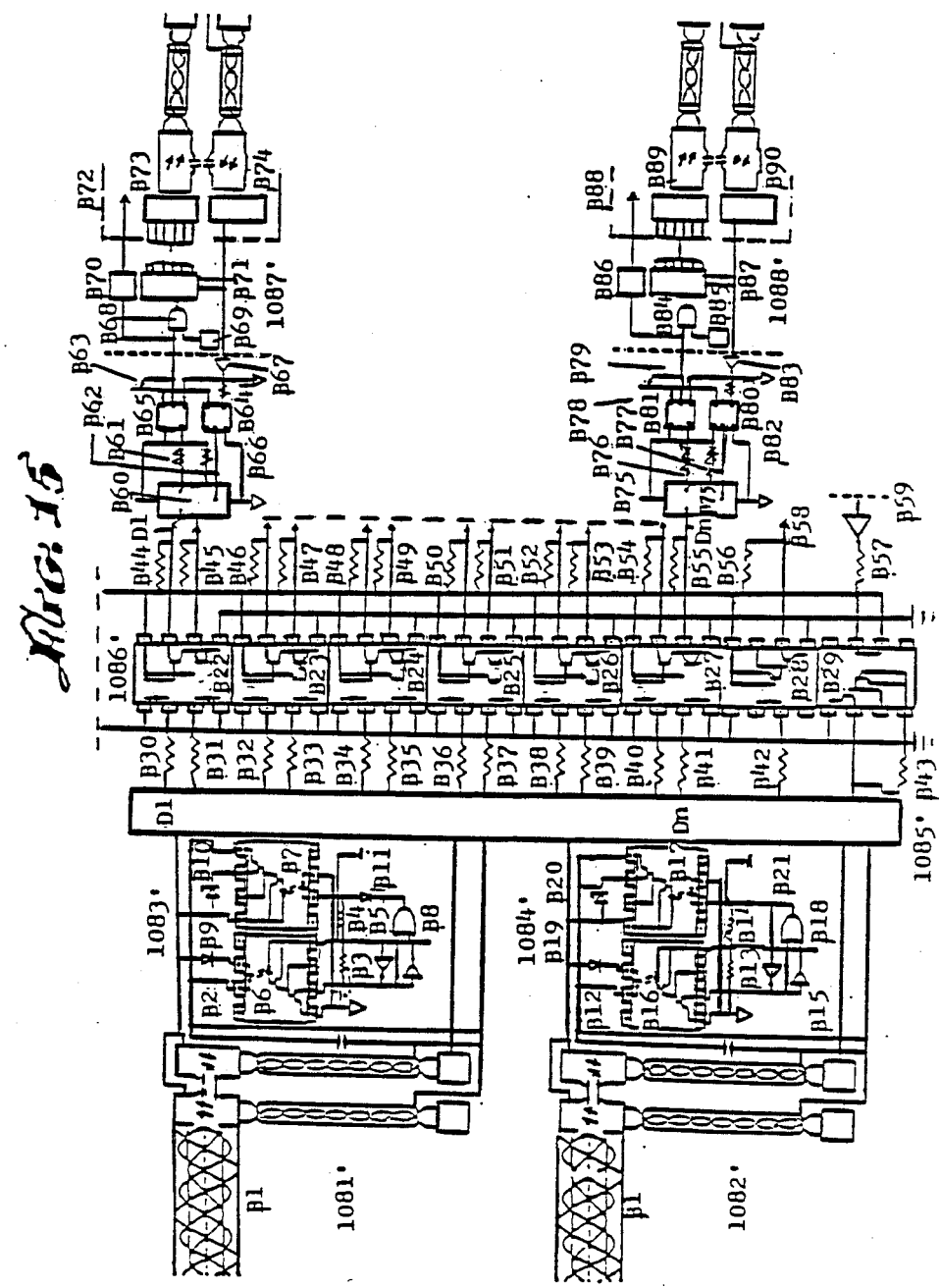
Figure 16:
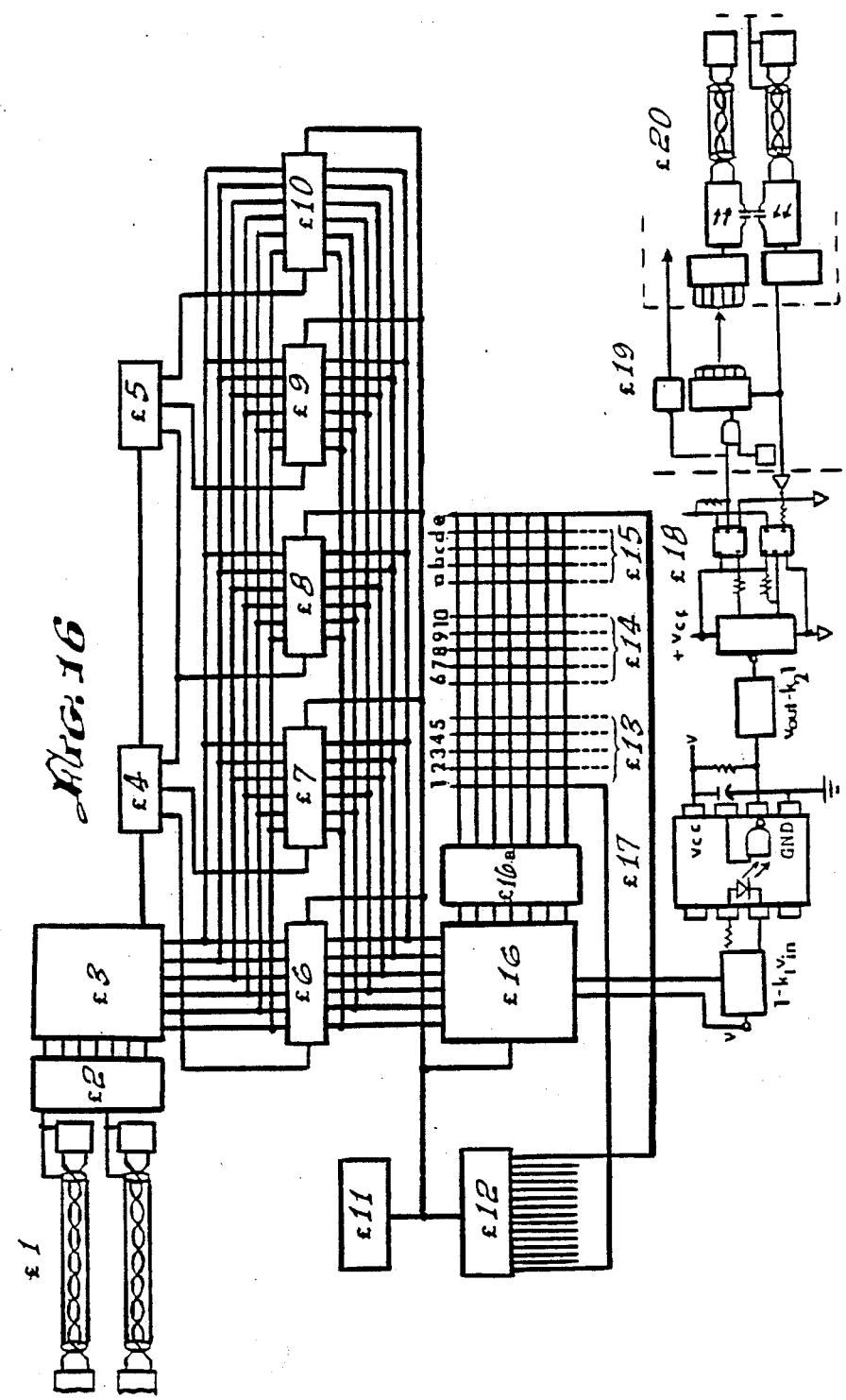
FIG. 16 is a concise block diagram of a portion of a VLSI logic signal analyzer, comparator and optical electronic analog/digited converter feedback unit employed in the prosthetic device.

FIG. 15 depicts a combination block diagram and a partial schematic of an exemplary form of a single optical electronic analog/digital converter unit. FIG. 15 like that of FIG. 16 is composed entirely of commerically available components, each of which is assigned an alphanumeric value. Subsystems 1081 and 1082 are a equivalent optical line driver and receiver means that receives a given transmission wavelength and/or its reference beams. Numerals 1083 and 1084 are equivalent and indicative of common optoisolators. The resistor elements of 1083 are denoted by $\beta 1$ through $\beta 5$. The accompanying optical electronic IC means is described by $\beta 6$ and $\beta 7$, respectively. The effective ground and logic element is described by $\beta 8$. $\beta 9$, $\beta 10$ and $\beta 11$ describe other diode means, which are associated with the subsystem. Numeral 1083 is equivalent to numeral 1084, therefore all components of numeral 1083 are equivalent to those of 1082, such that components $\beta 1$ through $\beta 10$ are equivalent to components $\beta 11$ through $\beta 21$. Numeral 1085 represents an analog/digital converter means IC $\beta 22$ through $\beta 29$ of numeral 1086, which in turn describes the isolated analog/digital in term of parallel data outputs. Components $\beta 30$ through $\beta 57$ denote resistor elements of numeral 1086 for the respective data outputs as denoted by Di through Dn. $\beta 58$ denotes the start converter process, whereas $\beta 59$ describes the termination of the converter process, and $\beta 59$ describes the termination of the converter process. Each data output is received by a digital/analog isolator system, two of which are denoted by numbers 1087 and 1088. Numeral 1087 and 1088 are equivalent to one another, and to all similar such units. A multivibrator means of numeral 1087 is denoted by β60. The resistive elements of the subsystem 1087 are described by the alphanumeric values β61 through β64. There are two equivalent IC's, as denoted by β65 and β66. β67 is indicative of a logic inverter, β68 depicts a oscillator and β69, which denotes a logic AND gate. The one shot means is denoted by β70 and the clock counter means is described by β71. The microprocessor system is described herein by β72 with an input port denoted by β73 and an output port indicated by β74 component elements, with β75 through β90 of numeral 1088 being equivalent to those elements β60 through β74 of numeral 1087.

FIG. 16 exemplifies a concise combination block diagram and schematic representation of only one of several optical electronic analog/digital converter feedback units, which are employed for sensory updates, servo-scans and related processes. Alpha numeric values are assigned to each subsystem in order to more clearly define a few basic component systems. Elements £ 1, £ 2 and £ 3 are indicative of the optical electronic sensor array, optical electronic encoder and analog/-digital interphasing and keying means. Alpha numeric values £ 4, £ 5, and £ 6 through £ 10 designate array selectors and a full complement of input storage buffers. Elements £ 11, £ 12 and £ 13 through £ 15 denote a clock/timing means, column drivers, as well as, display terminals. Element £ 16 collectively describes a VLSI chip containing data input transfer, a column selector, comparator encoder/decoder signal outflow means. Elements £ 17, £ 18, £ 19 and £ 20 designate a voltage to frequency converter, monopulse multivibrator drive means and a line driver/line receiver bidirectional means.

Figure 17:
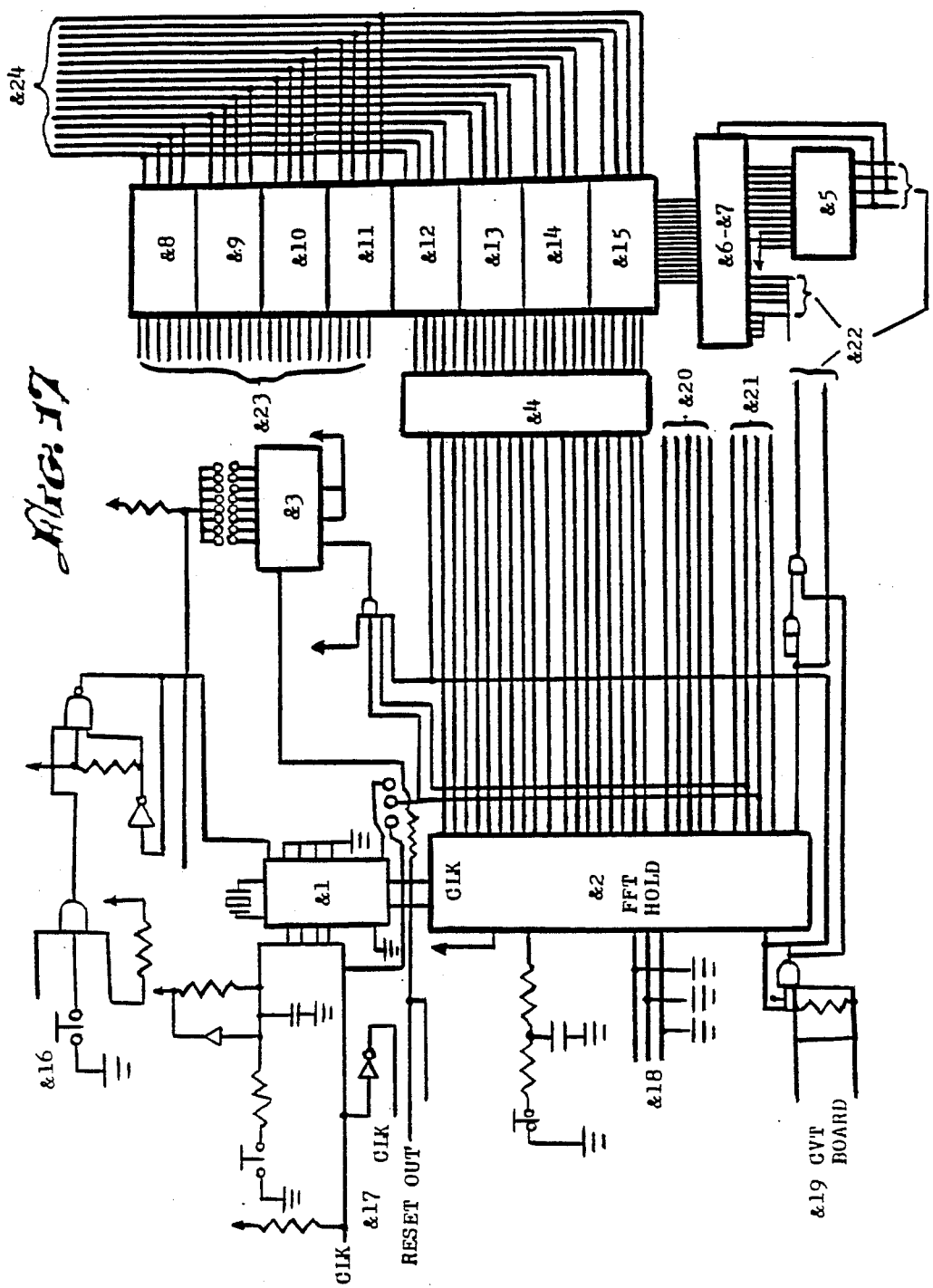
FIG. 17 describes a concise, generalized schematic portion of a VLSI logic circuit controlling the timing sequencing and the like of the piezoelectric motivator complex.
Figure 20:
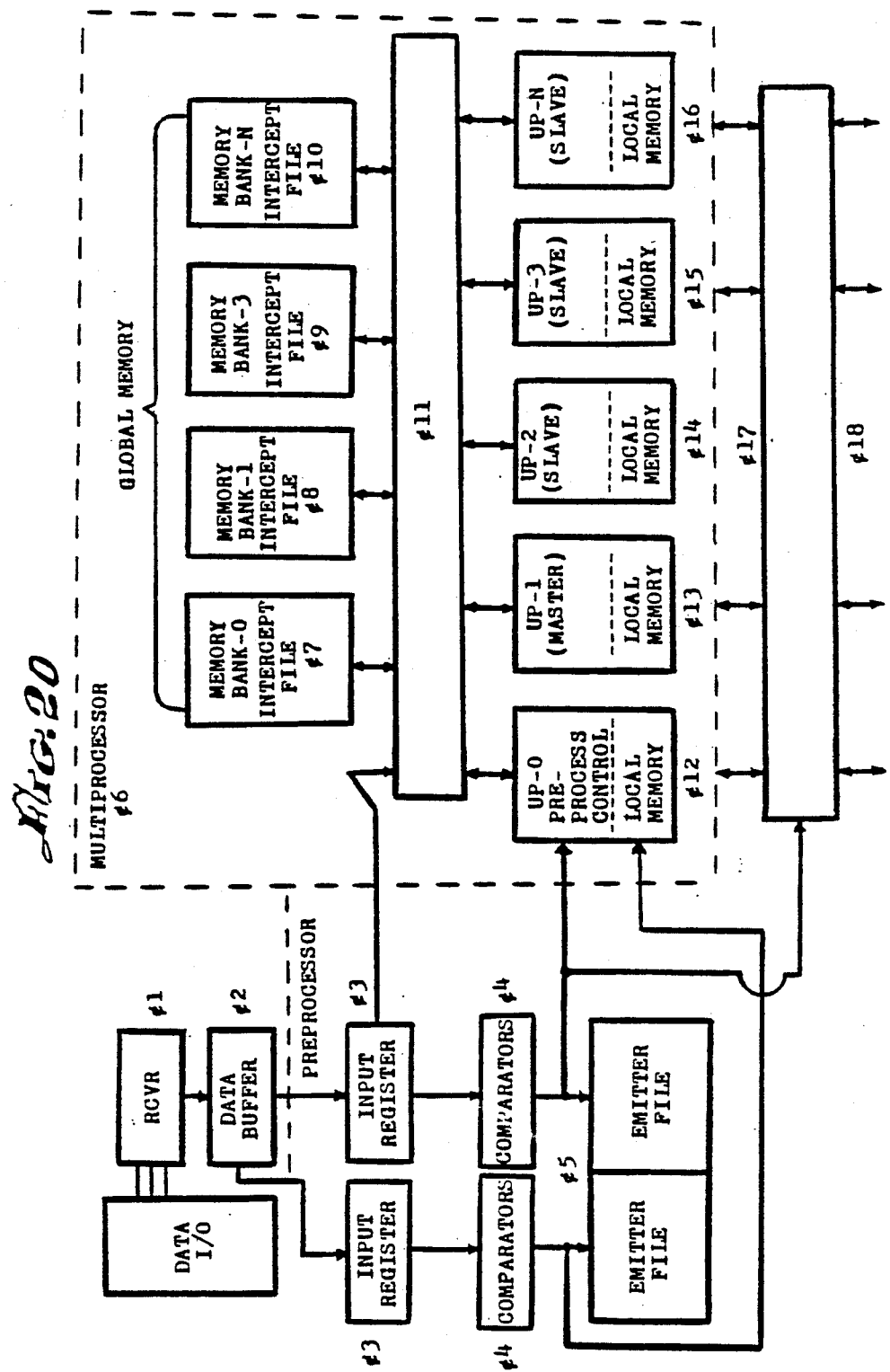

FIG. 17 describes in part one of several timing oscillator circuits or sequencer means deployed by the device. The partial design schematic, which is depicted in FIG. 17 is a basic variation of a commercially available circuit, which can be provided by companies such as Intel, I.B.M. or others. The circuitry disclosed in FIG. 21 predisposes the operation of the logic circuit, which is depicted in FIG. 20. The key integrated circuits in FIG. 17 are assigned the alphanumeric values &1 through &15. Elements &16 through &24 are indicative of I/O from other circuits. The capacitance diode, resistive elements are readily understandable by those skilled in the art and are not assigned to alphanumeric values.

Figure 18:
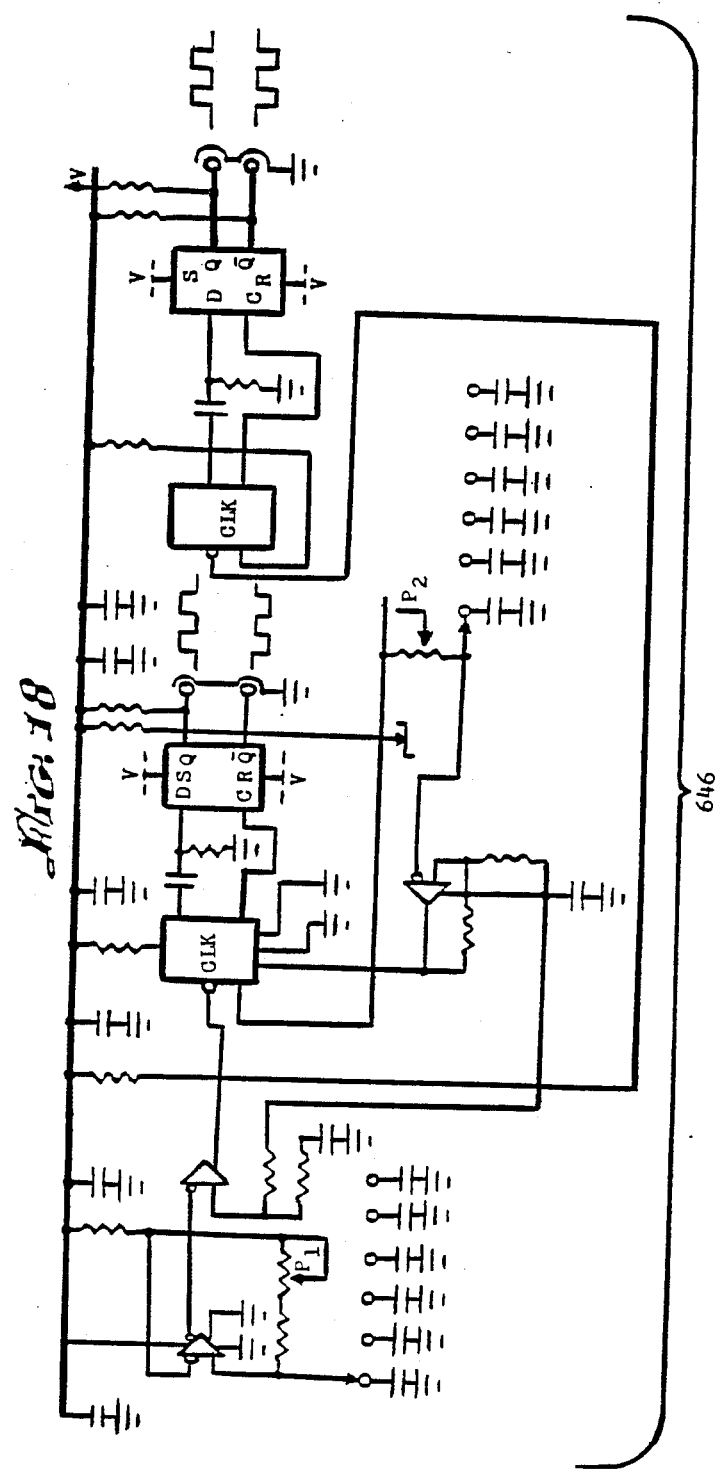
FIG. 18 is an over simplified view of an ancillary timing sequencer, controlling the transmission of power, timing, torque and a number of types of piezoelectric motivator means which are actuated.

FIG. 18 represents a partial concise, modified circuit diagram of one of the ancillary timing sequencers. Here a commercially available sequencer is modified with an additional electro-optical oscillators and monostable multivibrator means. The circuit disclosed within FIG. 18 herein is composed exclusively of commercially available electronic components. The sequencer disclosed herein above is designated entirely by a single numeral, number 646 for simplicity sake, and it has varying pulse widths which range from 10 milliseconds to less than several nanoseconds.

Figure 19:
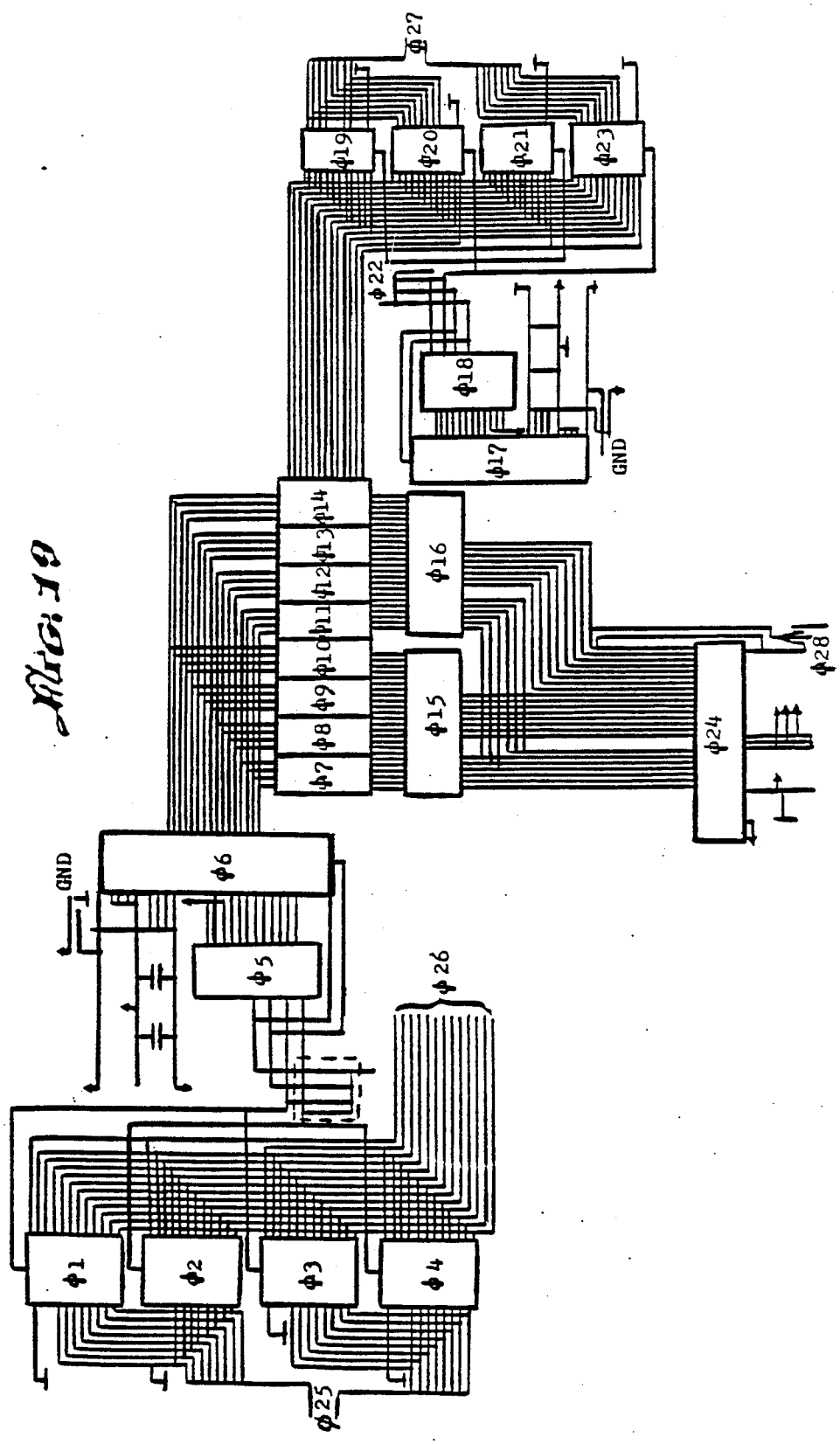
FIG. 19 denotes a portion of a VLSI logic circuits responsible for the organization, shaping and dispatching of signals.

FIG. 19 is indicative of a concise general schematic representation of a small portion of the logic circuit forming the basic embodiment of a single microcomputer means. The vital portion of the circuit employed, as denoted in FIG. 20 is equivalent to a multitude of similar such circuitry utilizing VLSI/VISHIC technology. The separate I.C. elements are so constructed as to be repetitive providing a reliable microcomputer with an increased ability to calculate and implement target acquisition, thrust parameters, pursuit vectors and related parameters. The I.C.'s are disposed on a single portion of the VLSI card which is replaceable in itself as well as each micro integrated circuit (I.C.) means. Each integrated circuit is designated by its own alphanumeric value and there are twenty-four I.C.'s depicted in the figure herein. The I.C.'s are listed by elements ∅1 through ∅24 with elements ∅15 with elements ∅16 and ∅24 acting as interrogators for logic elements ∅7 through ∅14. Comparator means for data are indicated in part by elements ∅1 through ∅4 and elements ∅19 through ∅23. Alphanumeric values ∅25, ∅26, ∅27 and ∅28 are indicative of origins of embarkation; wherein data either enters from other circuits or leaves from the portion of the circuit depicted in FIG. 19 and bound for other circuits. The other portions of the partial circuit diagram depicting capacitors, grid, resistive elements, or other components are straight forward to one skilled in the art; and therefore are not assigned any alphanumeric values.

FIG. 20 is a concise general perspective of a block diagram diagram which illustrates a single example of a microcomputer array processor element deposited on a single VHSI card. Information is received and encoded by element ¢1, which sends the data to be buffered ¢2. This data is then sent to a series of serial input registers, denoted by element ¢3. The data from ¢3 is sent to a comparator bank described by ¢4, which either processes the data by sending it to an emitter file ¢5, or to a series of interrogator circuits. The so-called microcomputer array processor means is designated by value ¢6, which is contained within the embodiment of elements that are a series of memory bank elements or intercept files, denoted by elements ¢7 through ¢10; wherein element ¢10 is a memory bank carried out to some desired nth element and elements ¢7 through ¢10 forming what is losely known as a globe memory. Element ¢11 forms a typical memory request logic interrogator means and elements ¢12 through ¢16, which form a preprocessor control, local memory interrogator, a master control local memory and a series of slave memories with EEPROM capabilities. The processed data and preprocessed data is entered directly into a system computer controlled means defined by embarkation points ¢17 and ¢18.

FIG. 21 is a partial schematic representation of only one of several timing oscillator circuits or sequencer means, which are deployed in the piezoelectric Gel prosthetic units. The partial design of the circuit of FIG. 21 like FIG. 17 is another variation of a commercially available module obtainable from companies like Intel, I.B.M. or their equivalents. The key intergrated circuits in FIG. 21 are assigned the alphanumeric values @1 through @22. Elements @23 through @34 are indicative of I/O from other circuits. The capacitance elements, diode and resistive elements are readily understandable by those skilled in the art and therefore like FIG. 17 are not assigned alphanumeric values. Temporal sequencing is provided by integrated circuits @5 through @12; whereas logic and shaping of the single source is provided by integrated means @13 @22, respectively.

Figure 22F:
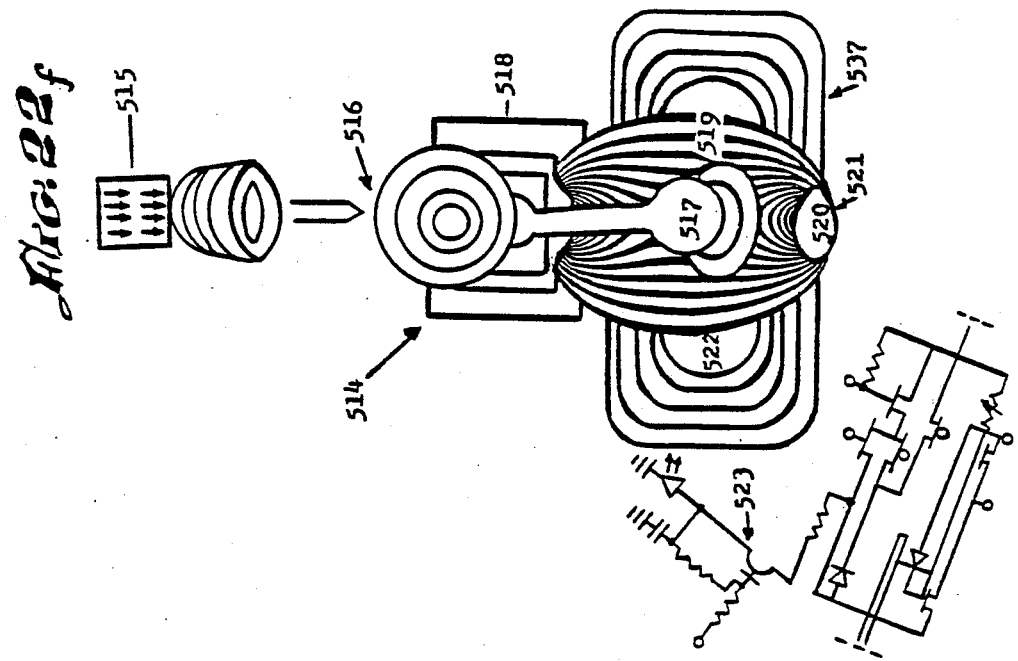
Figure 22E:
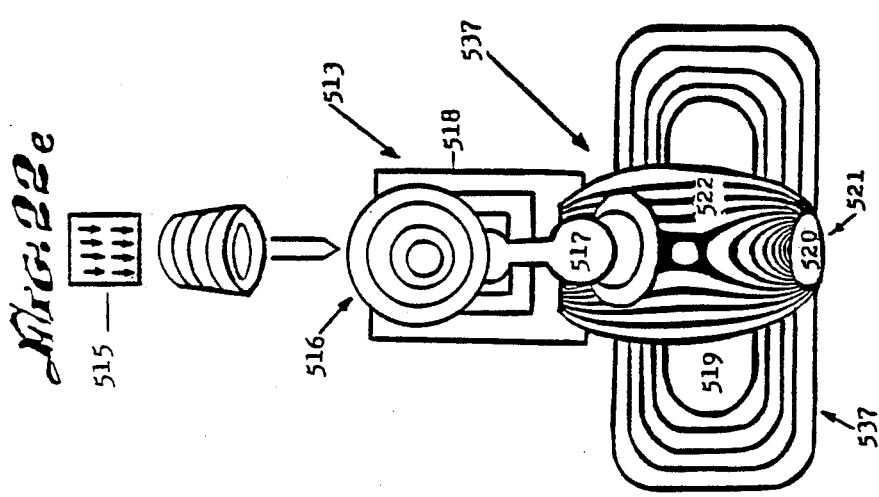

FIG. 22 represents in part a detailed sectioned view of a separate and distinct resilient cushion type of pressure transducer and its operative components. Contained within the operative framework of the cushion type pressoreceptor are three separate and distinct mechanisms of assessing applied pressures. The first mechanism for assessing pressure consists of a dielectric mediator of casterol and polyacrylides and/or other suitable commerically available fluids capable of undergoing alterations in its intrinsic viscosity, with increases or decreases in pressure from some optimum value. The second mechanism for the transduction of mechanical energy into electrical energy consists of a full complement of solid state multiconcentric spheroids, consisting of closely spatially oriented shells of electron donors and acceptors, which when subjected to applied pressure generates electrical conduction bands, discharging voltage to the surrounding dielectric medium. The aforementioned dielectric medium acting as a natural capacitor means, accumulates voltage collectively from the spheroids and then discharges the said voltage into a miniature current sensor. The period of voltage retention being relatively nil, several microseconds ($\mu s$) in duration and appears to be continuous in real time, such that the amount of pressure applied varies directly with the current generated. The third mechanism by which pressure is directly deduced consists of a myriad of submininature laser diodes and receiver diode means circumferentially located to measure the position of a piston means, which descends as pressure is applied and ascends in the absence of pressure against a specified resistance. Numerals 510, 511 and 512 of FIG. 22 are assigned to a complex of equivalent cushion pressoreceptors, a region wherein a group of pressoreceptors are activated by pressure and a array of fiber optics leading away from the pressoreceptors to a series of microprocessors or their equivalent means. The resolution of pressure or fine point discrimination, is contingent on the number of pressoreceptors per a given surface area; or in other words the greater number of pressoreceptors and the more closely they are packed or spaced to one another, the higher the resolution to two point discrimination. Two pressoreceptor component are designated by 513,514, respectively in FIGS. 22b and 22c. Element 513 is initially free of a pressure source, as denoted by 515; whereas the equivalent element 514 undergoes temporary structural deformation, when the weighted pressure source 515 engages element 514. A sectioned view of sensor 513 in FIGS. 22c and 22f reveals a pressure sensitive bulb numeral 516, which transmits its pressure through a variable elastic tubule, as denoted by number 517, both of which are housed or encapsulated in an elastic hermetically sealed entry chamber, described by unit 518. As the tubular structure of element 517 elongates it propels disc structure 519 through the compressible medium defined by number 520, which is contained or housed permanently in chamber means 521. The combined action of the disc means 519 and element 517 acts to displace the medium 520. As pressure directly increases, displacement of the medium also increases proportionately to said pressure. An increase in pressure produces porportionate increases in the intrinsic viscosity of the aforementioned medium indicated by a series of distortion lines assigned a single numeric value of 522, whereas the enclosed subchamber is designated by numeral 521. The increase in intrinsic viscosity due to increases in pressure or, its decrease in intrinsic viscosity in the absence of pressure is measured optically by a miniature laser dioded complex assigned the singular value of element 523. Numeral 537 represents a laser diode means and optical electronic circuit within the framework of a single substrate which are equivalent to that means described earlier in regards to the activation of a membrane structure. Numerals 524 through 536 of FIG. 22d represent in part the elastic compressible solid state spheroid, which is immersed in medium 520, which upon undergoing compression. Compression of said spheroid institutes a field effect transferring electrons from a donar means to an acceptor means and generating a minute electric current, which is conducted through the said medium. Electrical charges are conducted collectively through medium 520, wherein the current is gauged by a electronically biased voltage sensor, which is commercially available, but not shown in the drawings. The said solid state spheres are composed of a commercially available material that operates in a manner well understood by those skilled in the art and are resilient or compliant enough to return to an uncompressed state in the absense of pressure allowing the current to flow back to the said spheres from the medium, returning the said spheres to their previous electronic equilibrium. The spheres are rendered optically transparent to any said laser beam source as to not interfer with alterations in viscosity readings. A network of fiber optics elements associated with miniature laser diodes and an array of sensory elements measures the motion of disc 519 and elongation of tubule 517 by vertical displacement vectors. As tubule element 517 elongates and the disc means descends various linear optical circuits are switched off indicating the force of the pressure by the position of the circuit interrupted. Optical circuits are of course re-established when the tubule structure 517 contracts and the disc means 519 begins to make its ascent. All of the aforementioned laser diode means operate at alternate time intervals, with each having an operative life approaching or in excess of 100,000 hours and a rendundancy factor, such that the said lasers are arranged so that when one operative member fails another equivalent operative member takes its place.

Figure 23:
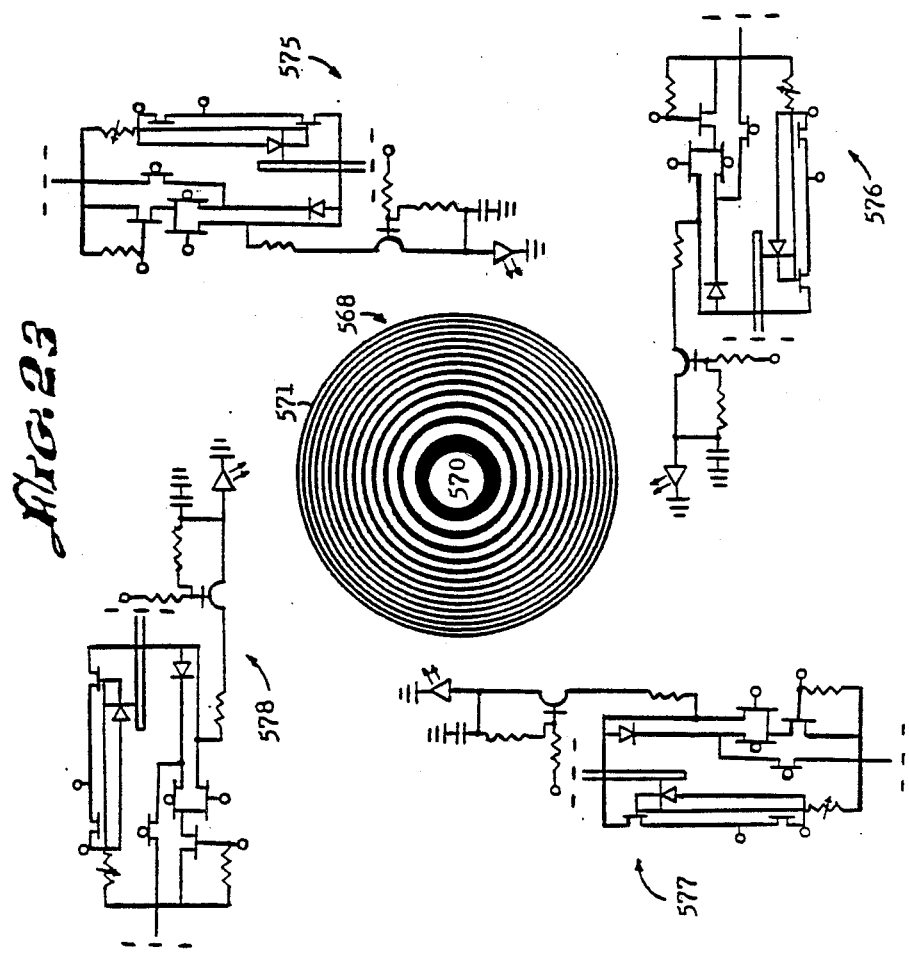
FIGS. 23, 23a, 23b, 23c, and 23d are is concise pictorial renderings of a fresnel type deformation lens pressoreceptor means.
Figure 23B:
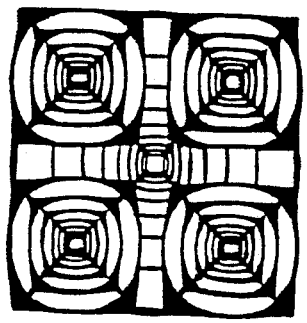
Figure 23A:
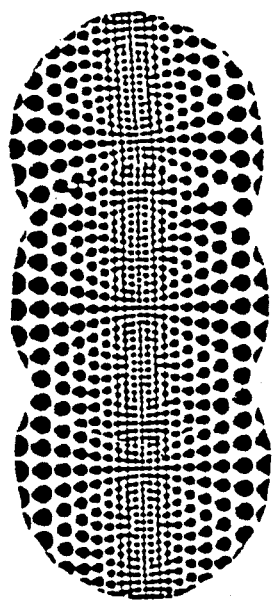
Figure 23C:
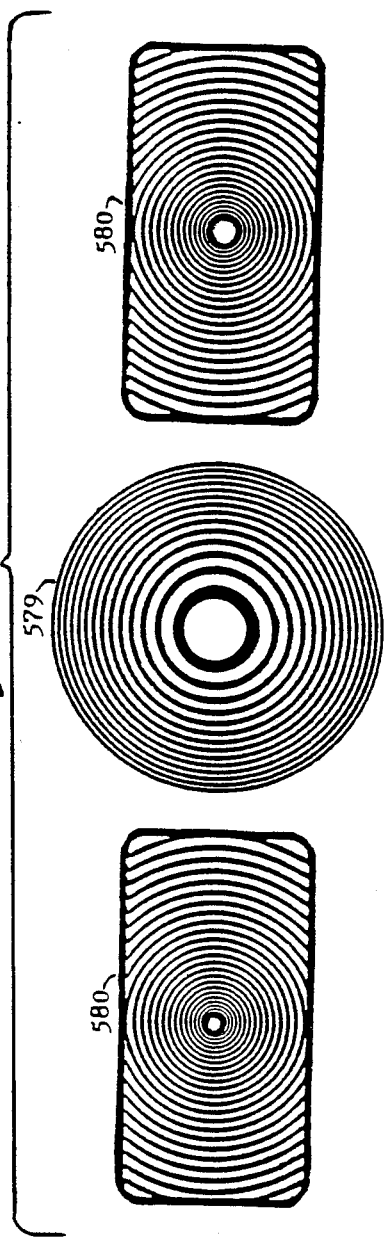
Figure 23D:
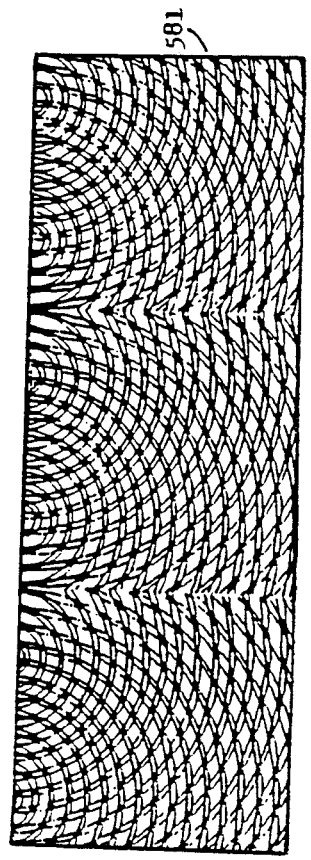

FIG. 23 is a concise general pictorial rendering of a fresnel type of deformation lense pressoreceptor means. The principle behind the detection of applied pressure for the said pressoreceptor is a simplistic two fold process, wherein laser interferometry and diffraction patterns are generated by the temporary bending or physical distortion initiated by the direct application of pressure. First a series of mutually disposed overlapping concentric rings designated by numerals 538 through 570 which are etched into the basic embodiment of a variable elastic disc means, which is assigned the single numeric value of 571. The elastic disc 571, is flexible and automatically returns to its flat static state in the absense of pressure formed from a readily available commercial polymorphic plastic, which may or may not be covered with a suitable dielectric medium as defined by element 572. The dielectric 572 and/or plane disc structure number 568 is further coated by a holographic film formed from a typical emulsion pattern and covered by a protective transparent plate. The holographic emulsion and protective plate means are shown in FIGS. 23a and 23b and are assigned the numeric values of 573 and 574 respectively. A complex of subminiature laser diodes act as the source of laser light by alternately transilluminating the entire said disc structure of the emulsion area with a series of miniature laser sources represented in part by numerals 575 through 578. The assemblage of lasers are placed at fixed points and the amount of deformation at each point is correlated with a reference beam from a miniature diode laser at a fixed centrally located point. A full complement of sensory diodes are contained in disc structures 579, 580 of FIG. 23c which are suspended above and below disc means 571. An array of high resolution array of sensors, not shown, detect both the angular shift in diffraction patterns and the spatial separation induced in ringlet patterns embodied within the holographic emulsion described in part by structure 573. The holographic plate is described in part by numeral 581 of FIG. 23d, which embodies said emulsion structure 573. Pressure applied to structures 579, 580, 581 and 573 induces deformation within said structures and subsequent alterations in the aforementioned patterns.

FIG. 24 entails a concise pictorial view of a gravity depended charged droplet proprioceptor means. The operative mechanism behind the charged droplet proprioceptor is the sequential operation of a series of equivalent asystematic mercury switches, each of which has a circuit that remains open until coming in contact with the charged droplet, completing a specific circuit. Each circuit when completed sends a precise digital signal specifying exact information relating to position or spatial orientation. A charged droplet numeral 582 rolls along the interior of spherical enclosure element 583. The charged droplet may consist of a suitable conductor such as mercury, conducting low voltage microelectrodes that are arranged along the entire surface of the spheres interior and are spaced an equal distance away from each other equivalent pair means as specified collectively by numeral 584 of FIG. 24a. A number of switching electrode pairs may be simultaneously stimulated in a given region of the sphere's interior, however only one region at a time is placed in contact with the said charged dropley. The droplet in a positive gravity environment remains in effect partially charged at every moment because it is always in contact with one or more electrode switching pair. Since the voltage at any given moment is extremely low, the droplet remains are relatively stable devoid of such effects as ionization, oxidation or electronic dispersal, which are indicative of high voltage switching means. Switching elements occur in pairs with each pair forming an open circuit until the said circuit is completed by a conductor, such as the charged metallic droplet as described in element 585 of FIG. 24b, completing several circuits of a switching array designated collectively by numeral 586. Numerals 587, 588, 589, and 590 of FIG. 24c designate a non-conducting holder means, a miniature conducting bundle for a given switching array and a deactivated droplet undergoing a charging sequence by a more detailed variation of a switching means.

FIG. 25 is a concise pictorial view of a portion of a continuous liquid crystal linear temperature sensing device. The operation of the said linear device occurs in accordance with similar such digital liquid crystal devices which are utilized to measure temperature; however before linear displacement occurs the liquid crystal elements flow outward to fill several mutually disposed circular elements. The device consists of a series of circularized platelet means, which are defined by elements 587 through 598 respectively. Each platelet means contains liquid crystal means which must fill each level of the circularly disposed elements via a thermal dependent diffusion gradient prior to moving to the next platelet means. Therefore the inner most level of a single platelet, as denoted by element 591 of FIGS. 25a and 25b will expand radially outward from shell 591a, filling shells 591b, 591c and 591d, prior to moving on to element 592. An array of linear electro-optical systems signal digitizers and related structures, as described earilier in this disclosure, are utilized in the lining the periphery of the liquid crystal encased linear sensor and are defined by values 599, 599a of FIG. 25c, respectively. Linear devices are extremely thin, microscopic and flexible, when compared to conventional thermal coupler devices and are resistant to power surges.

FIG. 26 discloses in a concise block diagram form a simplified fiber optical laser gyroscopic device utilized to discriminate positional data which is irrespective of gravitational variations. The entire compositional nature of the aforementioned laser system is composed entirely from commercially available component parts, made well available by numerous companies, and while such systems are being proposed and implemented for guidance systems in missles and related structures its explicit novel useage in the embodiment of prosthetic devices.

The basic configuration of a fiber optics based laser gyro system equivalent to that which is present in both the piezoelectric and conduit arm systems is presented in a illustrative manner by FIG. 26. Elements, $\emptyset1$, $\emptyset2$ and $\emptyset3$ denote the laser source, polarizing controller/polarizer means and directional coupler. Elements $\emptyset4$, $\emptyset5$, and $\emptyset6$ designate the phase modulator, the fiber optics spool and the solid state emission amplifier. Elements $\emptyset7$, $\emptyset8$, and $\emptyset9$ further designate a phonton detector, a wave comparator, and a wave descriminator means.

The principles of laser gyroscopics and interferometry are well understood and conceptually can be described by several common diagrams and field equations contained herein below: Emissive light is essentially split by an automated beam splitter at points and it travels along a circular path ⌀ until the same said emissive light completes its circuit and recombines at the original source of incident transmission, in this case point $\theta$, where the temproal transmissions interval can be appropriately differenced. The gyro phase shift is typically illustrated by the dual or dye transmission paths LCCW and LCW, ad disclosed in FIG. 28a.

If $W \neq 0$, $\Delta L \neq 0$ and the Path length difference $$\Delta L = LCW - LCCW \geqq \Delta \phi$$

$$\Delta \phi = \frac{8\pi AN}{\lambda c}$$

wherein W is defined as the rate of rotation, A denotes the area enclosed by the light path, and N is equivalent to the number of turns in the light path. The number of turns in a fiber optics coil is ideally directly proportional to the overall accuracy of the laser gyro system provided that the effective signal losses incurred can be limited to between 2 and 10 decibels per kilometer. The optimum diameter of the fiber optics element is less then or equal to 25 microns and the length of the spool to be greater than 1 kilometer but less than 100 kilometers. The absolute wavelength of laser light emitted by the laser source is defined by $\lambda$ and the constant C, which is defined by the speed of light.

FIG. 27 describes in brief a partial block diagram of a single continuous flow microcuvette analyzer complex.

Each microcuvette analyzer complex is associated with an equivalent reference complex and measurements from each are taken nearly simultaneously and then cross-referenced, identifying various substances on the basis of their intrinsic or characteristic absorbance, transmittance re-emittance and the electric motility. In the past prosthetic devices have been supplied with microprocessors, microcomputers and the like respond to the hosts galvanic skin response, electrical impulses due to the users intermuscular contractions and interneural implants consisting of an array of microelectrodes, which are sensitive to neural discharges of certain specified nerves. The aforementioned microanalyzer means allows the prosthetic devices to be responsive to levels of endrocrine, hormonal, or biochemical metabolite, as well as electrical impulses.

The extended sequential operation of apparatuses providing quantitative sampling of substances within bodily fluids of the host or user is an absolute necessity for prosthetic devices forming synthetic organ systems. The types of biochemicals or substances emitted by the user, the concentrations of said biochemicals or substances, reactivity, and other properties must be properly assess by the aforementioned apparatuses embodied within said prosthetic devices forming synthetic organs. Biochemicals, or other substances are repetitively scanned, entered, or taken nearly simultaneously and then cross-referenced, identifying various substances on the basis of their intrinsic or characteristic absorbance, transmittance, re-emittance and the electric motility. The methods by which the above mentioned processes are conducted are duely noted and incorporated into the specifications by reference for the following works, I.S.B.N. number 0.935536-25-6, U.S. Pat. No. 4,589,078 and related works. An inert transparent microcuvette, which is described by element 601 is bombarded by a specific emissive wavelength from a complex of miniature laser diodes, indicated by numeral 602, which is associated with a number of single substrate optical electronic systems, as described by the single numeric value 603. Each microcuvette element is filtered with a suitable electrophoretic gel composed of Sephadex G-70, or other suitable commercially available gels, which are capable of providing identification of substances via electromotility, as indicated by element 604. Each microcuvette element is also provided with a series of reservoir structures equipted with electro-optical elements, which are assigned collectively the numeric value 605. Certain specific organic proteins containing porphyrins, metabolites and organic sugars when placed in an acidic solution and irradiated with wavelengths in the ultraviolet or infrared region, re-emitted or fluoresce at characteristic wavelengths and positions located on a given electrophoretic gel. Wavelengths are readily altered by such frequency doublers as, sodium potassium niobate, $Ba_2NaNb_5O_{15}$, lithium iodate keyed to a specific substance; which induces fluorescence for certain specified compounds in the presence of acidified solution. Such said substances capable of undergoing fluorescence range from $\alpha$-adrenergic substances to a variety of porphyrin structures. The same said substances have characteristic absorptance and transmittance, which are monitored by an array of miniature laser diodes, not shown, each of which is responsive to a given wavelength. The entire microcuvette unit is encased by a protective capsule, designated by element 606, which acts as an optical emissive port. Electro-optical signals are conveyed along bidirectional fiber optics units 607 to and from the cuvette proper. The individual fiber optics termine interfaces with an array of sensory elements; which conveys the impulses to analog to digital convert means 607a, 607b and are then acted upon by filter element 607c, 607d prior to entering elements 620, 622. Electro-optical signals received from the sensory diode array are compared against a repertory of digital signals obtained from known substances of familar concentrations. Data is matched on the basis of a well known statistical format defined by the Best Fit Least Means Square Technique and variations of Bayes Maximum Likelyhood Method of statistical inference of incoming digitized signals, which are compared against known values. The known values and search procedures are encoded in an array or complex of microprocessor means or their equivalents, which act on a series of comparator designated by elements 608 through 613. Elements 614 through 617 designate microprocessors containing statistical formats, priority selection and other means to evaluate and compare data. Optical electronic converter unit means are assigned to elements leading to and from the piezoelectric device's CPU, which is not shown. The aforementioned optical electronic converter unit means are described collectively by numbers 618, 619, while the electro-optical digitizer means are assigned the numeric values 620 and 621, respectively. Informational input from other equivalent systems and output signals from the aforementioned system are exchanged and feed into a microcomputer array, or its equivalent, via bidirectional means 622 through 625.

FIG. 27a entails the means by which the user's bodily fluids are then retrieved from the user's skin for analysis and the means by which the said fluids are removed after analysis has been completed. The mechanisms by which said fluids of the user is withdrawn for sampling is capillary action and passive diffusion. A capillary tube described by numeral 626 conveys a negligible amount of said fluids eliminated by source emitters onto regions, numeral 627, to the microcuvette element described by number 606. Chemical byproducts of metabolites including, but not limited to lactic and pyruvic acid, organic salts and sugars and drugs or medicaments taken by the user are uniformly dispersed in minute quantities within the plasma component of the users bodily fluids, as described by numeral 600. Once the plasma is withdrawn from the source site it is subjected to examination by laser spectroscopy, laser doppler analysis, translational diffusion, microelectrophoresis and related processes, as described in FIG. 27. The mechanism by which sampled bodily fluids are evacuated from the microcurvette element is by electrostatic discharge. A small high voltage low amper electrical capacitances discharge by microelectrodes defined by numerals 628 to 630 are associated with the electrophoretic gel provides an electromotive force which is sufficient enough to expell the contents of the said microcuvette number 606, out through the capillary tube, 626. The expended said fluids exists the capillary tube structure disclosed by number 626, as a vapor which immediately evaporates into the atmosphere, leaving little if any residue. A vaccuum momentarily exists in the cuvette structure and capillary tube immediately following the electrical discharge. The vaccuum which is momentarily generated by the electrostatic discharge is immediately displaced by the admittance of purging fluids.

Although various alterations or modifications may be suggested by those skilled in the art, it is the intention of the inventor to embody within the patent warranted hereon all changes and modications, as reasonably and properly come within the scope of contributions to the art, without departing from the spirit of the invention.

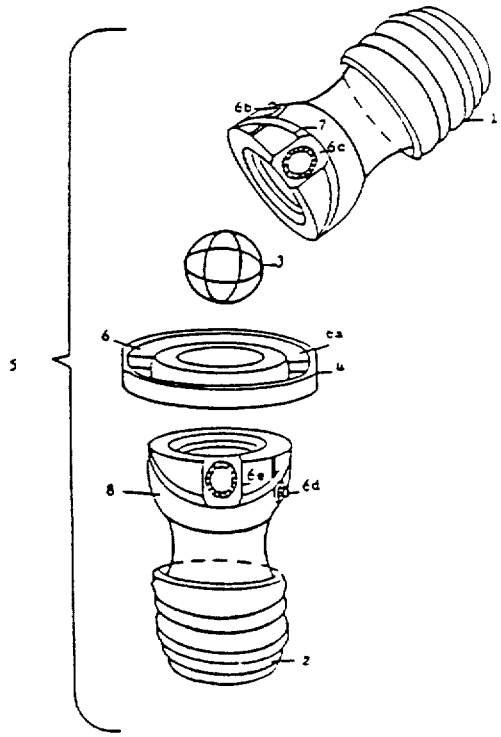

I claim:

1. A synthetic muscle adapted to power a prosthetic limb, comprising:
    a flexible tri-layer element, said tri-layer element including a central element which is flexible in at least two dimensions;
    a pair of opposed contractile elements carried by said central element and responsive to the application of electrical potentials thereto to change a physical characteristic thereof; and,
    means for selectively applying electrical potentials to each of said contractile elements and, wherein at least one of said opposed contractile elements includes a piezoelectric material embedded in a gelatinous material.

2. Apparatus according to claim 1 in which at-least-one of said opposed contractile elements exhibits bending upon application of said electrical potentials thereto.

3. Apparatus according to claim 1 in which at-least-one of said opposed contractile elements exhibits a change in volume upon application of said electrical potentials thereto.

4. Apparatus according to claim 3 in which said at-least-one contractile element is made of acrylamide.

5. Apparatus according to claim 4 in which said acrylamide is in an aqueous solution.

6. Apparatus according to claim 3 in which said at-least-one contractile element is of a polyelectrolytic material.

7. Apparatus according to claim 6 which includes, in addition, restoring means to restore the polyelectrolytic material to its original state following removal of electrical potentials therefrom.

8. Apparatus according to claim 7 in which said restoring means includes synthetic membranes adapted to be activated by laser.

9. Apparatus according to claim 8 in which said restoring means includes said laser actuated synthetic membranes coupled to sensory means for in vitro operation of said polyelectrolytic material.

10. Apparatus according to claim 9 in which said synthetic muscle is adapted to be placed in contact with the skin of a user, and bodily including means for retrieving fluids from the skin for laser analysis to determine the operation of said contractile elements forming prosthetic devices.

11. Apparatus according to claim 3 in which said at-least-one contractile element is made of polystyrene.

12. Apparatus according to claim 11 in which said polystyrene is in an non-aqueous solution.

13. Apparatus according to claim 1 in which said piezoelectric material is comminuted.

14. Apparatus according to claim 1 in which said means for selectively applying electrical potentials to each of said contractile elements includes a laser beam source for each contractile element, a photo-voltaic transducer electrically connected to its respective contractile element and fiber-optic means for optically coupling each said laser beam source to its respective photo-voltaic transducer.

15. Apparatus according to claim 1 in which said piezoelectric material is lead zirconate-titanate.

16. Apparatus according to claim 1 which includes, in addition, sensory elements carried by said contractile elements for monitoring the activities of said contractile elements.

* * * * *

UNITED STATES PATENT AND TRADEMARK OFFICE
CERTIFICATE OF CORRECTION

PATENT NO. : 4,895,574

DATED : Jan. 23, 1990

INVENTOR(S) : Larry Rosenberg

It is certified that error appears in the above-identified patent and that said Letters Patent is hereby corrected as shown below:

The title page should be deleted to appear as per attached sheet.

Signed and Sealed this

Ninth Day of October, 1990

*Attest:*

HARRY F. MANBECK, JR.

*Attesting Officer*     *Commissioner of Patents and Trademarks*

United States Patent [19]

Rosenberg

[11] Patent Number: 4,895,574
[45] Date of Patent: Jan. 23, 1990

[54] PIEZOELECTRIC MOTIVATOR FOR PROSTHETIC DEVICES

[76] Inventors: Larry Rosenberg, 3440 Caroline Ave., Culver City, Calif. 90230; Larry Rowan 3440½ Caroline Ave., Culver City, Calif. 90230.

[21] Appl. No.: 617,715
[22] Filed: Jun. 6, 1984
[51] Int. Cl.⁴ .................................. A61F 1/24
[52] U.S. Cl. ........................ 623/24; 623/27; 623/57
[58] Field of Search ............ 128/774, 630, 1 R; 604/14; 434/272; 310/311, 328-333, 340, 342, 344, 345, 12-15; 623/14, 24, 27, 57

[56] References Cited

U.S. PATENT DOCUMENTS

| | | | |
|---|---|---|---|
| 3,882,551 | 5/1975 | Helmer et al. | 623/14 |
| 4,342,936 | 8/1982 | Marcus et al. | 310/330 |
| 4,510,412 | 4/1985 | Suda et al. | 310/331 X |
| 4,546,500 | 10/1985 | Bell | 623/14 X |

OTHER PUBLICATIONS

Bailey's, *Textbook of Microscopic Anatomy*, 18th Edition, Williams & Wilkins, Baltimore Md., ©1984, pp. 261-286.

*Primary Examiner*—Francis Jaworski
*Attorney, Agent, or Firm*—Malke Leah Bas Meyer; Itzhak Ben Shlomo; Larry Rowan

[57] ABSTRACT

The invention embodies the construction and implementation of synthetic muscle elements into numerous prosthetic devices. The aforesaid synthetic muscle elements consist of piezoelectric Gels; which function to motivate artificial limbs, rotate artificial joints, institute peristaltic motion in synthetic muscle systems and perform other activities consistant with the operation of organic muscle tissue. Sensory elements and ancillary systems embodied within said synthetic muscle means are responsive to evoked potentials generated by the neurons or other impulse conducting structures of the user. The aforesaid synthetic muscle has the additional capacity to sense, measure and act in a compensatory fashion to adjust their operation to biochemicals emitted by the user including, neural humoral secretions, endocrine levels, the formation of metabolites and the tension or partial pressures of gases such as $CO_2$, $O_2$, or other substances.

16 Claims, 51 Drawing Sheets